United States Patent
Shinohata et al.

(10) Patent No.: US 9,884,810 B2
(45) Date of Patent: Feb. 6, 2018

(54) SEPARATION METHOD AND METHOD FOR PRODUCING ISOCYANATE

(75) Inventors: Masaaki Shinohata, Tokyo (JP); Nobuhisa Miyake, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 102 days.

(21) Appl. No.: 13/824,050

(22) PCT Filed: Oct. 4, 2011

(86) PCT No.: PCT/JP2011/072880
§ 371 (c)(1),
(2), (4) Date: Apr. 2, 2013

(87) PCT Pub. No.: WO2012/046734
PCT Pub. Date: Apr. 12, 2012

(65) Prior Publication Data
US 2013/0184488 A1    Jul. 18, 2013

(30) Foreign Application Priority Data

Oct. 4, 2010    (JP) ................... P2010-224877
Aug. 22, 2011    (JP) ................... P2011-180821

(51) Int. Cl.
C07C 263/20    (2006.01)
C07C 263/04    (2006.01)
(Continued)

(52) U.S. Cl.
CPC ............ C07C 263/20 (2013.01); B01D 3/009 (2013.01); B01D 3/143 (2013.01); B01D 3/34 (2013.01);
(Continued)

(58) Field of Classification Search
None
See application file for complete search history.

(56) References Cited

U.S. PATENT DOCUMENTS 3,919,278 A * 11/1975 Rosenthal ............ C07C 263/04
560/345
4,386,033 A    5/1983 Konig et al.
(Continued)

FOREIGN PATENT DOCUMENTS

CN    101652344 A    2/2010
EP    0092738 A1    11/1983
(Continued)

OTHER PUBLICATIONS

"Carbamates and Carbamoyl Chlorides" in Ullmann's Encyclopedia of Industrial Chemistry, eter Jäger, Costin N. Rentzea and Heinz Kieczka, Published Online : Jun. 15, 2000 pp. 553-560.*
(Continued)

Primary Examiner — Karl J Puttlitz
(74) Attorney, Agent, or Firm — Morgan, Lewis & Bockius LLP

(57) ABSTRACT

Disclosed is a method for separating, with a multi-stage distillation column, a mixture containing an active hydrogen-containing compound (A) and a compound (B) that reversibly reacts with the active hydrogen containing compound (A), the method comprising distillation-separating the active hydrogen-containing compound (A) and the compound (B) with the multi-stage distillation column in the presence of an intermediate-boiling-point inactive compound (C) that has a normal boiling point between a normal boiling point of the active hydrogen-containing compound (A) and a normal boiling point of the compound (B) and is chemically inactive for both of the (A) and the compound (B).

12 Claims, 13 Drawing Sheets

(51) Int. Cl.
*C07B 63/00* (2006.01)
*B01D 3/14* (2006.01)
*B01D 3/34* (2006.01)
*B01D 3/00* (2006.01)

(52) U.S. Cl.
CPC ............ *C07B 63/00* (2013.01); *C07C 263/04* (2013.01); *Y02P 20/127* (2015.11)

(56) References Cited

U.S. PATENT DOCUMENTS

| | | | |
|---|---|---|---|
| 4,495,107 A | | 1/1985 | Dodge et al. |
| 5,043,471 A | | 8/1991 | Hammen et al. |
| 5,284,969 A | * | 2/1994 | Hauner et al. ............... 560/345 |
| 5,731,458 A | * | 3/1998 | Dahmer ............... C07C 263/04 560/345 |
| 5,883,291 A | | 3/1999 | Schleenstein et al. |

FOREIGN PATENT DOCUMENTS

| | | |
|---|---|---|
| EP | 0122031 A1 | 10/1984 |
| EP | 0396977 A2 | 11/1990 |
| EP | 0542106 A2 | 5/1993 |
| EP | 0795543 A1 | 9/1997 |
| JP | 57-123159 A | 7/1982 |
| JP | 59-207837 A | 11/1984 |
| JP | 06-157448 A | 6/1994 |
| JP | 10-000301 A | 1/1998 |
| JP | 2010-215588 A | 9/2010 |

OTHER PUBLICATIONS

Konishi, "CDTECH MTBE Process," Chemical Engineering, 57: 77-79 (1993).
Hofmann, "Aromatic cyanates," Berichte der Duetchen Chemischen Gesellschaft [Reports of the German Chemical Society], 3: 653-658 (1870).
International Search Report issued in corresponding International Application No. PCT/JP2011/072880 dated Nov. 8, 2011.
Office Action issued in counterpart Chinese Patent Application No. 201180047921.8 dated Nov. 26, 2013.

\* cited by examiner

SEPARATION METHOD AND METHOD FOR PRODUCING ISOCYANATE

TECHNICAL FIELD

The present invention relates to the separation of a mixture containing plural types of reversibly reacting compounds, especially, a method for separating an isocyanate from a mixture containing the isocyanate and a hydroxy compound, and a method for producing an isocyanate.

BACKGROUND ART

Distillation is generally used in the separation of gas composition containing a plurality of components. The distillation is the procedure of concentrating a particular component in a mixture through the use of the difference in vapor pressure among individual component substances. As a mixture to be distilled is heated, individual components gradually evaporate from the surface of the solution, and boiling starts when the sum of the vapor pressures of the individual components agrees with the pressure of the system. The composition of vapors that emanate during this period almost depends on both of the composition of components on the surface of the solution and the vapor pressures (partial pressures) of the individual components at the temperature, according to the Raoult's law. A batch-type method and a continuous distillation method are known as industrial distillation methods.

The description above is the case where a reaction does not occur between components to be separated, and the case where a reaction occurs between gas components, between liquid-phase components, or between gas-liquid phases takes complicated evaporation behaviors.

For example, conventionally, in the case where equilibrium in an equilibrium reaction is disadvantageous to a product side, enhancing reaction efficiency (equilibrium conversion) by separating at least one type of products from the reaction system to make the equilibrium advantageous to the product side is generally performed. Although various methods are known as methods for separating products from the reaction system, distillation separation is one of the most generally performed methods. A method of pursuing a reaction by shifting the equilibrium reaction toward the product side with products removed from the reaction system by distillation is called reactive distillation, and an explanation about the reactive distillation is described in, for example, Non Patent Literature 1 by showing specific examples.

In general, the reactive distillation is carried out by using a distillation column such as a continuous multi-stage distillation column (reactive distillation apparatus). While higher-boiling-point components contained in a reaction solution become mostly distributed on the lower stage side of the distillation column along with the progress of the reaction in performing reactive distillation within the distillation column, lower-boiling-point components become mostly distributed on the upper stage side of the distillation column. Thus, in the distillation column, the internal temperature (solution temperature) decreases with movement from the bottom of the column toward the top of the column. The lower the temperature is, the lower the reaction rate of the equilibrium reaction becomes. Therefore, the reaction rate lowers with movement from the bottom of the column toward the top of the column in performing reactive distillation within the distillation column. Specifically, the reaction efficiency of the equilibrium reaction decreases with movement from the bottom of the column toward the top of the column in performing reactive distillation within the distillation column.

Thus, further increasing a temperature within the column has been studied in order to more improve reaction efficiency, i.e., to more accelerate the reaction rate, and a method of advantageously pursuing a reaction by supplying a solvent to a reactive distillation column and increasing a temperature within the reactive distillation column is disclosed in, for example, in Patent Literature 1, as a method for efficiently performing an equilibrium reaction represented by raw material (P)+raw material (Q)⇔ product (R)+product (S), especially, a transesterification reaction.

On the other hand, in the distillation separation of products in a system in which an equilibrium reaction represented by raw material (P)⇔ product (R)+product (S) exists, distillation is difficult in the case where the reaction rate is higher in the right-to-left direction (i.e., in reverse reaction) than in the left-to-right direction at a distillation separation temperature. In such a reaction, equilibrium may tilt toward the right side (product side) in a high-temperature region, and the case where distillation separation is influenced by other side reactions or the like is frequent in a high-temperature region though there is also a possibility of distillation separation. For example, it is not preferable to apply the method as described above to, for example, the distillation separation of a mixture containing an active hydrogen-containing compound and a compound that reversibly reacts with the active hydrogen-containing compound, especially, the distillation separation of a thermally decomposable product such as an N-substituted carbamic acid ester, an N-substituted thiocarbamic acid ester, or an N-substituted dithiocarbamic acid ester. For example, the case of thermal decomposition of the N-substituted carbamic acid ester is based on the following reason:

It has been known since long ago that an isocyanate and a hydroxy compound are obtained by the thermal decomposition of the N-substituted carbamic acid ester (see e.g., Non Patent Literature 2). The basic reaction of thermal decomposition of the N-substituted carbamic acid ester is illustrated by the following formula:

[Chemical Formula 1]

(1)

wherein
R represents an a-valent organic residue; R' represents a monovalent organic residue; and a represents an integer of 1 or larger.

The thermal decomposition reaction represented by the formula is reversible, and its equilibrium tilts at low temperatures toward the left-hand side where an N-substituted carbamic acid ester forms, and by contrast, tilts at high temperatures toward the right-hand side where an isocyanate and a hydroxy compound form.

Meanwhile, the N-substituted carbamic acid ester tends to be accompanied with various irreversible side reactions such as unfavorable thermal denaturation reactions and the condensation reaction of the isocyanate that forms by the thermal decomposition of the N-substituted carbamic acid ester. Examples of the side reactions include a reaction forming a urea bond represented by, for example, formula (2), a reaction forming carbodiimides represented by, for example, formula (3), and a reaction forming isocyanurates represented by, for example, formula (4):

[Chemical Formula 2]

$$R-\overset{H}{N}-\overset{O}{\overset{\|}{C}}-O-R' + R'-O-\overset{O}{\overset{\|}{C}}-\overset{H}{N}-R \longrightarrow \quad (2)$$

$$R-\overset{H}{N}-\overset{O}{\overset{\|}{C}}-\overset{H}{N}-R + R'-O-\overset{O}{\overset{\|}{C}}-O-R' \quad (3)$$

$$R-N=C=O + O=C=N-R \longrightarrow$$
$$R-N=C=N-R + CO_2 \quad (4)$$

$$3\ R-N=C=O \longrightarrow$$

[isocyanurate ring structure with R groups on three N atoms and O on three C atoms]

wherein R represents an aliphatic group or an aromatic group.

Particularly, in the case where the N-substituted carbamic acid ester is an N-substituted polycarbamic acid ester, a plurality of groups in one molecule may cause the side reactions as described above to form a high-molecular-weight form. Thus, it is impossible to solve these problems only by increasing a temperature within the distillation column using, for example, the method of Patent Literature 1 described above.

In the production of an isocyanate by the thermal decomposition of an N-substituted carbamic acid ester, a method of rapidly separating reaction products or decreasing the formation of by-products by dilution with an inactive solvent has been devised for reducing the formation of by-products capable of forming deposits in a reactor.

A method of using a reactor in a thin film form or tube form to thermally decompose an N-substituted carbamic acid ester in the presence of an inactive solvent is disclosed in, for example, Patent Literature 2 and Patent Literature 3. A method of using a reaction column to thermally decompose an N-substituted carbamic acid ester in the presence of an inactive solvent is disclosed in Patent Literature 4.

Moreover, a method of using a reactive rectifying column to thermally decompose an N-substituted carbamic acid ester in the presence of a particular inactive solvent and at the same time, separate an isocyanate and an alcohol that form is described in Patent Literature 5 and Patent Literature 6.

CITATION LIST

Patent Literature

Patent Literature 1: Japanese Patent Application Laid-Open Publication No. 10-301
Patent Literature 2: EP Patent Publication No. 92,738
Patent Literature 3: EP Patent Publication No. 396,977
Patent Literature 4: EP Patent Publication No. 542,106
Patent Literature 5: U.S. Pat. No. 5,731,458
Patent Literature 6: U.S. Pat. No. 5,883,291

Non Patent Literature

Non Patent Literature 1: "Journal of Chemical Engineering of Japan" Vol. 57, No. 1, p. 77-79 (1993)
Non Patent Literature 2: Berichte der Deutschen Chemischen Gesellschaft, Vol. 3, 1870, p. 653

SUMMARY OF INVENTION

Technical Problem

In a method described in Patent Literatures 5 and 6, a liquid from the bottom of a reactive rectifying column is only a heat transfer medium, and it is thus considered that the thermal decomposition of an N-substituted carbamic acid ester advantageously proceeds, while an isocyanate collected from the reactive rectifying column contains an alcohol and a compound having an N-substituted carbamic acid ester group presumed to form when the isocyanate reacts with the alcohol. Since the isocyanate reacts with the alcohol to form an N-substituted carbamic acid ester, it is not a satisfactory method from the viewpoint of separation efficiency.

As described above, for example, a method of thermally decomposing an N-substituted carbamic acid ester in an inactive solvent has been studied in order to suppress a thermal denaturation reaction caused by the reaction between N-substituted carbamic acid esters in a thermal dissociation equilibrium reaction and also in the distillation separation of products (e.g., product (R) and product (S)) in the thermal dissociation equilibrium. However, the point where an N-substituted carbamic acid ester forms again and reduces isocyanate yields in the course of the process of separating an isocyanate and a hydroxy compound that form by thermal decomposition, is still a problem.

An object of the present invention is to provide the separation of a mixture containing plural types of reversibly reacting compounds, especially, a method for efficiently separating an isocyanate from a mixture containing the isocyanate and a hydroxy compound, particularly, a method for efficiently separating an isocyanate and a hydroxy compound that form by the thermal decomposition of an N-substituted carbamic acid ester.

Solution to Problem

Accordingly, the present inventors have conducted diligent studies on the object and consequently completed the present invention by finding that the object is attained by a method for separating, with a multi-stage distillation column, a mixture containing an active hydrogen-containing compound (A) and a compound (B) that reversibly reacts with the active hydrogen-containing compound (A), the method comprising distillation-separating the active hydrogen-containing compound (A) and the compound (B) with the multi-stage distillation column in the presence of an intermediate-boiling-point inactive compound (C) that has a normal boiling point between a normal boiling point of the active hydrogen-containing compound (A) and a normal boiling point of the compound (B) and is chemically inactive for both of the active hydrogen-containing compound (A) and the compound (B).

Specifically, the present invention is as follows:
as the first aspect,

[1] a method for separating, with a multi-stage distillation column, a mixture containing an active hydrogen-containing compound (A) and a compound (B) that reversibly reacts with the active hydrogen-containing compound (A), the method comprising distillation-separating the active hydrogen-containing compound (A) and the compound (B) with the multi-stage distillation column in the presence of an intermediate-boiling-point inactive compound (C) that has a normal boiling point between a normal boiling point of the active hydrogen-containing compound (A) and a normal boiling point of the compound (B) and
is chemically inactive for the active hydrogen-containing compound (A) and the compound (B);

[2] the method according to [1], comprising supplying the mixture to an inactive layer comprising the intermediate-boiling-point inactive compound (C), formed within the multi-stage distillation column;

[3] the method according to [1] or [2], comprising supplying the mixture in a gas state to the multi-stage distillation column;

[4] the method according to any one of [1] to [3], wherein the compound (B) is an isocyanate and/or an isothiocyanate;

[5] the method according to any one of [1] to [4], wherein the active hydrogen-containing compound (A) is at least one compound selected from the group consisting of a hydroxy compound, a thiol, an aromatic thiol, and a hydrogen halide;

[6] the method according to any one of [1] to [5], wherein the mixture is a mixture obtained by the thermal decomposition reaction of a compound represented by formula (5):

[Chemical Formula 3]

(5)

wherein $R^1$ represents one group selected from the group consisting of an aliphatic group having 1 to 22 carbon atoms and an aromatic group having 6 to 22 carbon atoms, and the group may contain an oxygen atom and/or a nitrogen atom;

Y represents an oxygen atom or a sulfur atom;

Z represents one group selected from the group consisting of a residue in which a hydrogen atom has been removed from the —OH group of the hydroxy compound, a residue in which a hydrogen atom has been removed from the —SH group of the thiol or the aromatic thiol, and a halogen atom; and n represents an integer of 1 to 10;

[7] the method according to [6], wherein the compound represented by formula (5) is an N-substituted thiocarbamic acid ester wherein Y is a sulfur atom and Z is a residue in which a hydrogen atom has been removed from the —OH group of the hydroxy compound;

[8] the method according to [6], wherein the compound represented by formula (5) is an N-substituted carbamic acid ester wherein Y is an oxygen atom and Z is a residue in which a hydrogen atom has been removed from the —OH group of the hydroxy compound;

[9] the method according to [8], wherein the N-substituted carbamic acid ester is an N-substituted carbamic acid ester obtained by reacting a carbonic acid ester and an organic primary amine;

[10] the method according to [9], wherein the N-substituted carbamic acid ester is an N-substituted carbamic acid ester obtained by reacting urea, an organic primary amine, and a hydroxy compound; and

[11] the method according to [10], wherein the N-substituted carbamic acid ester is an N-substituted aromatic carbamic acid ester; and as the second aspect

[12] a method for producing an isocyanate, comprising: a step of obtaining a mixture containing an isocyanate and a hydroxy compound by the thermal decomposition reaction of an N-substituted carbamic acid ester; and a step of separating the isocyanate from the mixture by the method according to [1].

Advantageous Effects of Invention

According to the present invention, one can efficiently separate and collect a compound that reversibly reacts with an active hydrogen-containing compound from a mixture containing the active hydrogen-containing compound and the compound that reversibly reacts with the active hydrogen-containing compound, and can efficiently separate and collect, especially, an isocyanate from a mixture containing the isocyanate and a hydroxy compound.

DESCRIPTION OF EMBODIMENTS

Figure 1:
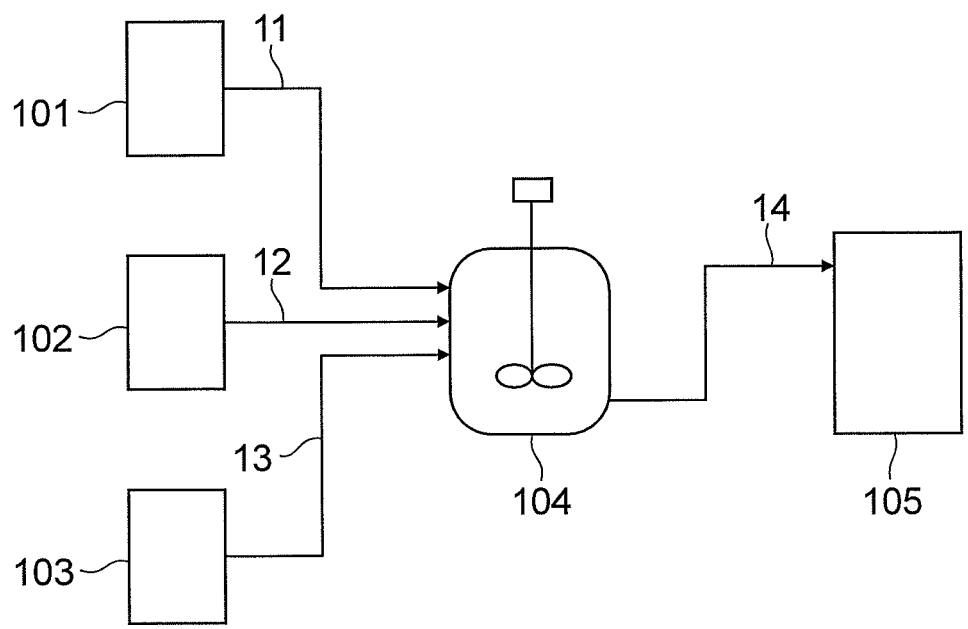
FIG. 1 is an illustrative diagram showing one example of an N-substituted carbamic acid ester producing apparatus.

Hereinafter, the mode for carrying out the present invention (hereinafter, referred to as the "present embodiment") will be described in detail. Incidentally, the present invention is not limited to the embodiments below and can be modified variously within the scope of the spirit thereof and carried out.

A separation method of the present embodiment is a method for separating, with a multi-stage distillation column, a mixture containing an active hydrogen-containing compound (A) and a compound (B) that reversibly reacts with the active hydrogen-containing compound, the method comprising distillation-separating the active hydrogen-containing compound (A) and the compound (B) with the multi-stage distillation column in the presence of an intermediate-boiling-point inactive compound (C) that has a normal boiling point between a normal boiling point of the active hydrogen-containing compound (A) and a normal boiling point of the compound (B) and is chemically inactive for both of the active hydrogen-containing compound (A) and the compound (B). This inactive compound is referred to as an "intermediate-boiling-point inactive compound" in some cases.

In general, a reversible reaction refers to, of chemical reactions, a reaction in which a reaction from the original system (raw material) to the product side (products) (forward reaction) and contrarily, a reaction that returns from the product side to the original system (reverse reaction) both occur, and in the present embodiment, the "compound (B) that reversibly reacts with the active hydrogen-containing compound" is a compound capable of reacting with the active hydrogen-containing compound (A) to form a conjugate of (A) and (B) and is a compound to which a reaction system represented by formula (6) holds:

[Chemical Formula 4]

Active hydrogen-containing compound (A)+Compound (B) that reversibly reacts with the active hydrogen-containing compound→Conjugate of (A) and (B)     (6)

In general, if only such forward and reverse reactions occur in a certain system, the system eventually stabilizes in an equilibrium state containing given amounts of substrates and products. Such a reaction system capable of forming the equilibrium state is called an equilibrium reaction. Specifically, the "compound (B) that reversibly reacts with the active hydrogen-containing compound" can also be referred to as a "compound (B) capable of forming an equilibrium reaction with the active hydrogen-containing compound". In the present embodiment, the mixture containing the active hydrogen-containing compound (A) and the compound (B) that reversibly reacts with the active hydrogen-containing compound is preferably a mixture in which (A), (B), and the conjugate of (A) and (B) are in an equilibrium state represented by formula (7) in the mixture:

[Chemical Formula 5]

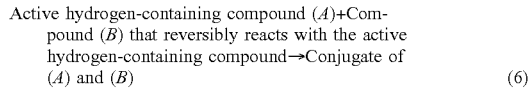
(A) + (B) ⇌ Conjugate of (A) and (B)     (7)

More preferably, (B) is a compound capable of forming thermal dissociation equilibrium with (A), and further preferably, (A), (B), and the conjugate of (A) and (B) are in a thermal dissociation equilibrium state in the mixture. The thermal dissociation is a reaction through which molecules or the like decompose by a rise in temperature and return to the original molecules by reverse reaction when the temperature decreases, and, taking the case of formula (7) as an example, is a reaction through which the conjugate of (A) and (B) decomposes by a rise in temperature to form (A) and (B), and (A) and (B) react to form the conjugate of (A) and (B) when the temperature decreases. In these reactions described above, one that is preferred is a system in which a catalyst is absent, though the catalyst may be present or may not be present in the system.

One that is preferred as (B) capable of forming such a system is an isocyanate and/or an isothiocyanate.

The isocyanate according to the present embodiment is a compound that corresponds to the latter half part "its hydrocarbyl derivatives: RN=C=O" of "The isocyanic acid tautomer, HN=C=O, of cyanic acid, HOC=N and its hydrocarbyl derivatives: RN=C=O." in the paragraph "isocyanates" specified by Rule C-8 described in the Nomenclature (IUPAC Nomenclature of Organic Chemistry) specified by IUPAC (The International Union of Pure and Applied Chemistry), and is preferably a compound represented by formula (8):

[Chemical Formula 6]

     (8)

wherein
$R^1$ represents one group selected from the group consisting of an aliphatic group having 1 to 22 carbon atoms and an aromatic group having 6 to 22 carbon atoms, and the group may contain an oxygen atom and/or a nitrogen atom; and
n represents an integer of 1 to 10.

Of the isocyanates represented by formula (8), one that is preferred is an isocyanate wherein n is 1 to 3. Examples of preferable $R^1$ include: linear hydrocarbon groups such as methylene, dimethylene, trimethylene, tetramethylene, pentamethylene, hexamethylene, and octamethylene; unsubstituted alicyclic hydrocarbon-derived groups such as cyclopentane, cyclohexane, cycloheptane, cyclooctane, and bis(cyclohexyl)alkane; alkyl-substituted cyclohexane-derived groups such as methylcyclopentane, ethylcyclopentane, methylcyclohexane (each isomer), ethylcyclohexane (each isomer), propylcyclohexane (each isomer), butylcyclohexane (each isomer), pentylcyclohexane (each isomer), and hexylcyclohexane (each isomer); dialkyl-substituted cyclohexane-derived groups such as dimethylcyclohexane (each isomer), diethylcyclohexane (each isomer), and dibutylcyclohexane (each isomer); trialkyl-substituted cyclohexane-derived groups such as 1,5,5-trimethylcyclohexane, 1,5,5-triethylcyclohexane, 1,5,5-tripropylcyclohexane (each isomer), and 1,5,5-tributylcyclohexane (each isomer); monoalkyl-substituted benzenes such as toluene, ethylbenzene, and propylbenzene; dialkyl-substituted benzenes such as xylene, diethylbenzene, and dipropylbenzene; and aromatic hydrocarbon-derived groups such as diphenylalkane and benzene. Among them, groups derived from hexamethylene, phenylene, diphenylmethane, toluene, cyclohexane, xylenyl, methylcyclohexane, isophorone, and dicyclohexylmethane are preferable.

Specific examples of preferable isocyanates include phenyl isocyanate, naphthalene isocyanate, hexamethylene diisocyanate, isophorone diisocyanate, diphenylmethane diisocyanate (each isomer), tolylene diisocyanate (each isomer), methylenebis(cyclohexane) diisocyanate, and naphthalene diisocyanate (each isomer).

The isothiocyanate according to the present embodiment corresponds to "Sulfur analogues of isocyanates: RN=C=S." in the paragraph "isothiocyanates" specified by Rule C-8 described in the Nomenclature (IUPAC Nomenclature of Organic Chemistry) specified by IUPAC (The International Union of Pure and Applied Chemistry), and is preferably a compound represented by formula (9):

[Chemical Formula 7]

$$R^1\!\!-\!\!(N\!\!=\!\!C\!\!=\!\!S)_n \qquad (9)$$

wherein $R^1$ represents one group selected from the group consisting of an aliphatic group having 1 to 22 carbon atoms and an aromatic group having 6 to 22 carbon atoms, and the group may contain an oxygen atom and/or a nitrogen atom; and n represents an integer of 1 to 10.

Of the isothiocyanates represented by formula (9), one that is preferred is an isothiocyanate wherein n is 1 to 3, and examples of preferable $R^1$ include: linear hydrocarbon groups such as methylene, dimethylene, trimethylene, tetramethylene, pentamethylene, hexamethylene, and octamethylene; unsubstituted alicyclic hydrocarbon-derived groups such as cyclopentane, cyclohexane, cycloheptane, and cyclooctane; alkyl-substituted cyclohexane-derived groups such as methylcyclopentane, ethylcyclopentane, methylcyclohexane, ethylcyclohexane, propylcyclohexane (each isomer), butylcyclohexane (each isomer), pentylcyclohexane (each isomer), and hexylcyclohexane (each isomer); dialkyl-substituted cyclohexane-derived groups such as dimethylcyclohexane (each isomer), diethylcyclohexane (each isomer), and dibutylcyclohexane (each isomer); tri-alkyl-substituted cyclohexane-derived groups such as 1,5,5-trimethylcyclohexane, 1,5,5-triethylcyclohexane, 1,5,5-tripropylcyclohexane (each isomer), and 1,5,5-tributylcyclohexane (each isomer); monoalkyl-substituted benzenes such as toluene, ethylbenzene, and propylbenzene; dialkyl-substituted benzenes such as xylene, diethylbenzene, and dipropylbenzene; and aromatic hydrocarbon-derived groups such as diphenylalkane and benzene. Among them, groups derived from hexamethylene, phenylene, diphenylmethane, toluene, cyclohexane, xylenyl, methylcyclohexane, isophorone, and dicyclohexylmethane are preferable.

Specific examples of preferable isothiocyanates include phenyl isothiocyanate, naphthalene isothiocyanate, hexamethylene diisothiocyanate, isophorone diisothiocyanate, diphenylmethane diisothiocyanate (each isomer), tolylene diisothiocyanate (each isomer), methylenebis(cyclohexane) diisothiocyanate, naphthalene diisothiocyanate (each isomer), and lysine diisothiocyanate.

On the other hand, (A) is an active hydrogen-containing compound. The "active hydrogen" in the active hydrogen-containing compound (A) refers to a hydrogen atom bonded to a halogen atom, an oxygen atom, a sulfur atom, a nitrogen atom, a silicon atom, or the like, and a hydrogen atom in a terminal methine group. It is, for example, hydrogen contained in an atomic group or a molecule such as a —OH group, a —C(=O)OH group, a —C(=O)H group, a —SH group, a —SO$_3$H group, a —SO$_2$H group, a —SOH group, a —NH$_2$ group, a —NH— group, a —SiH group, a —C≡CH group, or HX (X represents a halogen atom). The active hydrogen-containing compound (A) is a compound containing these active hydrogens described above and is preferably a compound containing a —OH group, a —SH group, or a —NH$_2$ group and a hydrogen halide (above-described HX (X is a halogen atom)).

One that is preferred as a specific compound is at least one compound selected from the group consisting of a hydroxy compound, a thiol, an aromatic thiol, and a hydrogen halide.

A preferable hydroxy compound is an alcohol or an aromatic hydroxy compound, and the case of the alcohol is a compound represented by formula (10):

[Chemical Formula 8]

$$R^5\!\!-\!\!(OH)_c \qquad (10)$$

wherein $R^5$ represents an aliphatic group having 1 to 50 carbon atoms which is substituted by c hydroxy group(s), or an aliphatic group having 7 to 50 carbon atoms which is a group to which an aromatic group is bonded; the —OH group of the alcohol represented by formula (10) is a —OH group unbound to an aromatic group; and c represents an integer of 1 to 3, provided that $R^5$ is a group that does not have active hydrogen other than the hydroxy group.

Examples of $R^5$ can include a methyl group, an ethyl group, a propyl group, a butyl group, a pentyl group, a hexyl group, a heptyl group, an octyl group, a nonyl group, a decyl group, a dodecyl group, an octadecyl group, a cyclopentyl group, a cyclohexyl group, a cycloheptyl group, a cyclooctyl group, a methylcyclopentyl group, an ethylcyclopentyl group, a methylcyclohexyl group, an ethylcyclohexyl group, a propylcyclohexyl group, a butylcyclohexyl group, a pentylcyclohexyl group, a hexylcyclohexyl group, a dimethylcyclohexyl group, a diethylcyclohexyl group, and a dibutylcyclohexyl group.

Specific examples of alcohols having such $R^5$ can include methanol, ethanol, propanol, butanol, pentanol, hexanol, heptanol, octanol, nonanol, decanol, dodecanol, octadecanol, cyclopentanol, cyclohexanol, cycloheptanol, cyclooctanol, methylcyclopentanol, ethylcyclopentanol, methylcyclohexanol, ethylcyclohexanol, propylcyclohexanol, butylcyclohexanol, pentylcyclohexanol, hexylcyclohexanol, dimethylcyclohexanol, diethylcyclohexanol, and dibutylcyclohexanol.

Moreover, examples of $R^5$ can also include a phenylmethyl group, a phenylethyl group, a phenylpropyl group, a phenylbutyl group, a phenylpentyl group, a phenylhexyl group, a phenylheptyl group, a phenyloctyl group, and a phenylnonyl group.

Specific examples of alcohols having such $R^5$ can include phenylmethanol, phenylethanol, phenylpropanol, phenylbutanol, phenylpentanol, phenylhexanol, phenylheptanol, phenyloctanol, and phenylnonanol.

Of the alcohols described above, an alcohol having one or two alcoholic hydroxy group(s) (hydroxy group(s) directly added to a carbon atom, other than the aromatic ring, constituting the hydroxy compound described above) is preferable in consideration of industrial use because it is generally low viscous, and one that is more preferred is a monoalcohol in which the alcoholic hydroxy group is 1.

Among these, an alkyl alcohol having 1 to 20 carbon atoms is preferable from the viewpoint of the ease of obtainment, the solubility of raw materials or products, etc.

In the case where the hydroxy compound is an aromatic hydroxy compound, the hydroxy compound is a compound represented by formula (11):

[Chemical Formula 9]

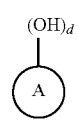
(11)

wherein ring A represents an organic group containing 6 to 50 carbon atoms which contains an aromatic group substituted by d hydroxy group(s) at any position that keeps aromaticity, and may be a single ring, a plurality of rings, or a heterocyclic ring or may be substituted by other substituents; and d represents an integer of 1 to 6.

One that is preferred is a structure in which ring A contains at least one structure selected from the group consisting of a benzene ring, a naphthalene ring, and an anthracene ring, and one that is more preferred is a structure in which ring A contains at least one benzene ring. Moreover, preferably, ring A is a group that does not have active hydrogen other than the hydroxy group.

The hydroxy group bonded to the aromatic group of ring A is a hydroxy group bonded to a carbon atom in the aromatic group of ring A, and the number of the hydroxy group is an integer of 1 to 6, preferably 1 to 3, more preferably 1 to 2, further preferably 1 (i.e., d=1). One that is more preferred is an aromatic monohydroxy compound in which the aromatic hydroxyl group is 1.

Examples thereof specifically include phenol, methylphenol (each isomer), ethylphenol (each isomer), propylphenol (each isomer), butylphenol (each isomer), pentylphenol (each isomer), hexylphenol (each isomer), octylphenol (each isomer), nonylphenol (each isomer), cumylphenol (each isomer), dimethylphenol (each isomer), methylethylphenol (each isomer), methylpropylphenol (each isomer), methylbutylphenol (each isomer), methylpentylphenol (each isomer), diethylphenol (each isomer), ethylpropylphenol (each isomer), ethylbutylphenol (each isomer), dipropylphenol (each isomer), dicumylphenol (each isomer), trimethylphenol (each isomer), triethylphenol (each isomer), and naphthol (each isomer).

A compound having one hydroxyl group directly bonded to the aromatic hydrocarbon ring constituting the aromatic hydroxy compound described above is preferable as the aromatic hydroxy compound. Although even an aromatic hydroxy compound having two or more hydroxyl groups directly bonded to the aromatic hydrocarbon ring constituting the aromatic hydroxy compound described above may be used as the aromatic hydroxy compound, it is preferred that the hydroxyl group directly bonded to the aromatic hydrocarbon ring should be 1 because one in which the hydroxy group is 1 is generally low viscous.

A preferable thiol is a compound represented by formula (12):

[Chemical Formula 10]

(12)

wherein $R^5$ represents an aliphatic group having 1 to 50 carbon atoms which is substituted by e sulfhydryl group(s), or a group consisting of an aliphatic group having 7 to 50 carbon atoms to which an aromatic group is bonded; the —SH group of the thiol represented by formula (12) is a —SH group unbound to the aromatic group; and e represents an integer of 1 to 3, provided that $R^5$ is a group that does not have active hydrogen other than the sulfhydryl group.

Examples of $R^5$ can include a methyl group, an ethyl group, a propyl group, a butyl group, a pentyl group, a hexyl group, a heptyl group, an octyl group, a nonyl group, a decyl group, a dodecyl group, an octadecyl group, cyclopentane, cyclohexane, cycloheptane, cyclooctane, methylcyclopentane, ethylcyclopentane, methylcyclohexane, ethylcyclohexane, propylcyclohexane, butylcyclohexane, pentylcyclohexane, hexylcyclohexane, dimethylcyclohexane, diethylcyclohexane, and dibutylcyclohexane.

Specific examples of thiols having such $R^5$ can include methanethiol, ethanethiol, propanethiol, butanethiol, pentanethiol, hexanethiol, heptanethiol, octanethiol, nonanethiol, decanethiol, dodecanethiol, octadecanethiol, cyclopentanethiol, cyclohexanethiol, cycloheptanethiol, cyclooctanethiol, methylcyclopentanethiol, ethylcyclopentanethiol, methylcyclohexanethiol, ethylcyclohexanethiol, propylcyclohexanethiol, butylcyclohexanethiol, pentylcyclohexanethiol, hexylcyclohexanethiol, dimethylcyclohexanethiol, diethylcyclohexanethiol, and dibutylcyclohexanethiol.

Moreover, examples of $R^5$ can also include a phenylmethyl group, a phenylethyl group, a phenylpropyl group, a phenylbutyl group, a phenylpentyl group, a phenylhexyl group, a phenylheptyl group, a phenyloctyl group, and a phenylnonyl group.

Specific examples of thiols having such $R^5$ can include phenylmethanethiol, phenylethanethiol, phenylpropanethiol, phenylbutanethiol, phenylpentanethiol, phenylhexanethiol, phenylheptanethiol, phenyloctanethiol, and phenylnonanethiol.

Of the thiols described above, a thiol having one or two thiolic sulfhydryl group(s) (sulfhydryl group(s) directly added to a carbon atom, other than the aromatic ring, constituting the thiol) is preferable in consideration of industrial use because it is generally low viscous, and one that is more preferred is a monothiol in which the thiolic sulfhydryl is 1.

Among these, an alkylthiol having 1 to 20 carbon atoms is preferable from the viewpoint of the ease of obtainment, the solubility of raw materials or products, etc.

A preferable aromatic thiol is a compound represented by formula (13):

[Chemical Formula 11]

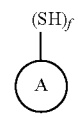
(13)

wherein ring A represents an organic group containing 6 to 50 carbon atoms which contains an aromatic group substituted by f sulfhydryl group(s) at any position that keeps aromaticity, and may be a single ring, a plurality of rings, or a heterocyclic ring or may be substituted by other substituents; and f represents an integer of 1 to 6.

One that is preferred is a structure in which ring A contains at least one structure selected from the group consisting of a benzene ring, a naphthalene ring, and an anthracene ring, and one that is more preferred is a structure in which ring A contains at least one benzene ring. Moreover, preferably, ring A is a group that does not have active hydrogen other than the sulfhydryl group.

The sulfhydryl group bonded to the aromatic group of ring A is a sulfhydryl group bonded to a carbon atom in the aromatic group of ring A, and the number of the sulfhydryl group is an integer of 1 to 6, preferably 1 to 3, more preferably 1 to 2, further preferably 1 (i.e., f=1). One that is more preferred is an aromatic monothiol compound in which the aromatic sulfhydryl group is 1.

Examples thereof specifically include benzenethiol, methylbenzenethiol (each isomer), ethylbenzenethiol (each isomer), propylbenzenethiol (each isomer), butylbenzenethiol (each isomer), pentylbenzenethiol (each isomer), hexylbenzenethiol (each isomer), octylbenzenethiol (each isomer), nonylbenzenethiol (each isomer), cumylbenzenethiol (each isomer), dimethylbenzenethiol (each isomer), methylethylbenzenethiol (each isomer), methylpropylbenzenethiol (each isomer), methylbutylbenzenethiol (each isomer), methylpentylbenzenethiol (each isomer), diethylbenzenethiol (each isomer), ethylpropylbenzenethiol (each isomer), ethylbutylbenzenethiol (each isomer), dipropylbenzenethiol (each isomer), dicumylbenzenethiol (each isomer), trimethylbenzenethiol (each isomer), triethylbenzenethiol (each isomer), and naphthalenethiol (each isomer).

A compound having one sulfhydryl group directly bonded to the aromatic hydrocarbon ring constituting the aromatic thiol is preferable as the aromatic thiol. Although even an aromatic thiol having two or more sulfhydryl groups directly bonded to the aromatic hydrocarbon ring constituting the aromatic thiol may be used as the aromatic thiol, an aromatic thiol having one or two of the sulfhydryl groups is preferable because it is generally low viscous, and one that is more preferred is an aromatic monothiol.

Examples of the hydrogen halide include hydrogen fluoride, hydrogen chloride, hydrogen bromide, and hydrogen iodide.

In the present embodiment, the mixture containing the active hydrogen-containing compound (A) and the compound (B) that reversibly reacts with the active hydrogen-containing compound is preferably a mixture obtained by the thermal decomposition reaction of a compound represented by formula (5):

[Chemical Formula 12]

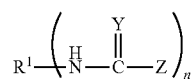

(5)

wherein $R^1$ represents one group selected from the group consisting of an aliphatic group having 1 to 22 carbon atoms and an aromatic group having 6 to 22 carbon atoms, and the group may contain an oxygen atom and/or a nitrogen atom;

Y represents an oxygen atom or a sulfur atom;

Z represents one group selected from the group consisting of a residue in which a hydrogen atom has been removed from the —OH group of the hydroxy compound, a residue in which a hydrogen atom has been removed from the —SH group of the thiol or the aromatic thiol, and a halogen atom; and n represents an integer of 1 to 10.

A specific one is an N-substituted carbamic acid ester represented by formula (14), an N-substituted-O-substituted thiocarbamic acid ester represented by formula (15), an N-substituted-S-substituted thiocarbamic acid ester represented by formula (16), an N-substituted dithiocarbamic acid ester represented by formula (17), and an N-substituted carbamic acid halogenide represented by formula (18):

[Chemical Formula 13]

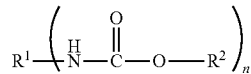

(14)

wherein $R^1$ represents one group selected from the group consisting of an aliphatic group having 1 to 22 carbon atoms and an aromatic group having 6 to 22 carbon atoms, and the group may contain an oxygen atom and/or a nitrogen atom;

$R^2$ represents one group selected from the group consisting of an aliphatic group having 1 to 50 carbon atoms and an aromatic group having 6 to 50 carbon atoms, and the group may contain an oxygen atom and/or a nitrogen atom; and n represents an integer of 1 to 10.

[Chemical Formula 14]

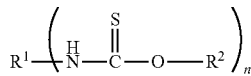

(15)

wherein $R^1$ represents one group selected from the group consisting of an aliphatic group having 1 to 22 carbon atoms and an aromatic group having 6 to 22 carbon atoms, and the group may contain an oxygen atom and/or a nitrogen atom;

$R^2$ represents one group selected from the group consisting of an aliphatic group having 1 to 50 carbon atoms and an aromatic group having 6 to 50 carbon atoms, and the group may contain an oxygen atom and/or a nitrogen atom; and n represents an integer of 1 to 10.

[Chemical Formula 15]

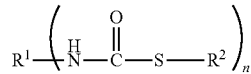

(16)

wherein $R^1$ represents one group selected from the group consisting of an aliphatic group having 1 to 22 carbon atoms and an aromatic group having 6 to 22 carbon atoms, and the group may contain an oxygen atom and/or a nitrogen atom;

$R^2$ represents one group selected from the group consisting of an aliphatic group having 1 to 50 carbon atoms and an aromatic group having 6 to 50 carbon atoms, and the group may contain an oxygen atom and/or a nitrogen atom; and n represents an integer of 1 to 10.

[Chemical Formula 16]

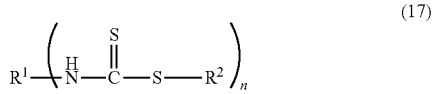

(17)

wherein

R¹ represents one group selected from the group consisting of an aliphatic group having 1 to 22 carbon atoms and an aromatic group having 6 to 22 carbon atoms, and the group may contain an oxygen atom and/or a nitrogen atom;

R² represents one group selected from the group consisting of an aliphatic group having 1 to 50 carbon atoms and an aromatic group having 6 to 50 carbon atoms, and the group may contain an oxygen atom and/or a nitrogen atom; and n represents an integer of 1 to 10.

[Chemical Formula 17]

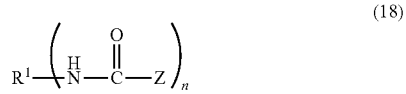

(18)

wherein

R¹ represents one group selected from the group consisting of an aliphatic group having 1 to 22 carbon atoms and an aromatic group having 6 to 22 carbon atoms, and the group may contain an oxygen atom and/or a nitrogen atom;

Z represents one atom selected from the group consisting of a chlorine atom, a bromine atom, and an iodine atom; and n represents an integer of 1 to 10.

In formulas (14) to (18), examples of preferable R¹ include: linear hydrocarbon groups such as methylene, dimethylene, trimethylene, tetramethylene, pentamethylene, hexamethylene, and octamethylene; unsubstituted alicyclic hydrocarbon-derived groups such as cyclopentane, cyclohexane, cycloheptane, cyclooctane, and bis(cyclohexyl)alkane; alkyl-substituted cyclohexane-derived groups such as methylcyclopentane, ethylcyclopentane, methylcyclohexane (each isomer), ethylcyclohexane (each isomer), propylcyclohexane (each isomer), butylcyclohexane (each isomer), pentylcyclohexane (each isomer), and hexylcyclohexane (each isomer); dialkyl-substituted cyclohexane-derived groups such as dimethylcyclohexane (each isomer), diethylcyclohexane (each isomer), and dibutylcyclohexane (each isomer); trialkyl-substituted cyclohexane-derived groups such as 1,5,5-trimethylcyclohexane, 1,5,5-triethylcyclohexane, 1,5,5-tripropylcyclohexane (each isomer), and 1,5,5-tributylcyclohexane (each isomer); monoalkyl-substituted benzene-derived groups such as toluene, ethylbenzene, and propylbenzene; dialkyl-substituted benzene-derived groups such as xylene, diethylbenzene, and dipropylbenzene; and aromatic hydrocarbon-derived groups such as diphenylalkane and benzene. Among them, groups derived from hexamethylene, phenylene, diphenylmethane, toluene, cyclohexane, xylenyl, methylcyclohexane, isophorone, and dicyclohexylmethane are preferable.

Moreover, in formulas (14) to (17), examples of preferable R² include: alkyl groups such as a methyl group, an ethyl group, a propyl group (each isomer), a butyl group (each isomer), a pentyl group (each isomer), a hexyl group (each isomer), a heptyl group (each isomer), an octyl group (each isomer), a nonyl group (each isomer), a decyl group (each isomer), an undecyl group (each isomer), and a dodecyl group (each isomer); cycloalkyl groups such as a cyclopentyl group, a cyclohexyl group, a cycloheptyl group, a cyclooctyl group, a cyclononyl group, and a cyclodecyl group; and aromatic groups such as a phenyl group, a methyl-phenyl group (each isomer), an ethyl-phenyl group (each isomer), a propyl-phenyl group (each isomer), a butyl-phenyl group (each isomer), a pentyl-phenyl group (each isomer), a hexyl-phenyl group (each isomer), a heptyl-phenyl group (each isomer), an octyl-phenyl group (each isomer), a nonyl-phenyl group (each isomer), a decyl-phenyl group (each isomer), a dodecyl-phenyl group (each isomer), a phenyl-phenyl group (each isomer), a phenoxy-phenyl group (each isomer), a cumyl-phenyl group (each isomer), a dimethyl-phenyl group (each isomer), a diethyl-phenyl group (each isomer), a dipropyl-phenyl group (each isomer), a dibutyl-phenyl group (each isomer), a dipentyl-phenyl group (each isomer), a dihexyl-phenyl group (each isomer), a diheptyl-phenyl group (each isomer), a diphenyl-phenyl group (each isomer), a diphenoxy-phenyl group (each isomer), a dicumyl-phenyl group (each isomer), a naphthyl group (each isomer), and a methyl-naphthyl group (each isomer).

Among these, an aromatic group in which the number of carbon atoms constituting R² is 6 to 12 is preferable because the N-substituted carbamic acid ester, the N-substituted-O-substituted thiocarbamic acid ester, the N-substituted-S-substituted thiocarbamic acid ester, or the N-substituted dithiocarbamic acid ester often has a low thermal decomposition temperature (i.e., is easily thermally decomposed) compared with the case where R² is an aliphatic group.

Examples of the N-substituted carbamic acid ester can include N,N'-hexanediyl-bis-carbamic acid diphenyl ester, N,N'-hexanediyl-bis-carbamic acid di(methylphenyl) ester (each isomer), N,N-hexanediyl-bis-carbamic acid di(ethylphenyl) ester (each isomer), N,N'-hexanediyl-bis-carbamic acid di(propylphenyl) ester (each isomer), N,N-hexanediyl-bis-carbamic acid di(butylphenyl) ester (each isomer), N,N'-hexanediyl-bis-carbamic acid di(pentylphenyl) ester (each isomer), diphenyl-4,4'-methylene-dicyclohexylcarbamate, di(methylphenyl)-4,4'-methylene-dicyclohexylcarbamate, di(ethylphenyl)-4,4'-methylene-dicyclohexylcarbamate, di(propylphenyl)-4,4'-methylene-dicyclohexylcarbamate (each isomer), di(butylphenyl)-4,4'-methylene-dicyclohexylcarbamate (each isomer), di(pentylphenyl)-4,4'-methylene-dicyclohexylcarbamate (each isomer), di(hexylphenyl)-4,4'-methylene-dicyclohexylcarbamate (each isomer), di(heptylphenyl)-4,4'-methylene-dicyclohexylcarbamate (each isomer), di(octylphenyl)-4,4'-methylene-dicyclohexylcarbamate (each isomer), 3-(phenoxycarbonylamino-methyl)-3,5,5-trimethylcyclohexylcarbamic acid phenyl ester, 3-(methylphenoxycarbonylamino-methyl)-3,5,5-trimethyl cyclohexylcar bamic acid (methylphenoxy) ester (each isomer), 3-(ethylphenoxycarbonylamino-methyl)-3,5,5-trimethylcyclohexylcarba mic acid (ethylphenyl) ester (each isomer), 3-(propylphenoxycarbonylamino-methyl)-3,5,5-trimethylcyclohexylcar bamic acid (propylphenyl) ester (each isomer), 3-(butylphenoxycarbonylamino-methyl)-3,5,5-trimethylcyclohexylcarba mic acid (butylphenyl) ester (each isomer), 3-(pentylphenoxycarbonylamino-methyl)-3,5,5-trimethylcyclohexylcarb amic acid (pentylphenyl) ester (each isomer), 3-(hexylphenoxycarbonylamino-methyl)-3,5,5-trimethylcyclohexylcarb amic acid (hexylphenyl) ester (each isomer), 3-(heptylphenoxycarbonylamino-methyl)-3,5,5-trimethylcyclohexylcarb amic acid (heptylphenyl) ester (each isomer), 3-(octylphenoxycarbonylamino-methyl)-3,5, 5-trimethylcyclohexylcarbamic acid (octylphenyl) ester (each isomer), toluene-dicarbamic acid diphenyl ester (each isomer), toluene-dicarbamic acid di(methylphenyl) ester (each isomer), toluene-dicarbamic acid di(ethylphenyl) ester (each isomer), toluene-dicarbamic acid di(propylphenyl) ester (each isomer), toluene-dicarbamic acid di(butylphenyl) ester (each isomer), toluene-dicarbamic acid di(pentylphenyl) ester (each isomer), toluene-dicarbamic acid di(hexylphenyl) ester (each isomer), toluene-dicarbamic acid di(heptylphenyl) ester (each isomer), toluene-dicarbamic acid di(octylphenyl) ester (each isomer), N,N-(4,4'-methanediyl-diphenyl)-biscarbamic acid diphenyl ester, N,N'-(4,4'-methanediyl-diphenyl)-biscarbamic acid di(methylphenyl) ester, N,N'-(4,4'-methanediyl-diphenyl)-biscarbamic acid di(ethylphenyl) ester, N,N'-(4,4'-methanediyl-diphenyl)-biscarbamic acid di(propylphenyl) ester, N,N'-(4,4'-methanediyl-diphenyl)-biscarbamic acid di(butylphenyl) ester, N,N'-(4,4'-methanediyl-diphenyl)-biscarbamic acid di(pentylphenyl) ester, N,N'-(4,4'-methanediyl-diphenyl)-biscarbamic acid di(hexylphenyl) ester, N,N-(4,4'-methanediyl-diphenyl)-biscarbamic acid di(heptylphenyl) ester, and N,N'-(4,4-methanediyl-diphenyl)-biscarbamic acid di(octylphenyl) ester (each isomer).

The N-substituted carbamic acid esters described above may be used alone (one kind) or may be used in combination of two or more kinds.

Examples of the N-substituted-O-substituted thiocarbamic acid ester can include N,N'-hexanediyl-bis-thiocarbamic acid di(O-phenyl) ester, N,N'-hexanediyl-bis-thiocarbamic acid di(O-methylphenyl) ester (each isomer), N,N-hexanediyl-bis-thiocarbamic acid di(O-ethylphenyl) ester (each isomer), N,N'-hexanediyl-bis-thiocarbamic acid di(O-propylphenyl) ester (each isomer), N,N'-hexanediyl-bis-thiocarbamic acid di(O-butylphenyl) ester (each isomer), N,N'-hexanediyl-bis-thiocarbamic acid di(O-pentylphenyl) ester (each isomer), di(O-phenyl)-4,4'-methylene-dicyclohexylthiocarbamate, di(O-methylphenyl)-4,4'-methylene-dicyclohexylthiocarbamate, di(O-ethylphenyl)-4,4'-methylene-dicyclohexylthiocarbamate, di(O-propylphenyl)-4,4'-methylene-dicyclohexylthiocarbamate (each isomer), di(O-butylphenyl)-4,4'-methylene-dicyclohexylthiocarbamate (each isomer), di(O-pentylphenyl)-4,4'-methylene-dicyclohexylthiocarbamate (each isomer), di(O-hexylphenyl)-4,4'-methylene-dicyclohexylthiocarbamate (each isomer), di(O-heptylphenyl)-4,4'-methylene-dicyclohexylthiocarbamate (each isomer), di(O-octylphenyl)-4,4'-methylene-dicyclohexylthiocarbamate (each isomer), 3-(phenoxythiocarbonylamino-methyl)-3,5,5-trimethylcyclohexylthiocarbamic acid (O-phenyl) ester, 3-(methylphenoxythiocarbonylamino-methyl)-3,5,5-trimethylcyclohexylthiocarbamic acid (O-methylphenyl) ester (each isomer), 3-(ethylphenoxythiocarbonylamino-methyl)-3,5,5-trimethylcyclohexylthiocarbamic acid (O-ethylphenyl) ester (each isomer), 3-(propylphenoxythiocarbonylamino-methyl)-3,5,5-trimethylcyclohexyl thiocarbamic acid (O-propylphenyl) ester (each isomer), 3-(butylphenoxythiocarbonylamino-methyl)-3,5,5-trimethylcyclohexylthiocarbamic acid (O-butylphenyl) ester (each isomer), 3-(pentylphenoxythiocarbonylamino-methyl)-3,5,5-trimethylcyclohexyl thiocarbamic acid (O-pentylphenyl) ester (each isomer), 3-(hexylphenoxythiocarbonylamino-methyl)-3,5,5-trimethylcyclohexylthiocarbamic acid (O-hexylphenyl) ester (each isomer), 3-(heptylphenoxythiocarbonylamino-methyl)-3,5,5-trimethylcyclohexyl thiocarbamic acid (O-heptylphenyl) ester (each isomer), 3-(octylphenoxythiocarbonylamino-methyl)-3,5,5-trimethylcyclohexylthiocarbamic acid (O-octylphenyl) ester (each isomer), toluene-bis-thiocarbamic acid di(O-phenyl) ester (each isomer), toluene-bis-thiocarbamic acid di(O-methylphenyl) ester (each isomer), toluene-bis-thiocarbamic acid di(O-ethylphenyl) ester (each isomer), toluene-bis-thiocarbamic acid di(O-propylphenyl) ester (each isomer), toluene-bis-thiocarbamic acid di(O-butylphenyl) ester (each isomer), toluene-bis-thiocarbamic acid di(O-pentylphenyl) ester (each isomer), toluene-bis-thiocarbamic acid di(O-hexylphenyl) ester (each isomer), toluene-bis-thiocarbamic acid di(O-heptylphenyl) ester (each isomer), toluene-bis-thiocarbamic acid di(O-octylphenyl) ester (each isomer), N,N'-(4,4'-methanediyl-diphenyl)-bis-thiocarbamic acid di(O-phenyl) ester, N,N'-(4,4'-methanediyl-diphenyl)-bis-thiocarbamic acid di(O-methylphenyl) ester, N,N'-(4,4'-methanediyl-diphenyl)-bis-thiocarbamic acid di(O-ethylphenyl) ester, N,N'-(4,4'-methanediyl-diphenyl)-bis-thiocarbamic acid di(O-propylphenyl) ester, N,N'-(4,4'-methanediyl-diphenyl)-bis-thiocarbamic acid di(butylphenyl) ester, N,N'-(4,4'-methanediyl-diphenyl)-bis-thiocarbamic acid di(O-pentylphenyl) ester, N,N'-(4,4'-methanediyl-diphenyl)-bis-thiocarbamic acid di(O-hexylphenyl) ester, N,N'-(4,4'-methanediyl-diphenyl)-bis-thiocarbamic acid di(O-heptylphenyl) ester, and N,N'-(4,4'-methanediyl-diphenyl)-bis-thiocarbamic acid di(O-octylphenyl) ester (each isomer).

The N-substituted-O-substituted thiocarbamic acid esters described above may be used alone (one kind) or may be used in combination of two or more kinds.

Examples of the N-substituted-S-substituted thiocarbamic acid ester can include N,N'-hexanediyl-bis-thiocarbamic acid di(S-phenyl) ester, N,N'-hexanediyl-bis-thiocarbamic acid di(S-methylphenyl) ester (each isomer), N,N-hexanediyl-bis-thiocarbamic acid di(S-ethylphenyl) ester (each isomer), N,N'-hexanediyl-bis-thiocarbamic acid di(S-propylphenyl) ester (each isomer), N,N'-hexanediyl-bis-thiocarbamic acid di(S-butylphenyl) ester (each isomer), N,N'-hexanediyl-bis-thiocarbamic acid di(S-pentylphenyl) ester (each isomer), di(S-phenyl)-4,4'-methylene-dicyclohexylthiocarbamate, di(S-methylphenyl)-4,4'-methylene-dicyclohexylthiocarbamate, di(S-ethylphenyl)-4,4'-methylene-dicyclohexylthiocarbamate, di(S-propylphenyl)-4,4'-methylene-dicyclohexylthiocarbamate (each isomer), di(S-butylphenyl)-4,4'-methylene-dicyclohexylthiocarbamate (each isomer), di(S-pentylphenyl)-4,4'-methylene-dicyclohexylthiocarbamate (each isomer), di(S-hexylphenyl)-4,4'-methylene-dicyclohexylthiocarbamate (each isomer), di(S-heptylphenyl)-4,4'-methylene-dicyclohexylthiocarbamate (each isomer), di(S-octylphenyl)-4,4'-methylene-dicyclohexylthiocarbamate (each isomer), 3-(phenoxythiocarbonylamino-methyl)-3,5,5-trimethylcyclohexylthiocarbamic acid (S-phenyl) ester, 3-(methylphenoxythiocarbonylamino-methyl)-3,5,5-trimethylcyclohexyithiocarbamic acid (S-methylphenyl) ester (each isomer), 3-(ethylphenoxythiocarbonylamino-methyl)-3,5,5-trimethylcyclohexylthiocarbamic acid (S-ethylphenyl) ester (each isomer), 3-(propylphenoxythiocarbonylamino-methyl)-3,5,5-trimethylcyclohexyl thiocarbamic acid (S-propylphenyl) ester (each isomer), 3-(butylphenoxythiocarbonylamino-methyl)-3,5,5-trimethylcyclohexylthiocarbamic acid (S-butylphenyl) ester (each isomer), 3-(pentylphenoxythiocarbonylamino-methyl)-3,5,5-trimethylcyclohexyl thiocarbamic acid (S-pentylphenyl) ester (each isomer), 3-(hexylphenoxythiocarbonylamino-methyl)-3,5,5-trimethylcyclohexyl hiocarbamic acid (S-hexylphenyl) ester (each isomer), 3-(heptylphenoxythiocarbonylamino-methyl)-3,5,5-trimethylcyclohexyl thiocarbamic acid (S-heptylphenyl) ester (each isomer), 3-(octylphenoxythiocarbonylamino-methyl)-3,5,5-trimethylcyclohexylthiocarbamic acid (S-octylphenyl) ester (each isomer), toluene-bis-thiocarbamic acid di(S-phenyl) ester (each isomer), toluene-bis-thiocarbamic acid di(S-methylphenyl) ester (each isomer), toluene-bis-thiocarbamic acid di(S-ethylphenyl) ester (each isomer), toluene-bis-thiocarbamic acid di(S-propylphenyl) ester (each isomer), toluene-bis-thiocarbamic acid di(S-butylphenyl) ester (each isomer), toluene-bis-thiocarbamic acid di(S-pentylphenyl) ester (each isomer), toluene-bis-thiocarbamic acid di(S-hexylphenyl) ester (each isomer), toluene-bis-thiocarbamic acid di(S-heptylphenyl) ester (each isomer), toluene-bis-thiocarbamic acid di(S-octylphenyl) ester (each isomer), N,N-(4,4'-methanediyl-diphenyl)-bis-thiocarbamic acid di(S-phenyl) ester, N,N'-(4,4'-methanediyl-diphenyl)-bis-thiocarbamic acid di(S-methylphenyl) ester, N,N-(4,4'-methanediyl-diphenyl)-bis-thiocarbamic acid di(S-ethylphenyl) ester, N,N'-(4,4'-methanediyl-diphenyl)-bis-thiocarbamic acid di(S-propylphenyl) ester, N,N'-(4,4'-methanediyl-diphenyl)-bis-thiocarbamic acid di(butylphenyl) ester, N,N'-(4,4'-methanediyl-diphenyl)-bis-thiocarbamic acid di(S-pentylphenyl) ester, N,N'-(4,4'-methanediyl-diphenyl)-bis-thiocarbamic acid di(S-hexylphenyl) ester, N,N'-(4,4'-methanediyl-diphenyl)-bis-thiocarbamic acid di(S-heptylphenyl) ester, and N,N'-(4,4'-methanediyl-diphenyl)-bis-thiocarbamic acid di(S-octylphenyl) ester (each isomer).

The N-substituted-S-substituted thiocarbamic acid esters described above may be used alone (one kind) or may be used in combination of two or more kinds.

Examples of the N-substituted dithiocarbamic acid ester can include N,N-hexanediyl-bis-dithiocarbamic acid diphenyl ester, N,N'-hexanediyl-bis-dithiocarbamic acid di(methylphenyl) ester (each isomer), N,N-hexanediyl-bis-dithiocarbamic acid di(ethylphenyl) ester (each isomer), N,N'-hexanediyl-bis-dithiocarbamic acid di(propylphenyl) ester (each isomer), N,N'-hexanediyl-bis-dithiocarbamic acid di(butylphenyl) ester (each isomer), N,N'-hexanediyl-bis-dithiocarbamic acid di(pentylphenyl) ester (each isomer), diphenyl-4,4'-methylene-dicyclohexyldithiocarbamate, di(methylphenyl)-4,4'-methylene-dicyclohexyldithiocarbamate, di(ethylphenyl)-4,4-methylene-dicyclohexyldithiocarbamate, di(propylphenyl)-4,4'-methylene-dicyclohexyldithiocarbamate (each isomer), di(butylphenyl)-4,4'-methylene-dicyclohexyldithiocarbamate (each isomer), di(pentylphenyl)-4,4'-methylene-dicyclohexyldithiocarbamate (each isomer), di(hexylphenyl)-4,4'-methylene-dicyclohexyldithiocarbamate (each isomer), di(heptylphenyl)-4,4'-methylene-dicyclohexyldithiocarbamate (each isomer), di(octylphenyl)-4,4'-methylene-dicyclohexyldithiocarbamate (each isomer), 3-(phenylsulfonylthiocarbonylamino-methyl)-3,5,5-trimethylcyclohexyl dithiocarbamic acid phenyl ester, 3-(methylphenyldithiocarbonylamino-methyl)-3,5,5-trimethylcyclohexy ldithiocarbamic acid (methylphenyl) ester (each isomer), 3-(ethylphenyldithiocarbonylamino-methyl)-3,5,5-trimethylcyclohexyld ithiocarbamic acid (ethylphenyl) ester (each isomer), 3-(propylphenyldithiocarbonylamino-methyl)-3,5,5-trimethylcyclohexyl dithiocarbamic acid (propylphenyl) ester (each isomer), 3-(butylphenyldithiocarbonylamino-methyl)-3,5,5-trimethylcyclohexyld ithiocarbamic acid (butylphenyl) ester (each isomer), 3-(pentylphenyldithiocarbonylamino-methyl)-3,5,5-trimethylcyclohexyl dithiocarbamic acid (pentylphenyl) ester (each isomer), 3-(hexylphenyldithiocarbonylamino-methyl)-3,5,5-trimethylcyclohexyl dithiocarbamic acid (hexylphenyl) ester (each isomer), 3-(heptylphenyldithiocarbonylamino-methyl)-3,5,5-trimethylcyclohexyl dithiocarbamic acid (heptylphenyl) ester (each isomer), 3-(octylphenyldithiocarbonylamino-methyl)-3,5,5-trimethylcyclohexyld ithiocarbamic acid (octylphenyl) ester (each isomer), toluene-bis-dithiocarbamic acid diphenyl ester (each isomer), toluene-bis-dithiocarbamic acid di(methylphenyl) ester (each isomer), toluene-bis-dithiocarbamic acid di(ethylphenyl) ester (each isomer), toluene-bis-dithiocarbamic acid di(propylphenyl) ester (each isomer), toluene-bis-dithiocarbamic acid di(butylphenyl) ester (each isomer), toluene-bis-dithiocarbamic acid di(pentylphenyl) ester (each isomer), toluene-bis-dithiocarbamic acid di(hexylphenyl) ester (each isomer), toluene-bis-dithiocarbamic acid di(heptylphenyl) ester (each isomer), toluene-bis-dithiocarbamic acid di(octylphenyl) ester (each isomer), N,N'-(4,4'-methanediyl-diphenyl)-bis-dithiocarbamic acid diphenyl ester, N,N'-(4,4'-methanediyl-diphenyl)-bis-dithiocarbamic acid di(methylphenyl) ester, N,N'-(4,4'-methanediyl-diphenyl)-bis-dithiocarbamic acid di(ethylphenyl) ester, N,N'-(4,4'-methanediyl-diphenyl)-bis-dithiocarbamic acid di(propylphenyl) ester, N,N'-(4,4'-methanediyl-diphenyl)-bis-dithiocarbamic acid di(butylphenyl) ester, N,N'-(4,4'-methanediyl-diphenyl)-bis-dithiocarbamic acid di(pentylphenyl) ester, N,N'-(4,4'-methanediyl-diphenyl)-bis-dithiocarbamic acid di(hexylphenyl) ester, N,N'-(4,4'-methanediyl-diphenyl)-bis-dithiocarbamic acid di(heptylphenyl) ester, and N,N'-(4,4'-methanediyl-diphenyl)-bis-dithiocarbamic acid di(octylphenyl) ester (each isomer).

The N-substituted dithiocarbamic acid esters described above may be used alone (one kind) or may be used in combination of two or more kinds.

Examples of the N-substituted carbamic acid halogenide can include N,N'-hexanediyl-bis-carbamic acid dichloride, N,N'-hexanediyl-bis-carbamic acid dibromide, dichloro-4,4'-methylene-dicyclohexylcarbamate, dibromo-4,4'-methylene-dicyclohexylcarbamate, 3-(chlorocarbonylamino-methyl)-3,5,5-trimethylcyclohexylcarbamic acid chloride, 3-(bromo carbonylamino-methyl)-3,5,5-trimethylcyclohexylcarbamic acid bromide, toluene-dicarbamic acid dichloride (each isomer), toluene-dicarbamic acid dibromide (each isomer), N,N'-(4,4'-methanediyl-diphenyl)-biscarbamic acid dichloride, and N,N'-(4,4'-methanediyl-diphenyl)-biscarbamic acid dibromide.

The N-substituted carbamic acid halogenides described above may be used alone (one kind) or may be used in combination of two or more kinds.

A method for producing these N-substituted carbamic acid esters, N-substituted-O-substituted thiocarbamic acid esters, N-substituted-S-substituted thiocarbamic acid esters, N-substituted dithiocarbamic acid esters, or N-substituted carbamic acid halogenides is not particularly limited, and one can use various methods known in the art.

Among these compounds described above, the N-substituted carbamic acid ester is very useful for a method for producing an isocyanate in which a reaction that forms an isocyanate by the thermal decomposition of the N-substituted carbamic acid ester does not employ phosgene, and is preferably used in the present embodiment because one can efficiently produce an isocyanate by using a method according to the present embodiment.

Examples of a preferable method for producing the N-substituted carbamic acid ester include a method based on the following Process (I) or Process (II):

Process (I): a process of producing an N-substituted carbamic acid ester by the reaction between a carbonic acid ester and an organic primary amine.

Process (II): a process of producing an N-substituted carbamic acid ester from urea, an organic primary amine, and a hydroxy compound.

Hereinafter, the method for producing the N-substituted carbamic acid ester by Process (I) or Process (II) will be described.

Process (I) will be described.

First, the compounds used will be described.

A compound represented by formula (19) is preferably used as the carbonic acid ester:

[Chemical Formula 18]

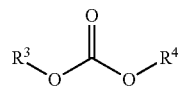

(19)

wherein $R^3$ and $R^4$ each independently represent one group selected from the group consisting of an aliphatic group having 1 to 22 carbon atoms and an aromatic group having 6 to 22 carbon atoms, and the aliphatic group having 1 to 22 carbon atoms or the aromatic group having 6 to 22 carbon atoms may contain an oxygen atom and/or a nitrogen atom.

In the case where $R^3$ and $R^4$ are an aliphatic group, one that is preferred as $R^3$ and $R^4$ in formula (19) is a linear or branched aliphatic hydrocarbon group having 1 to 20 carbon atoms, one that is more preferred is a linear or branched aliphatic hydrocarbon group having 1 to 8 carbon atoms, and one that is further preferred is a linear or branched alkyl group having 1 to 8 carbon atoms. Examples of such $R^3$ and $R^4$ include alkyl groups in which the number of carbon atoms constituting the group is 1 to 8, such as a methyl group, an ethyl group, a propyl group (each isomer), a butyl group (each isomer), a pentyl group (each isomer), a hexyl group (each isomer), a heptyl group (each isomer), and an octyl group (each isomer).

Examples of such a carbonic acid ester include dimethyl carbonate, diethyl carbonate, dipropyl carbonate (each isomer), dibutyl carbonate (each isomer), dipentyl carbonate (each isomer), dihexyl carbonate (each isomer), diheptyl carbonate (each isomer), and dioctyl carbonate (each isomer). Among them, a carbonic acid ester in which the number of carbon atoms constituting the alkyl group is an integer of 4 to 6 is preferably used.

In the case where $R^3$ and $R^4$ in formula (19) are an aromatic group, one that is preferred is an aromatic hydrocarbon group having 6 to 22 carbon atoms, and one that is more preferred is an aromatic hydrocarbon group having 6 to 14 carbon atoms. Although one can also use a carbonic acid ester wherein $R^3$ and $R^4$ are an aromatic hydrocarbon group having 23 or more carbon atoms, it is preferred that the number of carbon atoms constituting each of $R^3$ and $R^4$ should be 22 or less, from the viewpoint of facilitating separation from an isocyanate contained in a mixture described later.

Examples of the aromatic groups $R^3$ and $R^4$ include a phenyl group, a methylphenyl group (each isomer), an ethylphenyl group (each isomer), a propylphenyl group (each isomer), a butylphenyl group (each isomer), a pentylphenyl group (each isomer), a hexylphenyl group (each isomer), an octylphenyl group (each isomer), a nonylphenyl group (each isomer), a cumylphenyl group (each isomer), a dimethylphenyl group (each isomer), a methylethylphenyl group (each isomer), a methylpropylphenyl group (each isomer), a methylbutylphenyl group (each isomer), a methylpentylphenyl group (each isomer), a diethylphenyl group (each isomer), an ethylpropylphenyl group (each isomer), an ethylbutylphenyl group (each isomer), a dipropylphenyl group (each isomer), a dicumylphenyl group (each isomer), a trimethylphenyl group (each isomer), a triethylphenyl group (each isomer), and a naphthyl group (each isomer).

A method for producing the carbonic acid ester described above is not particularly limited, and one can use a method known in the art, examples of which include a method of reacting an organic tin compound having a tin-oxygen-carbon bond with carbon dioxide to produce a carbonic acid ester, and a method of reacting a carbonyl compound such as phosgene, carbodiimide, or carbonic acid ester with a hydroxy compound to produce it.

On the other hand, an organic primary amine represented by formula (20) is preferably used as the organic primary amine:

[Chemical Formula 19]

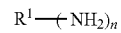

(20)

wherein $R^1$ has the same meaning as R' defined in formula (5); and n has the same meaning as n defined in formula (5).

An organic primary polyamine wherein n is 2 or more is preferably used as the organic primary amine represented by formula (20), and an organic primary diamine wherein n is 2 is more preferably used.

Examples of the organic primary amine as represented by formula (20) can include: aliphatic diamines such as hexamethylenediamine, 4,4'-methylenebis(cyclohexylamine) (each isomer), cyclohexanediamine (each isomer), and 3-aminomethyl-3,5,5-trimethylcyclohexylamine (each isomer); and aromatic diamines such as phenylenediamine (each isomer), toluenediamine (each isomer), and 4,4'-methylenedianiline. Among them, aliphatic diamines such as hexamethylenediamine, 4,4'-methylenebis(cyclohexylamine) (each isomer), cyclohexanediamine (each isomer), and 3-aminomethyl-3,5,5-trimethylcyclohexylamine (each isomer) are preferably used, and among them, hexamethylenediamine, 4,4'-methylenebis(cyclohexylamine) and 3-aminomethyl-3,5,5-trimethylcyclohexylamine are more preferable.

The reaction between the carbonic acid ester and the organic primary amine is preferably performed in the presence of a hydroxy compound.

As the hydroxy compound, one can use an alcohol or an aromatic hydroxy compound. A preferable alcohol is the alcohol described in formula (10), and a preferable aromatic hydroxy compound is the aromatic hydroxy compound described in formula (11).

Among these hydroxy compounds (alcohols and aromatic hydroxy compounds), a compound that corresponds to a compound $R^3OH$ in which a hydrogen atom is added to the group $R^3O$ ($R^3$ is a group defined in formula (19); and O represents an oxygen atom) constituting the carbonic acid ester is more preferably used. For example, methanol is preferably used as the hydroxy compound in the case where the carbonic acid ester is dimethyl carbonate, and phenol is preferably used as the hydroxy compound in the case where the carbonic acid ester is diphenyl carbonate. This is because of being able to reduce the types of compounds in a reaction mixture obtained by the reaction between the carbonic acid ester and the amine compound and being able to simplify separation procedures.

The organic primary amine is preferably supplied in a liquid state to a reactor that performs the production of the N-substituted carbamic acid ester. In general, the organic primary amine exemplified above is often one that is solid at room temperature (e.g., 20° C.), and in such a case, can also be supplied in a liquid state by heating the organic primary amine to a melting point or higher. However, since supplying the organic primary amine at too high a temperature may cause a side reaction such as a thermal denaturation reaction due to heating, it is preferred to prepare the organic primary amine into a mixture with the hydroxy compound, the carbonic acid ester, or water and supply it in a liquid state at a relatively low temperature.

The abundance ratio therebetween at which the carbonic acid ester reacts with the organic primary amine is generally in the range in which the carbonic acid ester is 1 to 1000 times in terms of a stoichiometric ratio with respect to the amino group of the organic primary amine, though differing depending on the compounds to be reacted. Although it is preferred that the carbonic acid ester should be used in an excessive amount with respect to the amino group of the organic primary amine for enhancing the reaction rate and completing the reaction early, one that is preferred is in the range of 1.1 to 50 times, and one that is more preferred is used in the range of 1.5 to 10 times, in consideration of the size of a reactor. In the case where a hydroxy compound is allowed to coexist in the reaction between the carbonic acid ester and the organic primary amine, the amount of the hydroxy compound used is preferably in the range of 1 to 100 times, more preferably 1.2 to 50 times, further preferably 1.5 to 10 times, in terms of a stoichiometric ratio with respect to the amino group of the organic primary amine. The reaction temperature is usually in the range of 0° C. to 150° C. High temperatures are preferable for enhancing the reaction rate, whereas unfavorable reaction may occur at high temperatures; thus one that is more preferred is in the range of 10° C. to 100° C. It is also acceptable to install a cooling apparatus or a heating apparatus known in the art in the reactor in order to keep the reaction temperature constant. Moreover, the reaction pressure may be any of reduced pressure, normal pressure, and increased pressure, though differing depending on the types of the compounds used or the reaction temperature; and one that is preferred is performed in the range of 20 to $1 \times 10^6$ Pa. There is no particular limitation to the reaction time (residence time in the case of the continuous method); and one that is preferred is 0.001 to 50 hours, one that is more preferred is 0.01 to 20 hours, and one that is further preferred is 0.1 to 10 hours. Moreover, one can also terminate the reaction by collecting the reaction solution and confirming, for example, by liquid chromatography, that the desired amount of the N-substituted carbamic acid ester is formed.

It is preferred not to use a catalyst in the reaction between the carbonic acid ester and the organic primary amine. This is because: a metal component used as a catalyst remains in products unless undergoing a step of separating the catalyst in forming the N-substituted carbamic acid ester by a catalytic reaction; and heating the N-substituted carbamic acid ester in which the catalytic component remains for a thermal decomposition reaction or the like may cause the thermal denaturation reaction or the like of the N-substituted carbamic acid ester. Although one can also perform the transport of reaction mixtures or a thermal decomposition reaction after using a catalyst in the reaction between the carbonic acid ester and the organic primary amine and passing a step of removing a catalyst, this approach is not preferable because the number of steps increases.

However, it is not denied that one uses a catalyst for the purpose of completing the reaction in a short time, lowering the reaction temperature, etc. In general, in the case of using an aromatic amine (e.g., in the case where in formula (20), $R^1$ is an aromatic group) as the organic primary amine, reactivity may be low compared with an aliphatic amine (e.g., in the case where in formula (20), $R^1$ is an aliphatic group); thus, use of the catalyst may be effective. Moreover, also in the case of using an aliphatic carbonic acid ester (e.g., in the case where in formula (19), $R^3$ and $R^4$ are an aliphatic group) as the carbonic acid ester, reactivity may be low compared with the case where the carbonic acid ester is an aromatic carbonic acid ester (e.g., in the case where in formula (19), $R^3$ and $R^4$ are an aromatic group); thus use of the catalyst may be effective. Examples of the catalyst include an organic metal compound or an inorganic metal compound such as tin, lead, copper, or titanium, and basic catalysts such as alcoholates of an alkali metal or an alkaline earth metal which include methylate, ethylate, and butyrate (each isomer) of lithium, sodium, potassium, calcium, or barium. As described above, in the case of using the catalyst, it is preferred to perform next step such as a thermal decomposition reaction after finishing the reaction between the carbonic acid ester and the organic primary amine and then passing the step of removing the catalyst. As a method for removing the catalyst, one can use a method known in the art such as crystallization, membrane separation, or separation using an ion-exchange resin or the like.

It is also acceptable, but not preferable, to use redundant carbonic acid esters or a reaction solvent other than the redundant carbonic acid esters and the hydroxy compound, because the separation or the like of the inactive solvent from an isocyanate or a hydroxy compound that forms by the thermal decomposition reaction of the N-substituted carbamic acid ester described later is complicated.

A tank reactor, a tower reactor, or a distillation column known in the art can be used as the reactor used in the reaction between the carbonic acid ester and the organic primary amine. Although materials for the reactor and lines may be any of those known in the art unless having adverse effects on starting materials or reactants, SUS304, SUS316, SUS316L, or the like is inexpensive and can be used preferably.

Next, Process (II) will be described.

The organic primary amine represented by formula (20) is preferably used as the organic primary amine used in this step.

Moreover, any of an alcohol and an aromatic hydroxy compound may be used as the hydroxy compound. A preferable hydroxy compound is the alcohol represented by formula (10) in the case where the hydroxy compound is an alcohol, and is the aromatic hydroxy compound represented by formula (11) in the case where the hydroxy compound is an aromatic hydroxy compound.

Although reaction conditions for the reaction of urea, the hydroxy compound, and the organic primary amine also differ depending on the compounds used, the amount of the hydroxy compound is in the range of 1 time to 500 times in terms of a stoichiometric ratio with respect to the amino group of the organic primary amine used. If the amount of the hydroxy compound used is small, complicatedly substituted carbonyl compounds or the like tend to form; thus, in consideration of the size of a reactor, one that is preferred is in the range of 1 time to 200 times, one that is more preferred is in the range of 1.5 times to 100 times, and one that is further preferred is 2 times to 50 times, though it is preferred to use a great excess of the hydroxy compound.

It is preferred that the amount of urea should be in the range of 1 time to 100 times in terms of a stoichiometric ratio with respect to the amino group of the organic primary amine. Also in the case where the amount of urea used is small, complicatedly substituted carbonyl compounds or the like tend to form; thus, it is preferred to use a great excess of urea. However, the case where complicatedly substituted carbonyl compounds tend to form rather occurs by using too excessive urea. Therefore, one that is more preferred is 1.1 times to 10 times, and one that is further preferred is in the range of 1.5 times to 5 times.

It is preferred that the reaction temperature should be in the range of 100° C. to 350° C., though depending on the reactivities of the organic primary amine, the urea, and the hydroxy compound used. A temperature lower than 100° C. is not preferable because the hydroxy compound strongly bonds to ammonia that forms as by-products and thus, reaction is slow or reaction hardly occurs, or because complicatedly substituted carbonyl compounds increase. On the other hand, a temperature higher than 350° C. is not preferable because the hydroxy compound is denatured by dehydrogenation or the decomposition reaction, denaturation reaction, or the like of an N-substituted carbamic acid ester, which is a product, tends to occur. From such a viewpoint, a more preferable temperature is in the range of 120° C. to 320° C., and one that is further preferred is in the range of 140° C. to 300° C.

Although the reaction pressure differs depending on the composition of the reaction system, the reaction temperature, a method for removing ammonia, a reaction apparatus, etc., and the reaction can be performed at reduced pressure, normal pressure, or increased pressure, it is preferred that it should be carried out in the range of 0.01 kPa to 10 MPa (absolute pressure). In consideration of ease of industrial practice, reduced pressure or normal pressure is preferable, and the range of 0.1 kPa to 1.5 MPa (absolute pressure) is preferable.

The reaction through which an N-substituted carbamic acid ester forms from the organic primary amine, urea, and the hydroxy compound is an equilibrium reaction, and the reaction greatly tilts toward the original system. Thus, for enhancing the yield of the N-substituted carbamic acid ester, it is required to perform the reaction while removing ammonia that forms as by-products, from the system as much as possible. One that is preferred is to remove ammonia such that an ammonia concentration in the reaction solution becomes 1000 ppm or lower, more preferably 300 ppm or lower, further preferably 100 ppm or lower, most preferably 10 ppm or lower.

As the method for removing ammonia, one can perform a reactive distillation method, a method based on an inert gas, a method based on membrane separation or adsorptive separation, or the like. For example, the reactive distillation method is a method of removing ammonia that successively forms under reaction, by distillation in a gas state. The method can also be performed under boiling of a solvent or a hydroxy compound in order to enhance the distillation efficiency of ammonia. Moreover, the method based on an inert gas is a method of removing, from the reaction system, ammonia that successively forms under reaction, by allowing it to be entrained in a gas state in an inert gas. A method of using, for example, nitrogen, helium, argon, carbonic acid gas, methane, ethane, and propane alone or by mixing as the inert gas to introduce the inert gas into the reaction system is preferable. Examples of adsorbents used in the method of doing adsorptive separation include adsorbents that may be used under temperature conditions where the reaction is carried out, such as silica, alumina, various types of zeolites, and diatomaceous earths. These methods for removing ammonia from the system may be carried out alone or may be carried out in combination of plural types of the methods.

In the reaction, one can use a catalyst, for example, for the purpose of enhancing the reaction rate. For example, basic catalysts such as methylate, ethylate, and butyrate (each isomer) of lithium, sodium, potassium, calcium, or barium, a simple substance of rare earth element, antimony, or bismuth and oxides, sulfides, and salts of these elements, a simple substance of boron and boron compounds, metals of the copper group, zinc group, aluminum group, carbon group, or titanium group in the periodic table and oxides and sulfides of these metals, and carbides and nitrides of elements of the carbon group except for carbon, titanium group, vanadium group, and chromium group in the periodic table are preferably used as such a catalyst. In the case of using the catalyst, its used amount is not particularly limited, and however, it can be used in the range of 0.0001 to 100 times in terms of a stoichiometric ratio with respect to the amino group of the organic primary amine. Since the case where adding the catalyst causes the need to remove the catalyst is frequent, one that is preferred is to perform it without adding the catalyst. In the case of using the catalyst, the catalyst may be removed after reaction. As a method for removing it, one can use a method known in the art, and a method such as membrane separation, distillation separation, or crystallization can be used preferably.

Although the reaction time (residence time in the case of continuous reaction) differs depending on the composition of the reaction system, the reaction temperature, the method for removing ammonia, a reaction apparatus, the reaction pressure, etc., one that is preferred is 0.01 to 100 hours. The reaction time can also be determined depending on the amount of formation of the N-substituted carbamic acid ester, which is the compound of interest. For example, it is also acceptable to terminate the reaction after sampling the reaction solution, quantifying the content of the N-substituted carbamic acid ester in the reaction solution, and confirming forming at a yield of 10% or more with respect to the organic primary amine used, or it is also acceptable to terminate the reaction after confirming that the yield is 90% or more. Preferably, the yield is 50% or more, more preferably 80% or more, further preferably 90% or more.

Although it is not necessarily required to use a reaction solvent in the reaction, one preferably uses, as the reaction solvent, an appropriate solvent for the purpose of facilitating the reaction procedures, etc., for example, alkanes such as pentane (each isomer), hexane (each isomer), heptane (each isomer), octane (each isomer), nonane (each isomer), and decane (each isomer); aromatic hydrocarbons and alkyl-substituted aromatic hydrocarbons such as benzene, toluene, xylene (each isomer), ethylbenzene, diisopropylbenzene (each isomer), dibutylbenzene (each isomer), and naphthalene; nitrile compounds such as acetonitrile and benzonitrile; aromatic compounds substituted by halogen or a nitro group, such as chlorobenzene, dichlorobenzene (each isomer), bromobenzene, dibromobenzene (each isomer), chloronaphthalene, bromonaphthalene, nitrobenzene, and nitronaphthalene; polycyclic hydrocarbon compounds such as diphenyl, substituted diphenyl, diphenylmethane, terphenyl, anthracene, and dibenzyltoluene (each isomer); aliphatic hydrocarbons such as cyclohexane, cyclopentane, cyclooctane, and ethylcyclohexane; ketones such as methyl ethyl ketone and acetophenone; esters such as dibutyl phthalate, dihexyl phthalate, dioctyl phthalate, and benzyl butyl phthalate; ethers and thioethers such as tetrahydrofuran, 1,4-dioxane, 1,2-dimethoxyethane, diphenyl ether, and diphenyl sulfide; ketone compounds such as acetone and methyl ethyl ketone; ester compounds such as ethyl acetate and ethyl benzoate; and sulfoxides such as dimethyl sulfoxide and diphenyl sulfoxide. Needless to say, the hydroxy compound used in an excessive amount in the reaction is also preferably used as a reaction solvent.

Moreover, as the method for producing an N-substituted carbamic acid ester by the reaction of urea, the hydroxy compound, and the organic primary amine, one can also use a method comprising the following Step (A) and Step (B):

Step (A): a step of reacting an organic primary amine with urea to obtain a reaction mixture containing a compound having an ureido group.

Step (B): a step of reacting the compound having an ureido group obtained in the Step (A) with a hydroxy compound to produce an N-substituted carbamic acid ester.

It is preferred that the amount of urea used in Step (A) should in the range of 1 time to 100 times in terms of a stoichiometric ratio with respect to the amino group of the organic primary amine. Also in the case where the amount of urea used is small, complicatedly substituted carbonyl compounds or the like tend to form; thus, it is preferred to use a great excess of urea. However, the case where complicatedly substituted urea compounds or carbonyl compounds tend to form rather occurs by using too excessive urea. Therefore, one that is more preferred is 1.1 times to 10 times, and one that is further preferred is in the range of 1.5 times to 5 times.

The reaction temperature in Step (A) can be carried out in the range of 30° C. to 250° C. High temperatures are preferable for enhancing the reaction rate, whereas unfavorable reaction may occur at high temperatures to form complicatedly substituted urea compounds or carbonyl compounds; thus one that is more preferred is 50° C. to 200° C., and one that is further preferred is in the range of 70° C. to 180° C. It is also acceptable to install a cooling apparatus or a heating apparatus known in the art in the reactor that performs Step (A) in order to keep the reaction temperature constant.

Although the reaction pressure in Step (A) differs depending on, the types of the compounds used, the composition of the reaction system, the reaction temperature, a reaction apparatus, etc., it is usually preferred that it should be carried out in the range of 0.01 kPa to 10 MPa (absolute pressure), and in consideration of ease of industrial practice, the range of 0.1 kPa to 5 MPa (absolute pressure) is preferable.

There is no particular limitation to the reaction time (residence time in the case of the continuous method) in Step (A); and one that is preferred is 0.001 to 100 hours, one that is more preferred is 0.01 to 80 hours, and one that is further preferred is 0.1 to 50 hours. Moreover, one can also terminate the reaction by collecting the reaction solution and confirming, for example, by liquid chromatography, that the compound having an ureido group is formed in the desired amount.

For carrying out the reaction of Step (A), one can use a catalyst, if necessary. The catalysts exemplified in the production of an N-substituted carbamic acid ester by the reaction of urea, the hydroxy compound, and the organic primary amine described above can be used as the catalyst. For the catalyst, it is preferred to remove it for the reason described above, also in Step (A). One that is more preferred is to remove it every completion of the step using the catalyst. The methods known in the art as described above can be used preferably as a method for removing it. Moreover, it is preferred to use a reaction solvent in Step (A), and one can use the reaction solvents exemplified in the production of an N-substituted carbamic acid ester by the reaction of urea, the hydroxy compound, and the organic primary amine described above, but preferably uses a hydroxy compound of the same kind as the hydroxy compound used in next Step (B), as the reaction solvent.

Although reaction conditions for producing an N-substituted carbamic acid ester by the reaction between the compound having an ureido group and the hydroxy compound in Step (B) also differ depending on the compounds to be reacted, it is preferred that the amount of the hydroxy compound should be in the range of 1 time to 500 times in terms of a stoichiometric ratio with respect to the number of ureido groups in the compound having an ureido group used. Complicatedly substituted carbonyl compounds or high-molecular-weight compounds having a carbonyl bond in the molecule tend to form by an amount less than 1 time; thus, in consideration of the size of a reactor, one that is more preferred is in the range of 1 time to 100 times, one that is further preferred is in the range of 2 times to 50 times, and one that is still further preferred is in the range of 3 to 20 times, though it is preferred to use a great excess of the hydroxy compound.

It is preferred that the reaction temperature in Step (B) should be in the range of 100° C. to 350° C., though depending on the compounds used. A temperature lower than 100° C. is not preferable because the hydroxy compound strongly bonds to ammonia that forms as by-products and thus, reaction is slow or reaction hardly occurs, or because complicatedly substituted carbonyl compounds increase. On the other hand, a temperature higher than 350° C. is not preferable because the hydroxy compound is denatured by dehydrogenation or the decomposition reaction, denaturation reaction, or the like of an N-substituted carbamic acid ester, which is a product, tends to occur. From such a viewpoint, a more preferable temperature is in the range of 120° C. to 320° C., and one that is further preferred is in the range of 140° C. to 300° C.

Although the reaction pressure in Step (B) differs depending on the composition of the reaction system, the reaction temperature, a method for removing ammonia, a reaction apparatus, etc., it is usually preferred that it should be carried out in the range of 0.01 Pa to 10 MPa (absolute pressure); and in consideration of ease of industrial practice, the range of 0.1 Pa to 5 MPa (absolute pressure) is more preferable, and in consideration of removing a gas of ammonia from the system, 0.1 Pa to 1.5 MPa (absolute pressure) is further preferable.

The reaction that forms an N-substituted carbamic acid ester in Step (B) is an equilibrium reaction, and the reaction tilts toward the original system; thus, it is preferred to perform the reaction while removing ammonia that forms as by-products, from the system as much as possible. One that is preferred is to remove ammonia such that an ammonia concentration in the reaction solution becomes 1000 ppm or lower, more preferably 300 ppm or lower, further preferably 100 ppm or lower, most preferably 10 ppm or lower. As the method therefor, one can perform a reactive distillation method, a method based on an inert gas, a method based on membrane separation or adsorptive separation, or the like. For example, the reactive distillation method is a method of removing ammonia that successively forms under reaction, by distillation in a gas state. The method can also be performed under boiling of a solvent or a hydroxy composition in order to enhance the distillation efficiency of ammonia. Moreover, the method based on an inert gas is a method of removing, from the reaction system, ammonia that successively forms under reaction, by allowing it to be entrained in a gas state in an inert gas. A method of using, for example, nitrogen, helium, argon, carbonic acid gas, methane, ethane, and propane alone or by mixing as the inert gas to introduce the inert gas into the reaction system is preferable. These methods for removing ammonia from the system may be carried out alone or may be carried out in combination of plural types of the methods.

In the reaction in Step (B), one can use a catalyst, for example, for the purpose of enhancing the reaction rate. The catalysts exemplified in the production of an N-substituted carbamic acid ester by the reaction of urea, the hydroxy compound, and the organic primary amine described above can be used as the catalyst. Moreover, although one can use a reaction solvent in Step (B) and can use the reaction solvents exemplified in the production of an N-substituted carbamic acid ester by the reaction of urea, the hydroxy compound, and the organic primary amine described above, one that is preferred is to use the hydroxy compound used in excess in the Step (B), as the reaction solvent.

A tank reactor, a tower reactor, or a distillation column known in the art can be used as the reactor used in the production of the N-substituted carbamic acid ester shown above. Although materials for the reactor and lines may be any of those known in the art unless having adverse effects on starting materials or reactants, SUS304, SUS316, SUS316L, or the like is inexpensive and can be used preferably.

Although the N-substituted carbamic acid ester produced by the methods described above (Process (I), Process (II), and Step (A) and Step (B)) are preferably used in the production of an isocyanate by the thermal decomposition of an N-substituted carbamic acid ester, an N-substituted carbamic acid ester more preferably used in the production of an isocyanate is an N-substituted carbamic acid-O-aryl ester in which the ester group is an aromatic group. An N-substituted carbamic acid ester produced using an aromatic carbonic acid ester (e.g., a carbonic acid ester wherein $R^3$ and $R^4$ in formula (6) are an aromatic group) as the carbonic acid ester of Process (I), and an N-substituted carbamic acid ester produced using an aromatic hydroxy compound as the hydroxy compound of Process (II) or Step (B) correspond to the N-substituted carbamic acid-O-aryl ester described above. On the other hand, an N-substituted carbamic acid ester produced using an aliphatic carbonic acid ester (e.g., a carbonic acid ester wherein $R^3$ and $R^4$ in formula (6) are an aliphatic group) as the carbonic acid ester of Process (I), and an N-substituted carbamic acid ester produced using an alcohol as the hydroxy compound of Process (II) or Step (B) are an N-substituted carbamic acid-O-aliphatic ester in which the ester group is an aliphatic group. The N-substituted carbamic acid-O-aliphatic ester tends to hardly cause a thermal decomposition reaction, compared with the N-substituted carbamic acid-O-aryl ester.

The N-substituted carbamic acid ester obtained by the production method described above can also be obtained as an N-substituted carbamic acid-O-aryl ester or can also be obtained as an N-substituted carbamic acid-O-aliphatic ester, depending on the types of the compounds used. In the case of obtaining the N-substituted carbamic acid-O-aliphatic ester by the production method described above, it can be converted by Step (Y) below to an N-substituted carbamic acid-O-aryl ester for which thermal decomposition is easy, and then used in a thermal decomposition reaction. Incidentally, the step is also referred to as a "transesterification step" in the present embodiment because of being a step of converting the ester group of the N-substituted carbamic acid-O-aliphatic ester.

Step (Y): a step of reacting an N-substituted carbamic acid-O-aliphatic ester with an aromatic hydroxy compound to produce an N-substituted carbamic acid-O-aryl ester having an ester group derived from the aromatic hydroxy compound.

Incidentally, an alcohol derived from the N-substituted carbamic acid-O-aliphatic ester forms in the Step (Y). Hereinafter, the Step (Y) will be described.

As the aromatic hydroxy compound to be reacted, one can use an aromatic hydroxy compound of the same kind as the aromatic hydroxy compound represented by formula (11). The aromatic hydroxy compounds described above may be used alone or in combination of plural types.

The Step (Y) can be performed by various methods according to the compounds used, etc., with reference to a method known in the art (see e.g., WO2008/059953).

Although reaction conditions for Step (Y) differ depending on the compounds to be reacted, it is preferred to use the aromatic hydroxy compound in the range of 2 to 1000 times indicated in stoichiometric ratio with respect to the ester group constituting the N-substituted carbamic acid-O-aliphatic ester as a raw material. For completing the reaction early, it is preferred that the aromatic hydroxy compound should be in an excessive amount with respect to the ester group constituting the N-substituted carbamic acid-O-aliphatic ester as a raw material; and in consideration of the size of a reactor, one that is more preferred is in the range of 2 to 100 times, and one that is further preferred is in the range of 5 to 50 times.

The reaction temperature is preferably in the range of 100° C. to 300° C., and high temperatures are preferable for enhancing the reaction rate, whereas a side reaction may tend to occur at high temperatures; thus one that is more preferred is in the range of 150° C. to 250° C. It is also acceptable to install a cooling apparatus or a heating apparatus known in the art in the reactor in order to keep the reaction temperature constant. Moreover, the reaction pressure may be any of reduced pressure, normal pressure, and increased pressure, though differing depending on the types of the compounds used or the reaction temperature; and one that is preferred is performed in the range of 20 to $1\times10^6$ Pa. There is no particular limitation to the reaction time (residence time in the case of the continuous method); and one that is preferred is 0.001 to 100 hours, one that is more preferred is 0.01 to 50 hours, and one that is further preferred is 0.1 to 30 hours. Moreover, one can also terminate the reaction by collecting the reaction solution and confirming, for example, by liquid chromatography, that the N-substituted carbamic acid-O-aryl ester of interest is formed in the desired amount.

Although a catalyst is not necessarily required for the Step (Y), there is no problem in using the catalyst in order to lower the reaction temperature or complete the reaction early. The catalyst is used at preferably 0.01 to 30 wt %, more preferably 0.5 to 20 wt %, with respect to the weight of the N-substituted carbamic acid-O-aliphatic ester. Examples of the catalyst include Lewis acids and transition metal compounds that form Lewis acids, organic tin compounds, compounds of metals of the copper group, zinc, and metals of the iron group, and amines. Examples thereof specifically include: Lewis acids and transition metal compounds that form Lewis acids, represented by $AlX_3$, $TiX_3$, $TiX_4$, $VOX_3$, $VX_5$, $ZnX_2$, $FeX_3$, or $SnX_4$ (wherein X is halogen, an acetoxy group, an alkoxy group, or an aryloxy group); organic tin compounds represented by $(CH_3)_3SnO$-

COCH$_3$, (C$_2$H$_5$)SnOCOC$_6$H$_5$, Bu$_3$SnOCOCH$_3$, Ph$_3$SnOCOCH$_3$, Bu$_2$Sn(OCOCH$_3$)$_2$, Bu$_2$Sn(OCOC$_{11}$H$_{23}$)$_2$, Ph$_3$SnOCH$_3$, (C$_2$H$_5$)$_3$SnOPh, Bu$_2$Sn(OCH$_3$)$_2$, Bu$_2$Sn(OC$_2$H$_5$)$_2$, Bu$_2$Sn(OPh)$_2$, Ph$_2$Sn(CH$_3$)$_2$, (C$_2$H$_5$)$_3$SnOH, PhSnOH, Bu$_2$SnO, (C$_8$H$_{17}$)$_2$SnO, Bu$_2$SnCl$_2$, or BuSnO(OH); compounds of metals of the copper group such as CuCl, CuCl$_2$, CuBr, CuBr$_2$, CuI, CuI$_2$, Cu(OAc)$_2$, Cu(acac)$_2$, copper oleate, Bu$_2$Cu, (CH$_3$O)$_2$Cu, AgNO$_3$, AgBr, silver picrate, and AgC$_6$H$_6$ClO$_4$; compounds of zinc such as Zn(acac)$_2$; and compounds of metals of the iron group such as Fe(C$_{10}$H$_8$)(CO)$_5$, Fe(CO)$_5$, Fe(C$_4$H$_6$)(CO)$_3$, Co(mesitylene)$_2$(PEt$_2$Ph$_2$), CoC$_5$F$_5$(CO)$_7$, and ferrocene. (In the description above, Bu represents a butyl group; Ph represents a phenyl group; and acac represents an acetylacetone chelate ligand.), amines such as 1,4-diazabicyclo[2,2,2]octane, triethylenediamine, and triethylamine are suitable for use, and among them, examples thereof include organic metal catalysts such as dibutyltin dilaurate, lead octoate, and stannous octoate. These compounds may be used alone or as a mixture of two types or more.

Although it is not necessarily required to use a reaction solvent in the present embodiment, one can use an inactive solvent appropriate for the purpose of facilitating the reaction procedures, etc. As the inactive solvent, one can use, for example, alkanes such as hexane (each isomer), heptane (each isomer), octane (each isomer), nonane (each isomer), and decane (each isomer); aromatic hydrocarbons and alkyl-substituted aromatic hydrocarbons such as benzene, toluene, xylene (each isomer), ethylbenzene, diisopropylbenzene (each isomer), dibutylbenzene (each isomer), and naphthalene; aromatic compounds substituted by halogen or a nitro group, such as chlorobenzene, dichlorobenzene (each isomer), bromobenzene, dibromobenzene (each isomer), chloronaphthalene, bromonaphthalene, nitrobenzene, and nitronaphthalene; polycyclic hydrocarbon compounds such as diphenyl, substituted diphenyl, diphenylmethane, terphenyl, anthracene, and dibenzyltoluene (each isomer); aliphatic hydrocarbons such as cyclohexane, cyclopentane, cyclooctane, and ethylcyclohexane; ketones such as methyl ethyl ketone and acetophenone; esters such as dibutyl phthalate, dihexyl phthalate, dioctyl phthalate, and benzyl butyl phthalate; ethers and thioethers such as diphenyl ether and diphenyl sulfide; sulfoxides such as dimethyl sulfoxide and diphenyl sulfoxide; and silicone oil. These solvents can be used alone or as a mixture of two types or more.

The reaction of transesterification in the present embodiment is an equilibrium reaction. Thus, for efficiently performing transesterification, it is preferred to pursue the reaction while removing an alcohol (alcohol derived from the N-substituted carbamic acid-O-aliphatic ester as a raw material) which is a product, from the reaction system. Thus, the removal of the product from the reaction system is easy by selecting the aromatic hydroxy compound such that the normal boiling point of the aromatic hydroxy compound used in transesterification becomes higher than the normal boiling point of the alcohol derived from the N-substituted carbamic acid-O-aliphatic ester as a raw material, because a compound having the lowest normal boiling point in the reaction system is the alcohol derived from the N-substituted carbamic acid-O-aliphatic ester as a raw material.

Moreover, for allowing transesterification to efficiently proceed, one that is preferred is to perform the transesterification by a continuous method. Specifically, one performs the transesterification by continuously supplying the N-substituted carbamic acid-O-aliphatic ester as a raw material and the aromatic hydroxy compound to a reactor. Then, one takes alcohol products derived from the N-substituted carbamic acid-O-aliphatic ester as a raw material, out of the reactor as gas components, and continuously takes a reaction solution containing an N-substituted carbamic acid-O-aryl ester that forms and the aromatic hydroxy compound, out of the bottom of the reactor.

Although materials for the reactor that forms transesterification and lines may be any of those known in the art unless having adverse effects on starting materials or reactants, SUS304, SUS316, SUS316L, or the like is inexpensive and can be used preferably. There is no particular limitation to the form of the reactor, and a reactor in a tank form or tower form known in the art can be used. For example, various methods known in the art such as a style using a reactor containing any of a stirred tank, a multi-stage stirred tank, a distillation column, a multi-stage distillation column, a multi-tube reactor, a continuous multi-stage distillation column, a packed column, a thin-film evaporator, a reactor having a support in the inside, a forced circulation reactor, a falling film evaporator, a falling drop evaporator, a trickle-bed reactor, and a bubble column, and a style combining these, are used. A method using a thin-film evaporator and/or a reactor in a column form is preferable from the viewpoint of efficiently shifting equilibrium toward the product side, and a structure having a large area of gas-liquid contact is preferable from the viewpoint of rapidly moving alcohol products derived from the N-substituted carbamic acid-O-aliphatic ester as a raw material, to the gas phase.

The multi-stage distillation column that can be used in the transesterification reaction may be any one that is a distillation column having multiple plates in which the number of theoretical plates in distillation is two or more and continuous distillation is possible. As such a multi-stage distillation column, one can use, for example, any one that is usually used as a multi-stage distillation column, such as a plate column system using trays such as bubble cap trays, porous plate trays, valve trays, or countercurrent trays, and a packed column style filled with various types of packing materials such as Raschig ring, Lessing ring, Pall ring, Berl Saddle, Interlock saddle, Dixon packing, McMahon packing, HELI-PACK, Sulzer packing, and Mellapak. As the packed column, one can use any one that is a packed column filled with the above-described packing materials known in the art within the column. Furthermore, one having a plate-packed mixed column style having both of plate parts and parts filled with packing materials is also preferably used.

It is also acceptable to additionally attach, to the reactor, lines that supply an inert gas and/or an inactive solvent in a liquid state from beneath the reactor. Moreover, in the case where the mixed solution containing the N-substituted carbamic acid-O-aryl ester of interest and the aromatic hydroxy compound contains the N-substituted carbamic acid-O-aliphatic ester as a raw material, it is also acceptable to attach, to the reactor, a line that circulates again a portion or the whole of the mixed solution to the reactor. Incidentally, in the case of using the inactive solvent, the inactive solvent may be in a gas state and/or liquid state.

Gas components containing the alcohol derived from the N-substituted carbamic acid-O-aliphatic ester as a raw material, which have been extracted from the reactor, can be purified preferably using a method known in the art such as a distillation column and reused as the alcohol of Process (I) and/or Process (II) and/or Step (A) and/or Step (B).

<Thermal Decomposition Reaction>

The mixture containing the active hydrogen-containing compound (A) and the compound (B) that reversibly reacts with the active hydrogen-containing compound, used in the present embodiment is preferably a mixture obtained by subjecting the N-substituted carbamic acid ester, the N-substituted-O-substituted thiocarbamic acid ester, the N-substituted-S-substituted thiocarbamic acid ester, the N-substituted dithiocarbamic acid ester, or the N-substituted carbamic acid halogenide described above to a thermal decomposition reaction. Since the procedure of subjecting it to a thermal decomposition reaction is the same among the compounds, hereinafter, the thermal decomposition reactions of these compounds described above will be described by taking the thermal decomposition reaction of the N-substituted carbamic acid ester as an example. Although an isocyanate and a hydroxy compound form in the thermal decomposition reaction of the N-substituted carbamic acid ester, it is only required to replace the isocyanate by a corresponding isothiocyanate in the case of the thermal decomposition reaction of the N-substituted-O-substituted thiocarbamic acid ester; it is only required to replace the hydroxy compound by a corresponding thiol or aromatic thiol in the case of the thermal decomposition reaction of the N-substituted-S-substituted thiocarbamic acid ester; it is only required to replace the isocyanate by a corresponding isothiocyanate and the hydroxy compound by a corresponding thiol or aromatic thiol in the case of the thermal decomposition reaction of the N-substituted dithiocarbamic acid ester; and it is only required to replace the hydroxy compound by a hydrogen halide in the case of the thermal decomposition reaction of the N-substituted carbamic acid halogenide.

<Thermal Decomposition of N-substituted Carbamic Acid Ester>

The mixture containing an isocyanate and a hydroxy compound in the present embodiment is preferably a mixture containing an isocyanate and a hydroxy compound that form by the thermal decomposition reaction of an N-substituted carbamic acid ester. In this context, a step of subjecting an N-substituted carbamic acid ester to a thermal decomposition reaction to produce a mixture containing an isocyanate and a hydroxy compound will be described.

Although it is acceptable to use or not to use a solvent in this step, one that is preferred is to carry out it in the presence of a hydroxy compound. As described above, preferably, a hydroxy compound is used in the production of the N-substituted carbamic acid ester, and one can use this hydroxy compound, as it is, as the hydroxy compound in this step. Moreover, since a hydroxy compound forms as reaction by-products in the method for producing an N-substituted carbamic acid ester by the reaction between the carbonic acid ester and the organic primary amine, one can use this hydroxy compound, as it is, as the hydroxy compound in this step. It is also acceptable to carry out this step by adjusting the amount of the hydroxy compound or newly preparing and using a hydroxy compound, if necessary.

Adjusting the amount of the hydroxy compound or newly preparing and using a hydroxy compound is described above, and the amount is preferably 0.2 to 50 times, more preferably 0.3 to 30 times, further preferably 1 to 20 times, in terms of the value of the number of moles of the hydroxy compound with respect to the value of the total number of ester groups contained in the N-substituted carbamic acid ester in consideration of the transport efficiency of the N-substituted carbamic acid ester or the size of a reservoir for storage.

Examples of the other solvents that may be added include inactive solvents appropriate for the purpose of facilitating the reaction procedures, etc., for example, alkanes such as hexane (each isomer), heptane (each isomer), octane (each isomer), nonane (each isomer), and decane (each isomer); aromatic hydrocarbons and alkyl-substituted aromatic hydrocarbons such as benzene, toluene, xylene (each isomer), ethylbenzene, diisopropylbenzene (each isomer), dibutylbenzene (each isomer), and naphthalene; aromatic compounds substituted by halogen or a nitro group, such as chlorobenzene, dichlorobenzene (each isomer), bromobenzene, dibromobenzene (each isomer), chloronaphthalene, bromonaphthalene, nitrobenzene, and nitronaphthalene; polycyclic hydrocarbon compounds such as diphenyl, substituted diphenyl, diphenylmethane, terphenyl, anthracene, and dibenzyltoluene (each isomer); aliphatic hydrocarbons such as cyclohexane, cyclopentane, cyclooctane, and ethylcyclohexane; ketones such as methyl ethyl ketone and acetophenone; and dibutyl phthalate, dihexyl phthalate, and dioctyl phthalate.

The reaction temperature of the thermal decomposition reaction is preferably in the range of 100° C. to 350° C., and high temperatures are preferable for enhancing the reaction rate. However, at high temperatures, the side reaction as described above may be caused by the N-substituted carbamic acid ester and/or the isocyanate which is a product; thus, one that is more preferred is in the range of 150° C. to 250° C. It is also acceptable to install a cooling apparatus or a heating apparatus known in the art in the reactor in order to keep the reaction temperature constant. Moreover, the reaction pressure may be any of reduced pressure, normal pressure, and increased pressure, though differing depending on the types of the compounds used or the reaction temperature; and one that is preferred is performed in the range of 20 to $1 \times 10^6$ Pa. There is no particular limitation to the reaction time (residence time in the case of the continuous method); and one that is preferred is 0.001 to 100 hours, one that is more preferred is 0.005 to 50 hours, and one that is further preferred is 0.01 to 10 hours.

In the present embodiment, one that is preferred is not to use a catalyst. However, in the case of using a catalyst in any step for producing the N-substituted carbamic acid ester, residues or the like of the catalyst may be supplied to the thermal decomposition step. In the present embodiment, it does not matter if such catalyst residues or the like are present.

In the case where the N-substituted carbamic acid ester is kept under high temperature for a long time, a side reaction such as a reaction that forms a urea bond-containing compound through a carbonic acid ester removal reaction from, for example, 2 molecules of the N-substituted carbamic acid ester, or a reaction that forms an allophanate group through a reaction with an isocyanate group that forms by the thermal decomposition of the N-substituted carbamic acid ester, may be caused. Thus, it is preferred that the time when the N-substituted carbamic acid ester and the isocyanate are kept under high temperature should be as short as possible. Thus, the thermal decomposition reaction is preferably performed by a continuous method. The continuous method is a method of continuously supplying a mixture containing the N-substituted carbamic acid ester to a reactor, subjecting it to a thermal decomposition reaction, and continuously extracting an isocyanate and a hydroxy compound that form, from the thermal decomposition reactor. In the continuous method, low-boiling-point components that form by the thermal decomposition reaction of the N-substituted carbamic acid ester are preferably collected as gas-phase components from the thermal decomposition reactor, while the remaining portions are collected as liquid-phase components from the bottom of the thermal decomposition reactor. Although one can also collect all compounds present in the thermal decomposition reactor as gas-phase components, the effect of dissolving compounds that form in a polymer form due to the side reaction caused by the N-substituted carbamic acid ester and/or the isocyanate, to thereby prevent the adhesion/accumulation of the compounds in a polymer form to the thermal decomposition reactor is obtained by allowing liquid-phase components to exist in the thermal decomposition reactor. Since an isocyanate and a hydroxy compound form by the thermal decomposition reaction of the N-substituted carbamic acid ester, one collects at least one compound of these compounds, as gas-phase components. Which compound is collected as gas-phase components depends on thermal decomposition reaction conditions, etc.

In this context, the term "low-boiling-point components that form by the thermal decomposition reaction of the N-substituted carbamic acid ester" used in the present embodiment particularly refers to compounds capable of existing as a gas under conditions where the thermal decomposition reaction is carried out, though the hydroxy compound and/or the isocyanate that form by the thermal decomposition reaction of the N-substituted carbamic acid ester correspond thereto.

For example, one can adopt a method of collecting, as gas-phase components, the isocyanate and the hydroxy compound that form by the thermal decomposition reaction, and collecting liquid-phase components containing the N-substituted carbamic acid ester. In the method, it is also acceptable to separately collect the isocyanate and the hydroxy compound in the thermal decomposition reactor.

In the case where the liquid-phase components contain the N-substituted carbamic acid ester, one that is preferred is to supply a portion or the whole of the liquid-phase components to the upper part of the thermal decomposition reactor and subject again the N-substituted carbamic acid ester to a thermal decomposition reaction. The upper part of the thermal decomposition reactor referred to herein refers to, for example, a plate equal to or above two plates from the bottom of the column in terms of the number of theoretical plates in the case where the thermal decomposition reactor is a distillation column, and refers to a part above a heat transfer area part under heat in the case where the thermal decomposition reactor is a thin-film evaporator. For supplying a portion or the whole of the liquid-phase components to the upper part of the thermal decomposition reactor, one that is preferred is to transport the liquid-phase components with them kept at 50° C. to 280° C., more preferably 70° C. to 230° C., further preferably 100° C. to 200° C.

Moreover, one can adopt, for example, a method of collecting, as gas-phase components, the isocyanate and the hydroxy compound that form by the thermal decomposition reaction, and collecting liquid-phase components containing the N-substituted carbamic acid ester from the bottom of the thermal decomposition reactor. In this method as well, the collected gas components containing the isocyanate are preferably supplied in the gas phase to a distillation apparatus for purifying/separating the isocyanate. On the other hand, liquid-phase components (a portion or the whole thereof) containing the N-substituted carbamic acid ester are supplied to the upper part of the thermal decomposition reactor to subject again the N-substituted carbamic acid ester to a thermal decomposition reaction. For supplying a portion or the whole of the liquid-phase components to the upper part of the thermal decomposition reactor, one that is preferred is to transport the liquid-phase components with them kept at 50° C. to 180° C., more preferably 70° C. to 170° C., further preferably 100° C. to 150° C.

Furthermore, one can adopt, for example, a method of collecting, of the isocyanate and the hydroxy compound that form by the thermal decomposition reaction, the hydroxy compound as gas-phase components, and collecting a mixture containing the isocyanate as liquid-phase components from the bottom of the thermal decomposition reactor. In this case, one supplies the liquid-phase components to a distillation apparatus to collect the isocyanate. In the case where the N-substituted carbamic acid ester is contained in the liquid-phase components, it is preferred that the mixture (a portion or the whole thereof) containing the N-substituted carbamic acid ester should be supplied to the upper part of the thermal decomposition reactor to subject again the N-substituted carbamic acid ester to a thermal decomposition reaction. For supplying a portion or the whole of the liquid-phase components to the upper part of the thermal decomposition reactor, one that is preferred is to transport the liquid-phase components with them kept at 50° C. to 180° C., more preferably 70° C. to 170° C., further preferably 100° C. to 150° C.

As also described above, in the thermal decomposition reaction, it is preferred to collect the liquid-phase components from the bottom of the thermal decomposition reactor. This is because of being able to dissolve by-products that form in a polymer form due to the side reaction, as described above, caused by the N-substituted carbamic acid ester and/or the isocyanate, and discharge them as liquid-phase components from the thermal decomposition reactor by allowing the liquid-phase components to exist in the thermal decomposition reactor. By this, the effect of reducing the adhesion/accumulation of the compounds in a polymer form to the thermal decomposition reactor is obtained.

In the case where the N-substituted carbamic acid ester is contained in the liquid-phase components, the by-products in a polymer form may accumulate in the liquid-phase components by repeating the step of supplying a portion or the whole of the liquid-phase components to the upper part of the thermal decomposition reactor to subject again the N-substituted carbamic acid ester to a thermal decomposition reaction. In this case, one can remove a portion or the whole of the liquid-phase components from the reaction system to thereby reduce the accumulation of the by-products in a polymer form or keep it at a constant concentration.

Although there is no particular limitation to the form of the thermal decomposition reactor, one that is preferred is to use a distillation apparatus known in the art in order to efficiently collect gas-phase components. For example, various methods known in the art such as a style using a reactor containing any of a distillation column, a multi-stage distillation column, a multi-tube reactor, a continuous multi-stage distillation column, a packed column, a thin-film evaporator, a reactor having a support in the inside, a forced circulation reactor, a falling film evaporator, and a falling drop evaporator, and a style combining these, are used. From the viewpoint of rapidly removing low-boiling-point components from the reaction system, one that is preferred is a tube-shaped reactor, and one that is more preferred is a method using a reactor such as a tube-shaped thin-film evaporator or a tube-shaped falling film evaporator; and a structure having a large area of gas-liquid contact that can rapidly move the low-boiling-point components that form, to the gas phase is preferable.

Although materials for the thermal decomposition reactor and lines may be any of those known in the art unless having adverse effects on the N-substituted carbamic acid ester, the aromatic hydroxy compound and the isocyanate which are products, etc., SUS304, SUS316, SUS316L, or the like is inexpensive and can be used preferably.

<Intermediate-boiling-point Inactive Compound>

Next, the intermediate-boiling-point inactive compound used in the present embodiment will be described.

The term "intermediate-boiling-point inactive compound" used herein refers to an intermediate-boiling-point inactive compound (C) in a method for separating, with a multi-stage distillation column, a mixture containing an active hydrogen-containing compound (A) and a compound (B) that reversibly reacts with the active hydrogen-containing compound (A), the method comprising distillation-separating the active hydrogen-containing compound (A) and the compound (B) with the multi-stage distillation column in the presence of an intermediate-boiling-point inactive compound (C) that has a normal boiling point between a normal boiling point of the active hydrogen-containing compound (A) and a normal boiling point of the compound (B) and is chemically inactive for both of the active hydrogen-containing compound (A) and the compound (B).

First, examples of a feature of the intermediate-boiling-point inactive compound (C) include the point where it is inactive for the active hydrogen-containing compound (A) and the compound (B) that reversibly reacts with the active hydrogen-containing compound. The "inactive" means not having reactivity with (A) and (B). The intermediate-boiling-point inactive compound (C) is a compound that does not form a covalent bond with each of or separately with (A) and (B) at the operation temperature of the distillation.

A preferable intermediate-boiling-point compound is a compound that does not have a functional group reactive with the isocyanate and the hydroxy compound, and one that is more preferred is a compound that does not have active hydrogen.

Examples of such an intermediate-boiling-point inactive compound (C) can include at least one kind of compound selected from the group consisting of (1) hydrocarbon compounds having a linear, branched, or cyclic structure; (2) compounds in which hydrocarbon compounds of the same kind or different kind having a linear, branched, or cyclic structure are bonded via an ether bond or a thioether bond (i.e., compounds in which two hydrocarbon compounds are bonded via an ether bond or a thioether bond; the hydrocarbon compounds have a linear, branched, or cyclic structure, and the two hydrocarbon compounds may be of the same kind or may be of different kind); (3) aromatic hydrocarbon compounds that may have a substituent comprising a hydrocarbon group; (4) compounds in which aromatic hydrocarbon compounds of the same kind or different kind are bonded via an ether bond or a thioether bond; (5) compounds in which a hydrocarbon compound having a linear, branched, or cyclic structure is bonded to an aromatic hydrocarbon compound via an ether bond or a thioether bond; and (6) halides in which at least one hydrogen atom constituting a hydrocarbon compound having a linear, branched, or cyclic structure, or at least one hydrogen atom constituting an aromatic hydrocarbon compound that may have a substituent comprising a hydrocarbon group is substituted by a halogen atom.

Specific examples of the intermediate-boiling-point inactive compound can include: hydrocarbon compounds such as pentane (each isomer), hexane (each isomer), heptane (each isomer), octane (each isomer), nonane (each isomer), decane (each isomer), dodecane (each isomer), tetradecane (each isomer), pentadecane (each isomer), hexadecane (each isomer), octadecane (each isomer), and nonadecane (each isomer); ethers to which a hydrocarbon compound is bonded via an ether bond, such as octyl ether (each isomer), nonyl ether (each isomer), decyl ether (each isomer), dodecyl ether (each isomer), tetradecyl ether (each isomer), pentadecyl ether (each isomer), hexadecyl ether (each isomer), octadecyl ether (each isomer), nonadecyl ether (each isomer), and tetraethylene glycol dimethyl ether; thioethers to which a hydrocarbon compound is bonded via a thioether bond, such as dimethyl sulfide, diethyl sulfide, dibutyl sulfide (each isomer), dihexyl sulfide (each isomer), octyl sulfide (each isomer), nonyl sulfide (each isomer), decyl sulfide (each isomer), dodecyl sulfide (each isomer), tetradecyl sulfide (each isomer), pentadecyl sulfide (each isomer), hexadecyl sulfide (each isomer), octadecyl sulfide (each isomer), and nonadecyl sulfide (each isomer); aromatic hydrocarbon compounds such as benzene, toluene, ethylbenzene, butylbenzene (each isomer), pentylbenzene (each isomer), hexylbenzene (each isomer), octylbenzene (each isomer), biphenyl, terphenyl, diphenylethane (each isomer), (methylphenyl)phenylethane (each isomer), dimethylbiphenyl (each isomer), and benzyltoluene (each isomer); aromatic ethers to which an aromatic hydrocarbon compound is bonded via an ether bond, such as diphenyl ether, di(methylbenzyl)ether (each isomer), di(ethylbenzyl)ether (each isomer), di(butylbenzyl)ether (each isomer), di(pentylbenzyl)ether (each isomer), di(hexylbenzyl)ether (each isomer), di(octylbenzyl)ether (each isomer), diphenyl ether, and dibenzyl ether; aromatic thioethers to which an aromatic hydrocarbon compound is bonded via a thioether bond, such as diphenyl sulfide, di(methylbenzyl) sulfide (each isomer), di(ethylbenzyl) sulfide (each isomer), di(butylbenzyl) sulfide (each isomer), di(pentylbenzyl) sulfide (each isomer), di(hexylbenzyl) sulfide (each isomer), di(octylbenzyl) sulfide (each isomer), di(methylphenyl) sulfide, and dibenzyl sulfide; compounds in which a hydrocarbon compound is bonded to an aromatic hydrocarbon compound via an ether bond, such as methoxybenzene, ethoxybenzene, butoxybenzene (each isomer), dimethoxybenzene (each isomer), diethoxybenzene (each isomer), and dibutoxybenzene (each isomer); and halides such as chloromethane, chloroethane, chloropentane (each isomer), chlorooctane (each isomer), bromomethane, bromoethane, bromopentane (each isomer), bromooctane (each isomer), dichloroethane (each isomer), dichloropentane (each isomer), dichlorooctane (each isomer), dibromoethane (each isomer), dibromopentane (each isomer), dibromooctane (each isomer), chlorobenzene, bromobenzene, dichlorobenzene, dibromobenzene, benzyl chloride, and benzyl bromide.

Among these, (1) the hydrocarbon compounds having a linear, branched, or cyclic structure, (3) the aromatic hydrocarbon compounds that may have a substituent comprising a hydrocarbon group, and (6) the halides in which at least one hydrogen atom constituting a hydrocarbon compound having a linear, branched, or cyclic structure, or at least one hydrogen atom constituting an aromatic hydrocarbon compound that may have a substituent comprising a hydrocarbon group is substituted by a halogen atom are preferable from the viewpoint that these compounds are thermally stable, and that the compounds having an ether bond or a thioether bond as in (2), (4), and (5) may form an oxide or a peroxide depending on conditions. Moreover, the compounds containing a halogen atom as in (6) may be decomposed or form halogen radicals to contaminate products with halides, depending on conditions; thus, the (1) the hydrocarbon compounds having a linear, branched, or cyclic structure, and (3) the aromatic hydrocarbon compounds that may have a substituent comprising a hydrocarbon group are more preferable.

Another feature of the intermediate-boiling-point inactive compound (C) is that the normal boiling point of the intermediate-boiling-point inactive compound (C) is the temperature between a normal boiling point of the (A) and a normal boiling point of the (B). Specifically, the normal boiling point (Tc° C.) of the intermediate-boiling-point inactive compound is in Tb<Tc<Ta or Ta<Tc<Tb with respect to the normal boiling point (Ta° C.) of the active hydrogen-containing compound (A) and the normal boiling point (Tb° C.) of the compound (B) to be separated, and the intermediate-boiling-point inactive compound (C) can be selected and used appropriately according to the handled active hydrogen-containing compound (A) and compound (B). In this context, the normal boiling point represents a boiling point under 1 atmospheric pressure. The normal boiling point is difficult to specify based on a structure such as a general formula, and one measures or investigates and select normal boiling points for individual compounds. The measurement of the normal boiling point can be performed by a method known in the art such as a method specified by, for example, The Japanese Pharmacopoeia, 14th Edition, Part I-54, and can be carried out usually by any of those skilled in the art.

It is preferred that the normal boiling point (Tc° C.) of the intermediate-boiling-point inactive compound (C) should differ by 5° C. or more, more preferably by 10° C. or more, from the normal boiling point (Tb° C.) of (B) and the normal boiling point (Ta° C.) of (A) to be separated. In this case, the separation between (A) and the intermediate-boiling-point inactive compound (C) or between the intermediate-boiling-point inactive compound (C) and (B) is easy. Specifically, the case where the normal boiling point of the intermediate-boiling-point inactive compound (C) differs by 5° C. or more from the normal boiling point of (B) and the normal boiling point of (A) does not form the basis of the present embodiment. However, based on the findings that if the normal boiling points of two components to be separated differ by 5° C. or more, industrially sufficient distillation separation is possible, it shall be preferable to differ by 5° C. or more from the viewpoint that steps that may occur after separation between (A) and (B) become easy. Thus, it can be said that this preferable aspect holds only to separation means currently known in the art.

<Separation Between Active Hydrogen-Containing Compound (A) And Compound (B) that Reversibly Reacts with the Active Hydrogen-containing Compound>

A method of supplying the mixture containing the active hydrogen-containing compound (A) and the compound (B) that reversibly reacts with the active hydrogen-containing compound to an inactive layer comprising the intermediate-boiling-point inactive compound (C) in the multi-stage distillation column to separate (A) and (B), will be described.

The mixture containing the active hydrogen-containing compound (A) and the compound (B) that reversibly reacts with the active hydrogen-containing compound is supplied to the inactive layer of the intermediate-boiling-point inactive compound (C) within the multi-stage distillation column, and (A) and (B) are separated in the multi-stage distillation column and collected. Specifically, in supplying the mixture containing (A) and (B) to the multi-stage distillation column, the inactive layer comprising the (C) is formed at a height having a supply port to which the mixture of the (A) and the (B) is supplied within the multi-stage distillation column.

The active hydrogen-containing compound (A) and the compound (B) are supplied to the intermediate stage of the multi-stage distillation column. The "intermediate stage" referred to herein is between the top of the column and the bottom of the column in a height direction in the multi-stage distillation column, and is the position at which at least one theoretical plate, preferably at least three theoretical plates, can exist above and below a stage having the supply port. The top of the column refers to a part that is the topmost part of the multi-stage distillation column and from which the gas phase is continuously extracted, and the bottom of the column refers to the bottommost part of the multi-stage distillation column.

Although the active hydrogen-containing compound (A) may be supplied in a liquid state, supplied in the state of a gas-liquid mixed phase, or supplied in a gas state, one that is preferred is to supply it in a gas state from the viewpoint of shortening a residence time in a line that supplies the active hydrogen-containing compound (A) to the multi-stage distillation column, to thereby suppress the thermal denaturation reaction or the like of the active hydrogen-containing compound (A). Although the compound (B) may also be supplied in a liquid state, supplied in the state of a gas-liquid mixed phase, or supplied in a gas state, one that is preferred is to supply it in a gas state from the viewpoint of shortening a residence time in a line that supplies the compound (B) to the multi-stage distillation column, to thereby suppress the thermal denaturation reaction or the like of the compound (B). Specifically, although the mixture containing the active hydrogen-containing compound (A) and the compound (B) may also be supplied in a liquid state, supplied in the state of a gas-liquid mixed phase, or supplied in a gas state, one that is preferred is to supply it in a gas state from the viewpoint of shortening a residence time in a line that supplies the mixture containing the active hydrogen-containing compound (A) and the compound (B) to the multi-stage distillation column, to thereby suppress the thermal denaturation reaction of each of the active hydrogen-containing compound (A) and the compound (B). Moreover, in the case of supplying the mixture in a liquid state, the reaction between the active hydrogen-containing compound (A) and the compound (B) often proceeds easily compared with the case of supplying the mixture in a gas state; thus, also from such a viewpoint, the mixture containing the active hydrogen-containing compound (A) and the compound (B) is preferably supplied in a gas state.

The "inactive layer" according to the present embodiment refers to a layer that is composed mainly of the intermediate-boiling-point inactive compound (C) described above; and one that is preferred is (C) in a gas state, and the gas phases of (A) and (B) are separated by the (C) in a gas state. More preferably, the (A) in a gas state and the (B) in a gas state are separated to above or below the inactive layer by distillation separation by supplying the mixture in a gas state to the inactive layer comprising the (C) in a gas state.

The case where a conjugate (reaction product) of the active hydrogen-containing compound (A) and the compound (B) forms due to the reaction between the active hydrogen-containing compound (A) and the compound (B) to reduce the yield is frequent in an attempt to supply the mixture of the active hydrogen-containing compound (A) and the compound (B) to the multi-stage distillation column and separate the active hydrogen-containing compound (A) and the compound (B). It is considered that an effect capable of suppressing the reaction between the active hydrogen-containing compound (A) and the compound (B) caused by the contact between the active hydrogen-containing compound (A) and the compound (B), to thereby separate the active hydrogen-containing compound (A) and the compound (B) is exerted by supplying the mixture of the active hydrogen-containing compound (A) and the compound (B) to the inactive layer and separating and/or diluting the active hydrogen-containing compound (A) and the compound (B). Moreover, for example, taking, as an example, the case where the active hydrogen-containing compound (A) is a hydroxy compound and the compound (B) is an isocyanate, there may arise a problem: an N-substituted carbamic acid ester forms during distillation and the N-substituted carbamic acid ester polymerizes during distillation or in reactions downstream thereof, so that the compound in a polymer form adheres to the apparatus, unless adopting the method as in the present embodiment. According to the method of the present embodiment, even such a problem can be prevented.

The inactive layer of the present embodiment is formed in the range of at least one plate, preferably at least three plates, above and below the supply port. The liquid phase and/or the gas phase, preferably, the liquid phase and the gas phase, of the inactive layer have a content of the intermediate-boiling-point inactive compound (C) of preferably 5 wt % or more, more preferably 10 wt % or more, further preferably 30 wt % or more. The content of the intermediate-boiling-point inactive compound (C) can be determined by sampling liquid-phase components and/or gas-phase components from the multi-stage distillation column and analyzing them by a method known in the art such as gas chromatography or liquid chromatography. Moreover, it is also acceptable to determine in advance the T-XY diagrams of components within the multi-stage distillation column and predict the content of the intermediate-boiling-point inactive compound (C) from temperatures and pressures at arbitrary positions within the multi-stage distillation column using the T-XY diagrams.

The range of the inactive layer can be adjusted by controlling the quantity of heat applied to an evaporator disposed at the bottom of the multi-stage distillation column, the quantity of reflux at the top of the multi-stage distillation column, the amount of supply of the intermediate-boiling-point inactive compound (C), the amount of supply of the mixture containing the active hydrogen-containing compound (A) and the compound (B), a pressure within the multi-stage distillation column, etc. Moreover, even the case where the intermediate-boiling-point inactive compound (C) exists at a stage other than the range described above is also acceptable in some cases.

Meanwhile, in initiating the supply of the mixture to the multi-stage distillation column, a method of supplying the mixture to the multi-stage distillation column adjusted to a state filled with a gas of the (C) in the gas-phase part by introducing only the (C) into the multi-stage distillation column and boiling the (C) is preferable, and one that is more preferred is to supply the mixture to the multi-stage distillation column adjusted to a total reflux state of the (C).

As described above, the mixture containing the active hydrogen-containing compound (A) and the compound (B) is supplied, preferably in a gas state, to the inactive layer of the multi-stage distillation column. In the case where the mixture is a mixture containing an active hydrogen-containing compound (A) and a compound (B) obtained by subjecting a conjugate of the active hydrogen-containing compound (A) and the compound (B) (e.g., the compound represented by formula (5)) to a thermal decomposition reaction, one that is preferred is to heat a line connecting the distillation column to a thermal decomposition reactor in which the thermal decomposition reaction is performed, to the condensation temperatures or higher, at operating pressure, of the active hydrogen-containing compound (A) and the compound (B) that form by the thermal decomposition reaction, and transport the mixture containing the active hydrogen-containing compound (A) and the compound (B) in a gas state.

For example, in the case of supplying a mixture containing an isocyanate and a hydroxy compound that form by subjecting the N-substituted carbamic acid ester to a thermal decomposition reaction, in a gas state to the distillation column, one that is preferred is to heat a line connecting the distillation column to a thermal decomposition reactor in which the thermal decomposition of the N-substituted carbamic acid ester is performed, to the condensation temperatures or higher of the isocyanate and the hydroxy compound that form by the thermal decomposition of the N-substituted carbamic acid ester, and transport the isocyanate and the hydroxy compound in a gas state.

Meanwhile, the intermediate-boiling-point inactive compound (C) can also be supplied as a liquid to the multi-stage distillation column or can also be supplied in a gas state. The intermediate-boiling-point inactive compound (C) may be supplied from any position of the multi-stage distillation column and may be supplied from a supply port disposed at the upper part of the multi-stage distillation column; may be supplied from a supply port disposed in the lower part of the multi-stage distillation column; may be supplied from a supply port disposed at the same height as in a supply port through which the mixture is supplied; or may be supplied from the supply port through which the mixture is supplied.

It is preferred that the amount of the intermediate-boiling-point inactive compound (C) used should be 0.01 time to 100 times with respect to the weight of the mixture, though depending on the compounds used, the compounds to be separated, and operation conditions. Although it is preferred that the amount of the intermediate-boiling-point inactive compound (C) used should be in excess for suppressing the reaction between the active hydrogen-containing compound (A) and the compound (B), too great an excess is not preferable because the amount of throughput (amount of supply of the mixture containing the active hydrogen-containing compound (A) and the compound (B)) in the distillation column decreases. Thus, the amount of the intermediate-boiling-point inactive compound (C) used is more preferably 0.1 time to 50 times, further preferably 0.3 time to 30 times, with respect to the weight of the mixture.

Although the pressure at which the distillation separation between the active hydrogen-containing compound (A) and the compound (B) is performed differs depending on the composition of components supplied to the multi-stage distillation column in which the distillation separation is carried out, the temperature, the type of the multi-stage distillation column, etc., and the reaction is performed under reduced pressure, under atmospheric pressure, or under increased pressure, it is usually preferred that it should be carried out in the range of 0.01 kPa to 10 MPa; and in consideration of ease of industrial practice, one that is more preferred is in the range of 0.1 kPa to 1 MPa, and one that is further preferred is in the range of 0.5 kPa to 50 kPa.

Although the temperature at which the distillation separation between the active hydrogen-containing compound (A) and the compound (B) is performed differs depending on the composition of components supplied to the multi-stage distillation column in which the distillation separation is carried out, the temperature, the type of the multi-stage distillation column, etc., one that is preferred in the range of 50° C. to 350° C., one that is more preferred is 80° C. to 300° C., and one that is further preferred is performed in the range of 100° C. to 250° C. because: the active hydrogen-containing compound (A), the compound (B), or the intermediate-boiling-point inactive compound (C) may be thermally denatured in the case of too high a temperature; and on the other hand, the need to provide a new facility for cooling arises in the case of too low a temperature, so that industrial practice is not easy.

The intermediate-boiling-point inactive compound (C) may be discharged from the top of the multi-stage distillation column or may be extracted from the bottom of the multi-stage distillation column. For example, in the case where the normal boiling point (Tc° C.) of the intermediate-boiling-point inactive compound (C) is in Tb<Tc<Ta with respect to the normal boiling point (Ta° C.) of the active hydrogen-containing compound (A) and the normal boiling point (Tb° C.) of the compound (B), one can extract the intermediate-boiling-point inactive compound (C) together with the compound (B) from the top of the distillation column, can extract it together with the active hydrogen-containing compound (A) from the bottom of the distillation column, or can extract the intermediate-boiling-point inactive compound (C) from the top of the column and the bottom of the column. One that is preferred is a method of extracting the intermediate-boiling-point inactive compound (C) from either the top of the column or the bottom of the column, and, for example, one can extract the intermediate-boiling-point inactive compound (C) together with the compound (B) from the top of the column and further distill the obtained mixture of the intermediate-boiling-point inactive compound (C) and the compound (B) to collect the compound (B), while collecting the active hydrogen-containing compound (A) substantially free from the intermediate-boiling-point inactive compound (C) from the bottom of the column and recycling it in the production step of a conjugate of the active hydrogen-containing compound (A) and the compound (B), for example, the compound represented by formula (5), or the thermal decomposition step of the compound. Moreover, for example, one can extract the intermediate-boiling-point inactive compound together with the active hydrogen-containing compound (A) from the bottom of the column and further distillation-separate the obtained mixture of the intermediate-boiling-point inactive compound (C) and the active hydrogen-containing compound (A) to collect the active hydrogen-containing compound (A) and recycle it in the production step of a conjugate of the active hydrogen-containing compound (A) and the compound (B), for example, the compound represented by formula (5), or the thermal decomposition step of the compound, while collecting the compound (B) substantially free from the intermediate-boiling-point inactive compound (C) from the top of the column. Moreover, the collected intermediate-boiling-point inactive compound (C) can be recycled.

Moreover, for example, in the case where the normal boiling point (Tc° C.) of the intermediate-boiling-point inactive compound is in Ta<Tc<Tb with respect to the normal boiling point (Ta° C.) of the active hydrogen-containing compound (A) and the normal boiling point (Tb° C.) of the compound (B), one can extract the intermediate-boiling-point inactive compound (C) together with the active hydrogen-containing compound (A) from the top of the distillation column, can extract it together with the compound (B) from the bottom of the distillation column, or can extract the intermediate-boiling-point inactive compound (C) from the top of the column and the bottom of the column. In this case as well, one that is preferred is a method of extracting the intermediate-boiling-point inactive compound (C) from either the top of the column or the bottom of the column, and, for example, one can extract the intermediate-boiling-point inactive compound together with the active hydrogen-containing compound (A) from the top of the column and further distillation-separate the obtained mixture of the intermediate-boiling-point inactive compound (C) and the active hydrogen-containing compound (A) to collect the active hydrogen-containing compound (A) and recycle it in the production step of a conjugate of the active hydrogen-containing compound (A) and the compound (B), for example, the compound represented by formula (5), or the thermal decomposition step of the compound, while collecting the compound (B) substantially free from the intermediate-boiling-point inactive compound (C) from the bottom of the column. Moreover, for example, one can extract the intermediate-boiling-point inactive compound (C) together with the compound (B) from the bottom of the column and distillation-separate the obtained mixture of the intermediate-boiling-point inactive compound (C) and the compound (B) to collect the compound (B), while collecting the active hydrogen-containing compound (A) substantially free from the intermediate-boiling-point inactive compound (C) from the top of the column and recycling it in the production step of a conjugate of the active hydrogen-containing compound (A) and the compound (B), for example, the compound represented by formula (5), or the thermal decomposition step of the compound. Moreover, the collected intermediate-boiling-point inactive compound (C) can be recycled.

Taking, as an example, the case where the active hydrogen-containing compound (A) and the compound (B) are a hydroxy compound and an isocyanate, respectively, which form by the thermal decomposition of an N-substituted carbamic acid ester, for example, in the case where the normal boiling point (Tc° C.) of the intermediate-boiling-point inactive compound is in Tb<Tc<Ta with respect to the normal boiling point (Tb° C.) of the isocyanate and the normal boiling point (Ta° C.) of the hydroxy compound, one can extract the intermediate-boiling-point inactive compound (C) together with the isocyanate from the top of the multi-stage distillation column, can extract it together with the hydroxy compound from the bottom of the multi-stage distillation column, or can extract the intermediate-boiling-point inactive compound (C) from the top of the column and the bottom of the column. One that is preferred is a method of extracting the intermediate-boiling-point inactive compound (C) from either the top of the column or the bottom of the column, and, for example, one can extract the intermediate-boiling-point inactive compound (C) together with the isocyanate from the top of the column and further distill the obtained mixture of the intermediate-boiling-point inactive compound (C) and the isocyanate to collect the isocyanate, while collecting the hydroxy compound substantially free from the intermediate-boiling-point inactive compound (C) from the bottom of the column and recycling it in the production step of the N-substituted carbamic acid ester or the thermal decomposition step of the N-substituted carbamic acid ester. Moreover, for example, one can extract the intermediate-boiling-point inactive compound (C) together with the hydroxy compound from the bottom of the column and further distillation-separate the obtained mixture of the intermediate-boiling-point inactive compound (C) and the hydroxy compound to collect the hydroxy compound and recycle it in the production step of the N-substituted carbamic acid ester or the thermal decomposition step of the N-substituted carbamic acid ester, while collecting the isocyanate substantially free from the intermediate-boiling-point inactive compound (C) from the top of the column.

Moreover, for example, in the case where the normal boiling point (Tc° C.) of the intermediate-boiling-point inactive compound is in Ta<Tc<Tb with respect to the normal boiling point (Tb° C.) of the isocyanate and the normal boiling point (Ta° C.) of the hydroxy compound, one can extract the intermediate-boiling-point inactive compound (C) together with the hydroxy compound from the top of the multi-stage distillation column, can extract it together with the isocyanate from the bottom of the multi-stage distillation column, or can extract the intermediate-boiling-point inactive compound (C) from the top of the column and the bottom of the column. In this case as well, one that is preferred is a method of extracting the intermediate-boiling-point inactive compound (C) from either the top of the column or the bottom of the column, and, for example, one can extract the intermediate-boiling-point inactive compound (C) together with the hydroxy compound from the top of the column and further distillation-separate the obtained mixture of the intermediate-boiling-point inactive compound (C) and the hydroxy compound to collect the hydroxy compound and recycle it in the production step of the N-substituted carbamic acid ester or the thermal decomposition step of the N-substituted carbamic acid ester, while collecting the isocyanate substantially free from the intermediate-boiling-point inactive compound (C) from the bottom of the column. Moreover, for example, one can extract the intermediate-boiling-point inactive compound (C) together with the isocyanate from the bottom of the column and distillation-separate the obtained mixture of the intermediate-boiling-point inactive compound (C) and the isocyanate to collect the isocyanate, while collecting the hydroxy compound substantially free from the intermediate-boiling-point inactive compound (C) from the top of the column and recycling it in the production step of the N-substituted carbamic acid ester or the thermal decomposition step of the N-substituted carbamic acid ester.

Although materials for the apparatus in which the distillation separation between the isocyanate and the hydroxy compound is performed, and lines may be any of those known in the art unless having adverse effects on starting materials or reactants, SUS304, SUS316, SUS316L, or the like is inexpensive and can be used preferably. There is no particular limitation to the form of the distillation column, and a distillation column known in the art can be used. For example, various methods known in the art such as a style using a distillation apparatus containing any of a multi-stage distillation column, a continuous multi-stage distillation column, and a packed column, and a style combining these are used as the distillation column.

Although the multi-stage distillation column may be any one that is a distillation column having multiple plates in which the number of theoretical plates in distillation is three or more and continuous distillation is possible, the multi-stage distillation column becomes huge in the case where the number of theoretical plates is too large, so that industrial practice may be difficult. Thus, the number of theoretical plates is preferably set to 500 or less. As such a multi-stage distillation column, one can use, for example, any one that is usually used as a multi-stage distillation column, such as a plate column system using trays such as bubble cap trays, porous plate trays, valve trays, or countercurrent trays, and a packed column style filled with various types of packing materials such as Raschig ring, Lessing ring, Pall ring, Berl Saddle, Interlock saddle, Dixon packing, McMahon packing, HELIPACK, Sulzer packing, and Mellapak.

As the packed column, one can use any one that is a packed column filled with the above-described packing materials known in the art within the column. Furthermore, one having a plate-packed mixed column style having both of plate parts and parts filled with packing materials is also preferably used.

<Method for Producing Isocyanate>

A method for producing an isocyanate in the present embodiment comprises: a step of obtaining a mixture containing an isocyanate and a hydroxy compound by the thermal decomposition reaction of an N-substituted carbamic acid ester; and a step of separating the isocyanate from the mixture by the above-described method for separating an isocyanate. Furthermore, one can produce an isocyanate with an organic primary amine as a raw material by: producing an N-substituted carbamic acid ester with the organic primary amine as a raw material by a step comprising the above-described step of producing an N-substituted carbamic acid ester (Process (I), Process (II), or Step (A) and Step (B)) or a step combining the step of producing an N-substituted carbamic acid ester (Process (I), Process (II), or Step (A) and Step (B)) with Step (Y); producing a mixture containing an isocyanate and a hydroxy compound by the thermal decomposition reaction of the N-substituted carbamic acid ester; and separating the isocyanate from the mixture by the above-described method for separating an isocyanate.

According to the method for producing an isocyanate in the present embodiment, one can efficiently obtain an isocyanate at high yields.

EXAMPLES

Hereinafter, the present invention will be described specifically based on Examples, and however, the scope of the present invention is not limited to these Examples.

<Analysis Method>

1) NMR Analysis Method

Apparatus: JNM-A400 FT-NMR system manufactured by JEOL Ltd., Japan (1) Preparation of $^1$H-NMR Analysis Sample and $^{13}$C-NMR Analysis Sample Approximately 0.3 g of a sample solution was weighed, and a solution in which approximately 0.7 g of deuterated chloroform (manufactured by Sigma-Sigma-Aldrich Corp., USA, 99.8%) and 0.05 g of tetramethyltin (manufactured by Wako Pure Chemical Industries, Ltd., Japan, Wako first grade) as an internal standard were added and uniformly mixed was used as an NMR analysis sample.

(2) Quantitative Analysis Method

Analysis was conducted on each standard, and the quantitative analysis of the analysis sample solution was carried out based on a prepared calibration curve.

2) Liquid Chromatography Analysis Method

Apparatus: LC-10AT system manufactured by Shimadzu Corp., Japan

Column: two Silica-60 columns (manufactured by TOSOH CORP., Japan) connected in series Developing solvent: mixed solution of hexane/tetrahydrofuran=80/20 (volume ratio)

Solvent flow rate: 2 mL/min.

Column temperature: 35° C.

Detector: R.I. (refractometer)

(1) Liquid Chromatography Analysis Sample

Approximately 0.1 g of a sample was weighed, and a solution in which approximately 1 g of tetrahydrofuran (manufactured by Wako Pure Chemical Industries, Ltd., Japan, dehydrated) and approximately 0.02 g of bisphenol A (manufactured by Wako Pure Chemical Industries, Ltd., Japan, first grade) as an internal standard were added and uniformly mixed was used as a sample of liquid chromatography analysis.

(2) Quantitative Analysis Method

Analysis was conducted on each standard, and the quantitative analysis of the analysis sample solution was carried out based on a prepared calibration curve.

Example 1

Step (1-1): Production of N,N'-hexanediyl-dicarbamic acid diphenyl ester

Reactions were performed using an apparatus shown in FIG. 1.

In the state where a line 14 was closed, 13.50 kg (63 mol) of diphenyl carbonate (manufactured by Sigma-Aldrich Corp., USA) was supplied from a reservoir 101 through a line 11 to a 50-L (internal volume) baffled reaction container 104 made of SUS, and 9.87 kg (105 mol) of phenol (manufactured by Sigma-Aldrich Corp., USA) was supplied from a reservoir 102 through a line 12 to the reactor made of SUS. A solution temperature within the reactor 104 was adjusted to approximately 50° C., and 2.44 kg (21 mol) of hexamethylenediamine (manufactured by Sigma-Aldrich Corp., USA) was supplied at approximately 2.00 kg/hr from a reservoir 103 through a line 13 to the reactor 104.

As a result of analyzing the solution after reaction (hereinafter, also referred to as a "reaction solution (1)") by liquid chromatography, N,N'-hexanediyl-dicarbamic acid diphenyl ester formed at a yield of 99.5%.

The line 14 was opened, and the reaction solution (1) was transported to a reservoir 105 through the line 14.

Step (1-2): Thermal decomposition of N,N'-hexanediyl-dicarbamic acid diphenyl ester and separation and collection of isocyanate Reactions were performed using an apparatus shown in FIG. 2.

n-Dodecane (manufactured by TOKYO CHEMICAL INDUSTRY CO., LTD., Japan) was supplied to the bottom of a continuous multi-stage distillation column 202 of approximately 5 cm in inside diameter filled with Dixon packing (6 mmφ)), and the total reflux operation of n-dodecane was performed with a pressure at the top of the column set to approximately 15 kPa to form an inactive layer containing n-dodecane. The quantity of heat necessary for the evaporation of n-dodecane was supplied by circulating the solution of the lower part of the column through lines 26 and 28 and a reboiler 204.

A thin-film distillation apparatus 201 (manufactured by KOBELCO ECO-SOLUTIONS Co., Ltd., Japan) of 0.1 m² in heat transfer area was heated to 220° C., and the internal pressure was set to approximately 13 kPa. The reaction solution collected into the reservoir 105 in Step (1-1) was heated to 150° C. and supplied at approximately 1.0 kg/hr to the upper part of the thin-film distillation apparatus 201 through a line 21, and the thermal decomposition of N,N'-hexanediyl-dicarbamic acid diphenyl ester was performed to thereby obtain a mixture containing an isocyanate and a hydroxy compound (phenol). Liquid-phase components were extracted through a line 23 from the bottom of the thin-film distillation apparatus 201 and circulated to the upper part of the thin-film distillation apparatus 201 through a line 24 and the line 21. The mixture was extracted as gas-phase components through a line 22 kept at 220° C.

The mixture, which was gas-phase components, extracted through the line 22 from the thin-film distillation apparatus 201 was continuously fed to the intermediate stage of the continuous multi-stage distillation column 202, and at the same time, n-dodecane was supplied at 0.3 kg/hr through a line 29 from a reservoir 210 to perform the distillation separation of the mixture which was gas-phase components. The quantity of heat necessary for the distillation separation was supplied by circulating the solution of the lower part of the column through the lines 26 and 28 and the reboiler 204. A solution temperature at the bottom of the continuous multi-stage distillation column 202 was 150° C., and a pressure at the top of the column was approximately 15 kPa. A gas discharged from the top of the continuous multi-stage distillation column 202 was condensed in a condenser 203 through a line 25 and continuously extracted to a reservoir 208 through a line 27. On the other hand, liquid-phase components were extracted through the line 26 from the bottom of the column and supplied to a distillation column 205. Gas components and liquid components at both the upper and lower first theoretical plates relative to the position of line 22 of the continuous multi-stage distillation column 202 were analyzed at steady state, and operation was performed such that all contained 10 wt % or more of n-dodecane.

The liquid-phase components extracted through the line 26 were continuously fed to the intermediate stage of the continuous multi-stage distillation column 205 of approximately 5 cm in inside diameter filled with Dixon packing (6 mmφ) to perform the distillation separation of the liquid-phase components. The quantity of heat necessary for the distillation separation was supplied by circulating the solution of the lower part of the column through lines 31 and 33 and a reboiler 207. A solution temperature at the bottom of the continuous multi-stage distillation column 205 was 150° C., and a pressure at the top of the column was approximately 1.5 kPa. A gas discharged from the top of the continuous multi-stage distillation column 205 was condensed in a condenser 206 through a line 30 and continuously extracted to a reservoir 209 through a line 32. An extracted amount at steady state was approximately 101 g/hr.

The solution extracted through the line 32 was a solution containing approximately 99.8 wt % of hexamethylene diisocyanate. The yield with respect to hexamethylenediamine was 92.8%.

Incidentally, in the case where the normal boiling point of hexamethylene diisocyanate is defined as Tb and the normal boiling point of the hydroxy compound is defined as Ta, a normal boiling point Tc of n-dodecane satisfied Ta<Tc<Tb.

Example 2

Step (2-1): Production of 3-(phenoxycarbonylamino-methyl)-3,5,5-trimethylcyclohexylcarbamic acid phenyl ester Reactions were performed using the apparatus shown in FIG. 1.

Reactions were performed in the same way as in Step (1-1) of Example 1 except that: the amount of diphenyl carbonate used was set to 10.5 kg (49 mol); the amount of phenol used was set to 9.24 kg (98.3 mol); and 3.41 kg (20 mol) of 3-aminomethyl-3,5,5-trimethylcyclohexylamine (manufactured by Sigma-Aldrich Corp., USA) was used instead of hexamethylenediamine.

As a result of analyzing the solution after reaction (hereinafter, also referred to as a "reaction solution (2)") by liquid chromatography, 3-(phenoxycarbonylamino-methyl)-3,5,5-trimethylcyclohexylcarb amic acid phenyl ester formed at a yield of 99.1%.

The line 14 was opened, and the reaction solution (2) was transported to the reservoir 105 through the line 14.

Step (2-2): Thermal decomposition of 3-(phenoxy-carbonylamino-methyl)-3,5,5-trimethylcyclohexyl-carbamic acid phenyl ester and separation and collection of isocyanate Reactions were performed using the apparatus shown in FIG. 2.

1,3,5-Triethylbenzene (manufactured by TOKYO CHEMICAL INDUSTRY CO., LTD., Japan) was supplied to the bottom of the continuous multi-stage distillation column 202, and the total reflux operation of 1,3,5-triethylbenzene was performed with a pressure at the top of the column set to approximately 5 kPa. The quantity of heat necessary for the evaporation of 1,3,5-triethylbenzene was supplied by circulating the solution of the lower part of the column through the lines 26 and 28 and the reboiler 204.

The thin-film distillation apparatus 201 was heated to 270° C., and the internal pressure was set to approximately 13 kPa. The reaction solution (2) collected into the reservoir 105 in Step (2-1) was heated to 150° C. and supplied at approximately 1.0 kg/hr to the upper part of the thin-film distillation apparatus 201 through the line 21, and the thermal decomposition of 3-(phenoxycarbonylamino-methyl)-3,5,5-trimethylcyclohexylcarbamic acid phenyl ester was performed to thereby obtain a mixture (2) containing an isocyanate and a hydroxy compound. Liquid-phase components were extracted through the line 23 from the bottom of the thin-film distillation apparatus 201 and circulated to the upper part of the thin-film distillation apparatus 201 through the line 24 and the line 21. The mixture (2) was extracted as gas-phase components through the line 22.

The mixture (2), which was gas-phase components, extracted through the line 22 from the thin-film distillation apparatus 201 was continuously fed to the intermediate stage of the continuous multi-stage distillation column 202, and at the same time, 1,3,5-triethylbenzene was supplied at 0.2 kg/hr through the line 29 from the reservoir 210 to perform the distillation separation of the mixture (2) which was gas-phase components. The quantity of heat necessary for the distillation separation was supplied by circulating the solution of the lower part of the column through the lines 26 and 28 and the reboiler 204. A solution temperature at the bottom of the continuous multi-stage distillation column 202 was 200° C., and a pressure at the top of the column was approximately 5 kPa. A gas discharged from the top of the continuous multi-stage distillation column 202 was condensed in the condenser 203 through the line 25 and continuously extracted through the line 27. On the other hand, liquid-phase components were extracted through the line 26 from the bottom of the column and supplied to the distillation column 205. Gas components and liquid components at both the upper and lower third theoretical plates relative to the position of line 22 of the continuous multi-stage distillation column 202 were analyzed at steady state, and operation was performed such that all contained 30 wt % or more of 1,3,5-triethylbenzene.

The liquid-phase components extracted through the line 26 were continuously fed to the intermediate stage of the continuous multi-stage distillation column 205 to perform the distillation separation of the liquid-phase components. The quantity of heat necessary for the distillation separation was supplied by circulating the solution of the lower part of the column through the lines 31 and 33 and the reboiler 207. A solution temperature at the bottom of the continuous multi-stage distillation column 205 was 150° C., and a pressure at the top of the column was approximately 1.5 kPa. A gas discharged from the top of the continuous multi-stage distillation column 205 was condensed in the condenser 206 through the line 30 and continuously extracted to the reservoir 209 through the line 32. The solution extracted through the line 32 was a solution containing approximately 99.8 wt % of isophorone diisocyanate. The yield with respect to 3-aminomethyl-3,5,5-trimethyl cyclohexylamine was 91.7%.

Incidentally, in the case where the normal boiling point of isophorone diisocyanate is defined as Tb and the normal boiling point of the hydroxy compound is defined as Ta, a normal boiling point Tc of 1,3,5-triethylbenzene satisfied Ta<Tc<Tb.

Example 3

Step (3-1): Production of N,N'-(4,4'-methanediyl-dicyclohexyl)-di(carbamic acid phenyl ester)

Reactions were performed using the apparatus shown in FIG. 1.

Reactions were performed in the same way as in Step (1-1) of Example 1 except that: the amount of diphenyl carbonate used was set to 13.3 kg (62 mol); the amount of phenol used was set to 11.2 kg (119 mol); and 3.26 kg (15.5 mol) of 4,4'-methylenebis(cyclohexylamine) (manufactured by Sigma-Aldrich Corp., USA) was used instead of hexamethylenediamine.

As a result of analyzing the solution after reaction (hereinafter, also referred to as a "reaction solution (3)") by liquid chromatography, N,N'-(4,4'-methanediyl-dicyclohexyl)-di(carbamic acid phenyl ester) formed at a yield of 98.8%.

The line 14 was opened, and the reaction solution (3) was transported to the reservoir 105 through the line 14.

Step (3-2): Thermal decomposition of N,N'-(4,4'-methanediyl-dicyclohexyl)-di(carbamic acid phenyl ester) and separation and collection of isocyanate Reactions were performed using the apparatus shown in FIG. 2.

Tetraethylene glycol dimethyl ether (manufactured by TOKYO CHEMICAL INDUSTRY CO., LTD., Japan) was supplied to the bottom of the continuous multi-stage distillation column 202, and the total reflux operation of tetraethylene glycol dimethyl ether was performed with a pressure at the top of the column set to approximately 0.1 kPa. The quantity of heat necessary for the evaporation of tetraethylene glycol dimethyl ether was supplied by circulating the solution of the lower part of the column through the lines 26 and 28 and the reboiler 204.

The thin-film distillation apparatus 201 was heated to 300° C., and the internal pressure was set to approximately 2 kPa. The reaction solution (3) collected into the reservoir 105 in Step (3-1) was heated to 150° C. and supplied at approximately 0.8 kg/hr to the upper part of the thin-film distillation apparatus 201 through the line 21, and the thermal decomposition of N,N'-(4,4'-methanediyl-dicyclohexyl)-di(carbamic acid phenyl ester) was performed to thereby obtain a mixture (3) containing an isocyanate and a hydroxy compound. Liquid-phase components were extracted through the line 23 from the bottom of the thin-film distillation apparatus 201 and circulated to the upper part of the thin-film distillation apparatus 201 through the line 24 and the line 21. The mixture (3) was extracted as gas-phase components through the line 22.

The mixture (3), which was gas-phase components, extracted through the line 22 from the thin-film distillation apparatus 201 was continuously fed to the intermediate stage of the continuous multi-stage distillation column 202, and at the same time, tetraethylene glycol dimethyl ether was supplied at 0.4 kg/hr through the line 29 from the reservoir 210 to perform the distillation separation of the mixture (3) which was gas-phase components. The quantity of heat necessary for the distillation separation was supplied by circulating the solution of the lower part of the column through the lines 26 and 28 and the reboiler 204. A solution temperature at the bottom of the continuous multi-stage distillation column 202 was 200° C., and a pressure at the top of the column was approximately 0.1 kPa. A gas discharged from the top of the continuous multi-stage distillation column 202 was condensed in the condenser 203 through the line 25 and continuously extracted through the line 27. On the other hand, liquid-phase components were extracted through the line 26 from the bottom of the column and supplied to the distillation column 205. Gas components and liquid components at both the upper and lower third theoretical plates relative to the position of line 22 of the continuous multi-stage distillation column 202 were analyzed at steady state, and operation was performed such that all contained 30 wt % or more of tetraethylene glycol dimethyl ether.

The liquid-phase components extracted through the line 26 were continuously fed to the intermediate stage of the continuous multi-stage distillation column 205 to perform the distillation separation of the liquid-phase components. The quantity of heat necessary for the distillation separation was supplied by circulating the solution of the lower part of the column through the lines 31 and 33 and the reboiler 207. A solution temperature at the bottom of the continuous multi-stage distillation column 205 was 240° C., and a pressure at the top of the column was approximately 0.1 kPa. A gas discharged from the top of the continuous multi-stage distillation column 205 was condensed in the condenser 206 through the line 30 and continuously extracted to the reservoir 209 through the line 32. The solution extracted through the line 32 was a solution containing approximately 99.8 wt % of dicyclohexylmethane diisocyanate. The yield with respect to 4,4'-methylenebis(cyclohexylamine) was 87.2%.

Incidentally, in the case where the normal boiling point of dicyclohexylmethane diisocyanate is defined as Tb and the normal boiling point of the hydroxy compound is defined as Ta, a normal boiling point Tc of tetraethylene glycol dimethyl ether satisfied Ta<Tc<Tb.

Example 4

Step (4-1): Production of 3-(phenoxycarbonylamino-methyl)-3,5,5-trimethylcyclohexylcarbamic acid phenyl ester Reactions were performed using the apparatus as shown in FIG. 1.
Reactions were performed in the same way as in Step (1-1) of Example 1 except that: the amount of diphenyl carbonate used was set to 12.2 kg (57 mol); the amount of phenol used was set to 15.2 kg (162 mol); and 4.43 kg (26 mol) of 3-aminomethyl-3,5,5-trimethylcyclohexylamine was used instead of hexamethylenediamine.

As a result of analyzing the solution after reaction (hereinafter, also referred to as a "reaction solution (4)") by liquid chromatography, 3-(phenoxycarbonylamino-methyl)-3,5,5-trimethylcyclohexylcarbamic acid phenyl ester formed at a yield of 97.9%.

The line 14 was opened, and the reaction solution (4) was transported to the reservoir 105 through the line 14.

Step (4-2): Thermal decomposition of 3-(phenoxycarbonylamino-methyl)-3,5,5-trimethylcyclohexylcarb amic acid phenyl ester and separation and collection of isocyanate Reactions were performed using the apparatus shown in FIG. 2.
Diphenyl ether (manufactured by TOKYO CHEMICAL INDUSTRY CO., LTD., Japan) was supplied to the bottom of the continuous multi-stage distillation column 202, and the total reflux operation of diphenyl ether was performed with a pressure at the top of the column set to approximately 0.1 kPa. The quantity of heat necessary for the evaporation of diphenyl ether was supplied by circulating the solution of the lower part of the column through the lines 26 and 28 and the reboiler 204.

Thermal decomposition was performed in the same way as in Step (2-2) of Example 2 to obtain a mixture (4) containing an isocyanate and a hydroxy compound except that the 3-(phenoxycarbonylamino-methyl)-3,5,5-trimethylcyclohexylcarb amic acid phenyl ester obtained in Step (4-1) was used.

Moreover, the separation and collection of the isocyanate were performed in the same way as in Step (2-2) of Example 2 except that diphenyl ether was supplied at 0.4 kg/hr instead of 1,3,5-triethylbenzene. A gas discharged from the top of the continuous multi-stage distillation column 205 was condensed in the condenser 206 through the line 30 and continuously extracted to the reservoir 209 through the line 32. The solution extracted through the line 32 was a solution containing approximately 99.2 wt % of isophorone diisocyanate. The yield with respect to 3-aminomethyl-3,5,5-trimethylcyclohexylamine was 91.2%.

Incidentally, in the case where the normal boiling point of isophorone diisocyanate is defined as Tb and the normal boiling point of the hydroxy compound is defined as Ta, a normal boiling point Tc of diphenyl ether satisfied Ta<Tc<Tb.

Example 5

Step (5-1): Production of 3-(phenoxycarbonylamino-methyl)-3,5,5-trimethylcyclohexylcarbamic acid phenyl ester Reactions were performed using the apparatus shown in FIG. 1.
Reactions were performed in the same way as in Step (1-1) of Example 1 except that: the amount of diphenyl carbonate used was set to 14.2 kg (66 mol); the amount of phenol used was set to 13.9 kg (148 mol); and 2.39 kg (17 mol) of 3-aminomethyl-3,5,5-trimethylcyclohexylamine was used instead of hexamethylenediamine.

As a result of analyzing the solution after reaction (hereinafter, also referred to as a "reaction solution (5)") by liquid chromatography, 3-(phenoxycarbonylamino-methyl)-3,5,5-trimethylcyclohexylcarbamic acid phenyl ester formed at a yield of 98.7%.

The line 14 was opened, and the reaction solution (5) was transported to the reservoir 105 through the line 14.

Step (5-2): Thermal decomposition of 3-(phenoxycarbonylamino-methyl)-3,5,5-trimethylcyclohexylcarbamic acid phenyl ester and separation and collection of isocyanate Reactions were performed using the apparatus shown in FIG. 2.

Thermal decomposition was performed in the same way as in Step (2-2) of Example 2 to obtain a mixture (5) containing an isocyanate and a hydroxy compound except that the 3-(phenoxycarbonylamino-methyl)-3,5,5-trimethylcyclohexylcarbamic acid phenyl ester obtained in Step (5-1) was used.

Moreover, the separation and collection of the isocyanate were performed in the same way as in Step (2-2) of Example 2 except that tributylamine (manufactured by TOKYO CHEMICAL INDUSTRY CO., LTD., Japan) was supplied at 0.3 kg/hr instead of 1,3,5-triethylbenzene. A gas discharged from the top of the continuous multi-stage distillation column 205 was condensed in the condenser 206 through the line 30 and continuously extracted to the reservoir 209 through the line 32. The solution extracted through the line 32 was a solution containing approximately 98.4 wt % of isophorone diisocyanate and containing approximately 0.2 wt % of light boiling compounds presumed to be derived from tributylamine. The yield with respect to 3-aminomethyl-3,5,5-trimethylcyclohexylamine was 89.8%.

Incidentally, in the case where the normal boiling point of isophorone diisocyanate is defined as Tb and the normal boiling point of the hydroxy compound is defined as Ta, a normal boiling point Tc of tributylamine satisfied Ta<Tc<Tb.

Example 6

Step (6-1): Production of N,N'-(4,4'-methanediyl-diphenyl)-dicarbamic acid diphenyl ester Reactions were performed using the apparatus shown in FIG. 1.

Reactions were performed in the same way as in Step (1-1) of Example 1 except that: the amount of diphenyl carbonate used was set to 9.42 kg (44.4 mol); the amount of phenol used was set to 10.5 kg (112 mol); and 3.97 kg (20.0 mol) of 4,4'-methylenedianiline was used instead of hexamethylenediamine.

As a result of analyzing the solution after reaction (hereinafter, also referred to as "reaction solution (6)") by liquid chromatography, N,N'-(4,4'-methanediyl-diphenyl)-dicarbamic acid diphenyl ester formed at a yield of 96.8%.

The line 14 was opened, and the reaction solution (6) was transported to the reservoir 105 through the line 14.

Step (6-2): Thermal decomposition of N,N'-(4,4'-methanediyl-diphenyl)-dicarbamic acid diphenyl ester and separation and collection of isocyanate Reactions were performed using the apparatus shown in FIG. 2.

Diethyl phthalate (manufactured by TOKYO CHEMICAL INDUSTRY CO., LTD., Japan) was supplied to the bottom of the continuous multi-stage distillation column 202, and the total reflux operation of diethyl phthalate was performed with a pressure at the top of the column set to approximately 0.2 kPa. The quantity of heat necessary for the evaporation of diethyl phthalate was supplied by circulating the solution of the lower part of the column through the lines 26 and 28 and the reboiler 204.

Thermal decomposition was performed in the same way as in Step (2-2) of Example 2 to obtain a mixture (6) containing an isocyanate and a hydroxy compound except that the N,N'-(4,4'-methanediyl-diphenyl)-dicarbamic acid diphenyl ester obtained in Step (6-1) was used.

Moreover, the separation and collection of the isocyanate were performed in the same way as in Step (2-2) of Example 2 except that diethyl phthalate was supplied at 0.5 kg/hr instead of 1,3,5-triethylbenzene. A gas discharged from the top of the continuous multi-stage distillation column 205 was condensed in the condenser 206 through the line 30 and continuously extracted to the reservoir 209 through the line 32. The solution extracted through the line 32 was a solution containing approximately 98.2 wt % of diphenylmethane diisocyanate and containing approximately 0.8 wt % of light boiling compounds presumed to be derived from diethyl phthalate. The yield with respect to 4,4'-methylenedianiline was 87.4%.

Incidentally, in the case where the normal boiling point of diphenylmethane diisocyanate is defined as Tb and the normal boiling point of the hydroxy compound is defined as Ta, a normal boiling point Tc of diethyl phthalate satisfied Ta<Tc<Tb.

Example 7

Step (7-1): Production of toluene-2,4-dicarbamic acid diphenyl ester

Reactions were performed using the apparatus shown in FIG. 1.

Reactions were performed in the same way as in Step (1-1) of Example 1 except that: the amount of diphenyl carbonate used was set to 17.9 kg (83.5 mol); the amount of phenol used was set to 18.0 kg (192 mol); and 3.93 kg (32.1 mol) of 2,4-toluenediamine was used instead of hexamethylenediamine.

As a result of analyzing the solution after reaction (hereinafter, also referred to as a "reaction solution (7)") by liquid chromatography, toluene-2,4-dicarbamic acid diphenyl ester formed at a yield of 94.4%.

The line 14 was opened, and the reaction solution (7) was transported to the reservoir 105 through the line 14.

Step (7-2): Thermal decomposition of toluene-2,4-dicarbamic acid diphenyl ester and separation and collection of isocyanate Reactions were performed using the apparatus shown in FIG. 2.

1,3,5-Triethylbenzene (manufactured by TOKYO CHEMICAL INDUSTRY CO., LTD., Japan) was supplied to the bottom of the continuous multi-stage distillation column 202, and the total reflux operation of 1,3,5-triethylbenzene was performed with a pressure at the top of the column set to approximately 0.2 kPa. The quantity of heat necessary for the evaporation of 1,3,5-triethylbenzene was supplied by circulating the solution of the lower part of the column through the lines 26 and 28 and the reboiler 204.

Thermal decomposition was performed in the same way as in Step (2-2) of Example 2 to obtain a mixture (7) containing an isocyanate and a hydroxy compound except that the toluene-2,4-dicarbamic acid diphenyl ester obtained in Step (7-1) was used.

Moreover, the separation and collection of the isocyanate were performed in the same way as in Step (2-2) of Example 2 except that 1,3,5-triethylbenzene was supplied at 0.2 kg/hr. A gas discharged from the top of the continuous multi-stage distillation column 205 was condensed in the condenser 206 through the line 30 and continuously extracted to the reservoir 209 through the line 32. The solution extracted through the line 32 was a solution containing approximately 99.2 wt % of 2,4-tolylene diisocyanate. The yield with respect to 2,4-toluenediamine was 86.0%.

Incidentally, in the case where the normal boiling point of 2,4-tolylene diisocyanate is defined as Tb and the normal boiling point of the hydroxy compound is defined as Ta, a normal boiling point Tc of 1,3,5-triethylbenzene satisfied Ta<Tc<Tb.

Example 8

Step (8-1): Production of N,N'-hexanediyl-dicarbamic acid diphenyl ester

Reactions were performed using the apparatus shown in FIG. 1.

A reaction solution containing N,N'-hexanediyl-dicarbamic acid diphenyl ester (hereinafter, also referred to as a "reaction solution (8)") was obtained by performing the same method as in Step (1-1) of Example 1 except that 13.5 kg (63.7 mol) of diphenyl carbonate, 13.8 kg (149 mol) of phenol, and 3.22 kg (27.7 mol) of hexamethylenediamine were used. As a result of analyzing the reaction solution (8) by liquid chromatography, N,N'-hexanediyl-dicarbamic acid diphenyl ester formed at a yield of 99.5%.

Step (8-2): Thermal decomposition of N,N'-hexanediyl-dicarbamic acid diphenyl ester and separation and collection of isocyanate Reactions were performed using the apparatus shown in FIG. 2.

Decamethyltetrasiloxane (manufactured by TOKYO CHEMICAL INDUSTRY CO., LTD., Japan) was used instead of n-dodecane to perform the total reflux operation of decamethyltetrasiloxane with a pressure at the top of the column set to 0.5 kPa.

The thin-film distillation apparatus 201 of 0.1 $m^2$ in heat transfer area was heated to 220° C., and the internal pressure was set to approximately 1.3 kPa. The reaction solution collected into the reservoir 105 in Step (8-1) was heated to 150° C. and supplied at approximately 1.0 kg/hr to the upper part of the thin-film distillation apparatus 201 through the line 21, and the thermal decomposition of N,N'-hexanediyl-dicarbamic acid diphenyl ester was performed to thereby obtain a mixture containing an isocyanate and a hydroxy compound. Liquid-phase components were extracted through the line 23 from the bottom of the thin-film distillation apparatus 201 and circulated to the upper part of the thin-film distillation apparatus 201 through the line 24 and the line 21. The mixture was extracted as gas-phase components through the line 22.

The mixture, which was gas-phase components, extracted through the line 22 from the thin-film distillation apparatus 201 was continuously fed to the intermediate stage of the continuous multi-stage distillation column 202, and at the same time, decamethyltetrasiloxane was supplied at 0.3 kg/hr through the line 29 from the reservoir 210 to perform the distillation separation of the mixture which was gas-phase components. The quantity of heat necessary for the distillation separation was supplied by circulating the solution of the lower part of the column through the lines 26 and 28 and the reboiler 204. A solution temperature at the bottom of the continuous multi-stage distillation column 202 was 150° C., and a pressure at the top of the column was approximately 15 kPa. A gas discharged from the top of the continuous multi-stage distillation column 202 was condensed in the condenser 203 through the line 25 and continuously extracted through the line 27. On the other hand, liquid-phase components were extracted through the line 26 from the bottom of the column and supplied to the distillation column 205.

The liquid-phase components extracted through the line 26 were continuously fed to the intermediate stage of the continuous multi-stage distillation column 205 of approximately 5 cm in inside diameter filled with Dixon packing (6 mmφ) to perform the distillation separation of the liquid-phase components. The quantity of heat necessary for the distillation separation was supplied by circulating the solution of the lower part of the column through the lines 31 and 33 and the reboiler 207. A solution temperature at the bottom of the continuous multi-stage distillation column 205 was 150° C., and a pressure at the top of the column was approximately 1.5 kPa. A gas discharged from the top of the continuous multi-stage distillation column 205 was condensed in the condenser 206 through the line 30 and continuously extracted to the reservoir 209 through the line 32. The solution extracted through the line 32 was a solution containing approximately 99.8 wt % of hexamethylene diisocyanate. The yield with respect to hexamethylenediamine was 87.1%.

Incidentally, in the case where the normal boiling point of hexamethylene diisocyanate is defined as Tb and the normal boiling point of the hydroxy compound is defined as Ta, a normal boiling point Tc of decamethyltetrasiloxane satisfied Ta<Tc<Tb.

Example 9

Figure 3:
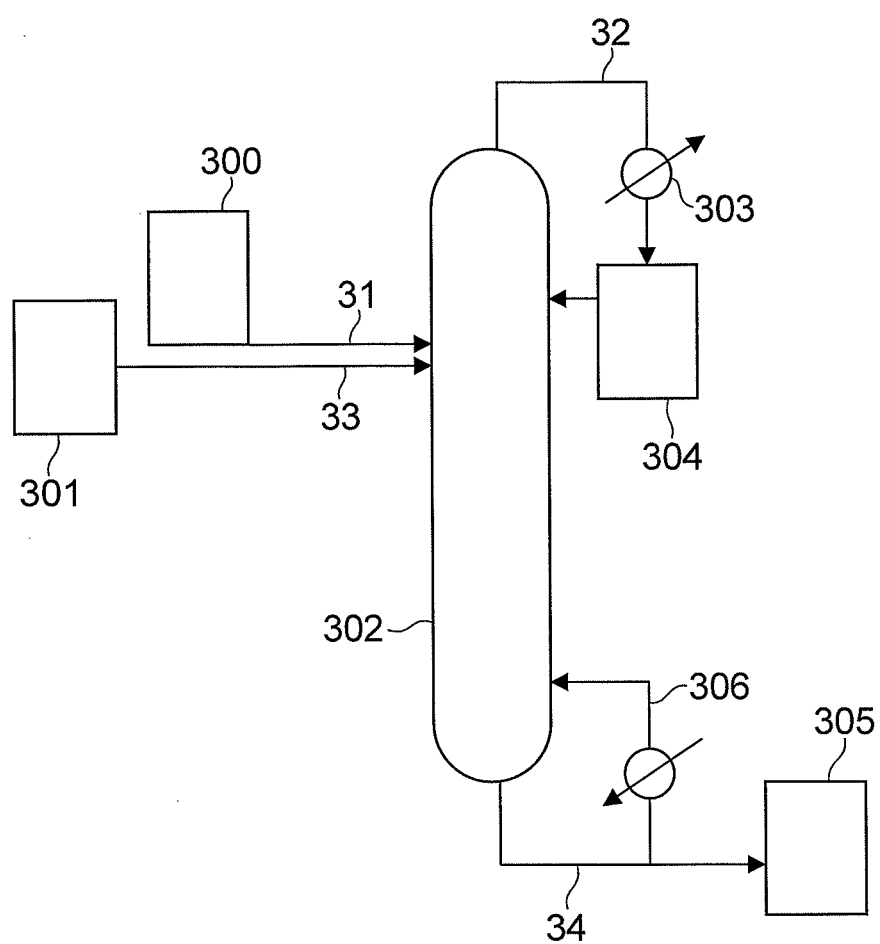
FIG. 3 is an illustrative diagram showing one example of an N-substituted carbamic acid ester producing apparatus.

Step (9-1): Production of N,N-hexanediyl-dicarbamic acid di(4-(1,1,3,3-tetramethylbutyl)phenyl) ester Step (9-1) was carried out using an apparatus shown in FIG. 3.

2.4 kg of hexamethylenediamine, 85.10 kg of 4-(1,1,3,3-tetramethylbutyl)phenol (manufactured by TOKYO CHEMICAL INDUSTRY CO., LTD., Japan), and 4.96 kg of urea (manufactured by Wako Pure Chemical Industries, Ltd., Japan, special grade) were mixed to prepare a raw material solution. A packed column 302 of 20 mm in inside diameter filled with a packing material (HELIPACK No. 3) was heated to 240° C., and the internal pressure of the packed column 302 was set to approximately 20 kPa. A mixed solution of the same composition as in the raw material solution was introduced to the inside of the packed column 302 through a line 31 connected with the side of the upper part of the packed column 302. After the operation conditions stabilized, the raw material solution was introduced at approximately 1.0 g/min to the inside of the packed column 302 through a line 33 and reacted. The reaction solution was collected into a reservoir 305 by way of a line 34 connected with the bottommost part of the packed column 302. Moreover, gas-phase components were collected through a line 32 connected with the topmost part of the packed column 302 and condensed in a condenser 303 kept at approximately 85° C., and the obtained components were collected into a reservoir 304. The reaction solution collected into the reservoir 305 was 46.9 kg. As a result of analyzing this reaction solution by liquid chromatography and $^1$H-NMR, N,N'-hexanediyl-dicarbamic acid di(4-(1,1,3,3-tetramethylbutyl)phenyl) ester formed at a yield of approximately 92% with respect to hexamethylenediamine in this reaction solution.

Figure 4:
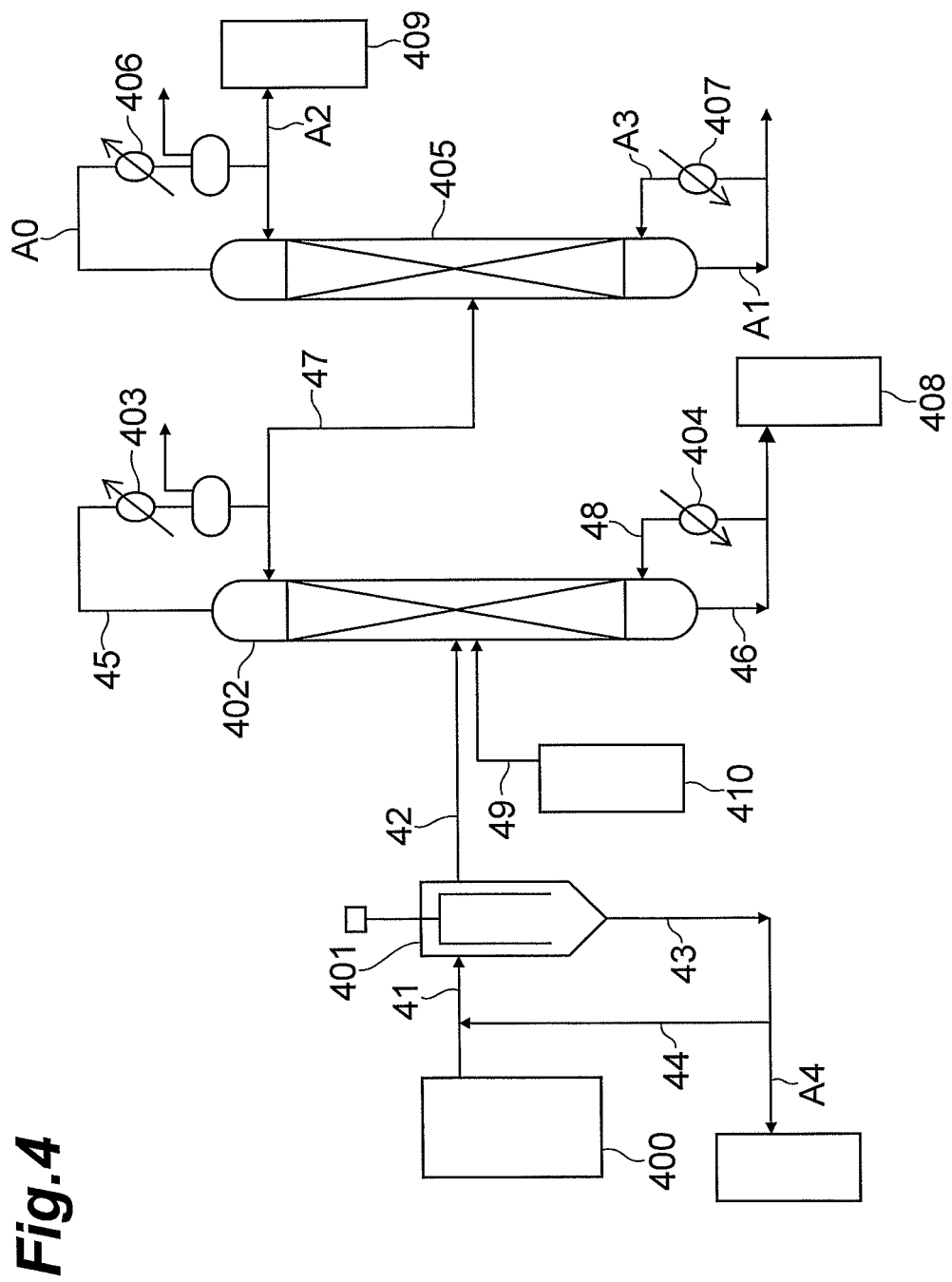
FIG. 4 is a conceptual diagram showing one example of an N-substituted carbamic acid ester thermally decomposing apparatus and an isocyanate separating apparatus.

Step (9-2): Thermal decomposition of N,N'-hexanediyl-dicarbamic acid di(4-(1,1,3,3-tetramethylbutyl)phenyl) ester and separation and collection of isocyanate Step (9-2) was carried out using an apparatus shown in FIG. 4.

A thin-film distillation apparatus 401 was heated to 280° C., and the internal pressure was set to approximately 1.0 kPa. The reaction solution collected into the reservoir 305 in Step (9-1) was heated to 150° C. and supplied at approximately 1.0 kg/hr to the thin-film distillation apparatus 401 through a line 41 connected with the side of the upper part of the thin-film distillation apparatus 401 to perform the thermal decomposition of N,N'-hexanediyl-dicarbamic acid di(4-(1,1,3,3-tetramethylbutyl)phenyl) ester. By this thermal decomposition, a mixture (9) containing an isocyanate and a hydroxy compound was obtained. Incidentally, liquid-phase components were extracted through a line 43 connected with the bottom of the thin-film distillation apparatus 401, introduced to the upper part of the thin-film distillation apparatus 401 through a line 44 and the line 41, and circulated. The mixture (9) was extracted as gas-phase components through a line 42.

The mixture (9), which was gas-phase components, extracted through the line 42 from the thin-film distillation apparatus 401 was continuously fed to the intermediate stage of the continuous multi-stage distillation column 402, and at the same time, n-pentadecane (manufactured by TOKYO CHEMICAL INDUSTRY CO., LTD., Japan) was supplied through a line 49 from a reservoir 410 to perform the distillation separation of the mixture (9) which was gas-phase components. The quantity of heat necessary for the distillation separation was supplied by circulating the solution of the lower part of the column through lines 46 and 48 and a reboiler 404. A pressure at the top of the column was approximately 5 kPa. A gas discharged from the top of the continuous multi-stage distillation column 402 was condensed into liquid-phase components in a condenser 403 through a line 45, continuously extracted through a line 47, and supplied to a continuous multi-stage distillation column 405. Gas components and liquid components at both the upper and lower first theoretical plates relative to the position of line 42 of the continuous multi-stage distillation column 402 were analyzed at steady state, and operation was performed such that all contained 10 wt % or more of n-pentadecane.

The liquid-phase components extracted through the line 47 were continuously fed to the intermediate stage of the continuous multi-stage distillation column 405 to perform the distillation separation of the liquid-phase components. The quantity of heat necessary for the distillation separation was supplied by circulating the solution of the lower part of the column through lines A1 and A3 and a reboiler 407. A gas discharged from the top of the continuous multi-stage distillation column 405 was condensed in a condenser 406 through a line A0 and continuously extracted to a reservoir 409 through a line A2.

The solution extracted through the line A2 was a solution containing approximately 99 wt % of hexamethylene diisocyanate. The yield with respect to hexamethylenediamine was 90.0%.

Incidentally, in the case where the normal boiling point of hexamethylene diisocyanate is defined as Tb and the normal boiling point of the hydroxy compound is defined as Ta, a normal boiling point Tc of n-pentadecane satisfied Tb<Tc<Ta.

Example 10

Step (10-1): Production of Compound Having Ureido Group

Figure 5:
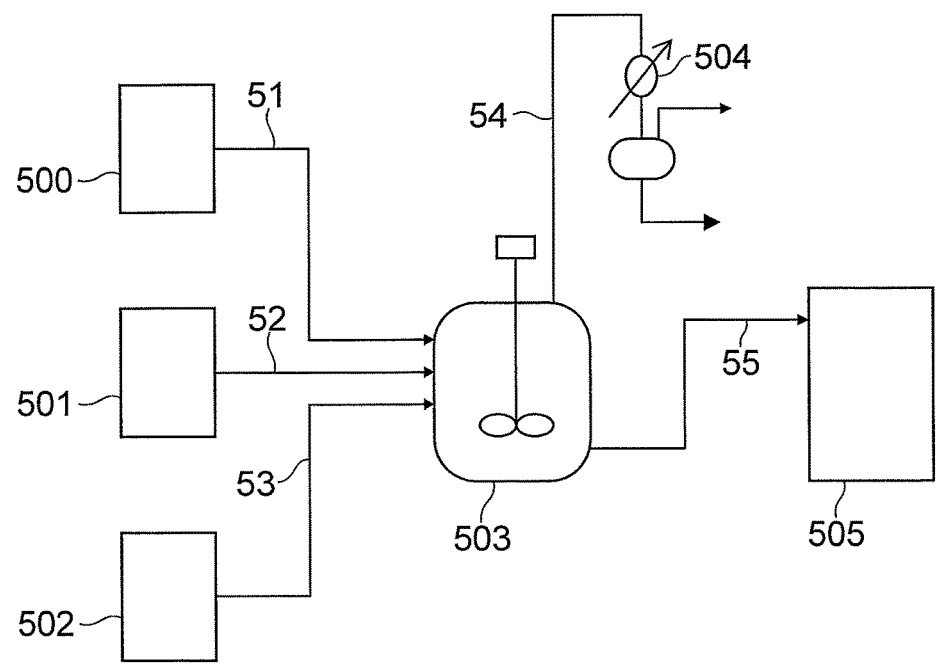
FIG. 5 is an illustrative diagram showing one example of a production apparatus for compounds having an ureido group.

Step (10-1) was carried out using an apparatus shown in FIG. 5.

In the state where a line 55 was closed, 66.0 kg of 4-(α,α-dimethylbenzyl)phenol (manufactured by Wako Pure Chemical Industries, Ltd., Japan) from a reservoir 500 and 7.0 kg of urea from a reservoir 501 were fed to a stirred tank 503. The stirred tank 503 was heated to 100° C., and stirring was initiated. 3.3 kg of hexamethylenediamine was supplied at approximately 0.1 kg/min from a reservoir 502 through a line 53 to the stirred tank 503. After the completion of supply of hexamethylenediamine, stirring was done for approximately 2 hours, and the reaction solution was sampled. As a result of analyzing this reaction solution by liquid chromatography, 1,6-hexanediurea formed. The reaction solution was transported to a reservoir 505.

Step (10-2): Production of N,N-hexanediyl-dicarbamic acid di(4-(α,α-dimethylbenzyl)phenyl) ester Step (10-2) was carried out using the apparatus shown in FIG. 3.

Step (10-2) was performed in the same way as in Step (9-1) of Example 9 except that: the reaction solution collected into the reservoir 505 in Step (10-1) was used instead of the raw material solution containing hexamethylenediamine, 4-(1,1,3,3-tetramethylbutyl)phenol, and urea; and the packed column 302 was heated to 240° C., and the internal pressure was set to approximately 5 kPa. The reaction solution collected into the reservoir 305 was 70.0 kg. As a result of analyzing this reaction solution by liquid chromatography and $^1$H-NMR, N,N'-hexanediyl-dicarbamic acid di(4-(α,α-dimethylbenzyl)phenyl) ester formed at a yield of approximately 95% with respect to hexamethylenediamine in this reaction solution.

Step (10-3): Thermal decomposition of N,N'-hexanediyl-dicarbamic acid di(4-(α,α-dimethylbenzyl)phenyl) ester and separation and collection of isocyanate Step (10-3) was performed in the same way as in Step (9-2) of Example 9 except that: the thin-film distillation apparatus 401 was heated to 280° C., and the internal pressure was set to approximately 5 kPa; the reaction solution collected into the reservoir 305 in Step (10-2) was heated to 150° C. and supplied at approximately 2.0 kg/hr to the thin-film distillation apparatus 401 through the line 41; and benzyltoluene (isomeric mixture) was supplied instead of n-pentadecane. A gas discharged from the top of the continuous multi-stage distillation column 405 was condensed in the condenser 406 through the line A0 and continuously extracted to the reservoir 409 through the line A2.

The solution extracted through the line A2 was a solution containing approximately 99 wt % of hexamethylene diisocyanate. The yield with respect to hexamethylenediamine was 96.5%.

Incidentally, in the case where the normal boiling point of hexamethylene diisocyanate is defined as Tb and the normal boiling point of the hydroxy compound is defined as Ta, a normal boiling point Tc of benzyltoluene satisfied Tb<Tc<Ta.

Example 11

Step (11-1): Production of Compound Having Ureido Group

A reaction solution containing 1,6-hexanediurea was obtained by performing the same method as in Step (10-1) of Example 10, and the reaction solution was transported to the reservoir 505.

Step (11-2): Production of N,N'-hexanediyl-dicarbamic acid di(4-(α,α-dimethylbenzyl)phenyl) ester A reaction solution containing N,N'-hexanediyl-dicarbamic acid di(4-(α,α-dimethylbenzyl)phenyl) ester was obtained by performing the same method as in Step (10-2) of Example 10. The yield of N,N'-hexanediyl-dicarbamic acid di(4-(α,α-dimethylbenzyl)phenyl) ester with respect to hexamethylenediamine was approximately 95%.

Step (11-3): Thermal decomposition of N,N'-hexanediyl-dicarbamic acid di(4-(α,α-dimethylbenzyl)phenyl) ester and separation and collection of isocyanate The same method as in Step (10-3) of Example 10 was performed except that diphenyl sulfide (manufactured by TOKYO CHEMICAL INDUSTRY CO., LTD., Japan) was used instead of benzyltoluene (isomeric mixture). A gas discharged from the top of the continuous multi-stage distillation column 405 was condensed in the condenser 406 through the line A0 and continuously extracted to the reservoir 409 through the line A2.

The solution extracted through the line A2 was a solution containing approximately 97 wt % of hexamethylene diisocyanate and containing approximately 0.3 wt % of light boiling compounds presumed to be derived from diphenyl sulfide. The yield with respect to hexamethylenediamine was 92.2%.

Incidentally, in the case where the normal boiling point of hexamethylene diisocyanate is defined as Tb and the normal boiling point of the hydroxy compound is defined as Ta, a normal boiling point Tc of diphenyl sulfide satisfied Tb<Tc<Ta.

Example 12

Step (12-1): Production of Compound Having Ureido Group

Step (12-1) was performed in the same way as in Step (10-1) of Example 10 to obtain a reaction solution containing 3-(ureidomethyl)-3,5,5-trimethylcyclohexylurea except that: 1.0 kg of 3-aminomethyl-3,5,5-trimethylcyclohexylamine was used instead of hexamethylenediamine; 10.0 kg of 4-phenylphenol was used instead of 4-(α,α-dimethylbenzyl)phenol; and 1.42 kg of urea was used.

Step (12-2): Production of 3-((4-phenylphenoxy)carbonylamino-methyl)-3,5,5-trimethylcyclohexyl carbamic acid (4-phenylphenyl) ester Step (12-2) was performed in the same way as in Step (9-1) of Example 9 except that: the reaction solution obtained in Step (12-1) was used instead of the raw material solution containing hexamethylenediamine, 4-(1,1,3,3-tetramethylbutyl)phenol, and urea; and the packed column 302 was heated to 220° C., and the internal pressure of the packed column 302 was set to approximately 3 kPa. The reaction solution collected into the reservoir 305 was 12.4 kg. As a result of analyzing this reaction solution by liquid chromatography and $^1$H-NMR, 3-((4-phenylphenoxy)carbonylamino-methyl)-3,5,5-trimethylcyclohexyl carbamic acid (4-phenylphenyl) ester formed at a yield of approximately 92% with respect to 3-aminomethyl-3,5,5-trimethylcyclohexylamine in this reaction solution.

Step (12-3): Thermal decomposition of 3-((4-phenylphenoxy)carbonylamino-methyl)-3,5,5-trimethylcyclohexyl carbamic acid (4-phenylphenyl) ester and separation and collection of isocyanate Step (12-3) was performed in the same way as in Step (9-2) of Example 9 except that: the thin-film distillation apparatus 401 was heated to 280° C., and the internal pressure was set to approximately 3 kPa; the reaction solution collected into the reservoir 305 in Step (12-2) was heated to 120° C. and supplied at approximately 2.0 kg/hr to the upper part of the thin-film distillation apparatus 401 through the line 41; and dibenzyl ether was supplied instead of n-pentadecane. A gas discharged from the top of the continuous multi-stage distillation column 405 was condensed in the condenser 406 through the line A0 and continuously extracted to the reservoir 409 through the line A2.

The solution extracted through the line A2 was a solution containing approximately 98 wt % of isophorone diisocyanate and containing approximately 0.8 wt % of light boiling compounds presumed to be derived from dibenzyl ether. The yield with respect to 3-aminomethyl-3,5,5-trimethylcyclohexylamine was approximately 88.3%.

Incidentally, in the case where the normal boiling point of isophorone diisocyanate is defined as Tb and the normal boiling point of the hydroxy compound is defined as Ta, a normal boiling point Tc of dibenzyl ether satisfied Tb<Tc<Ta.

Example 13

Figure 6:
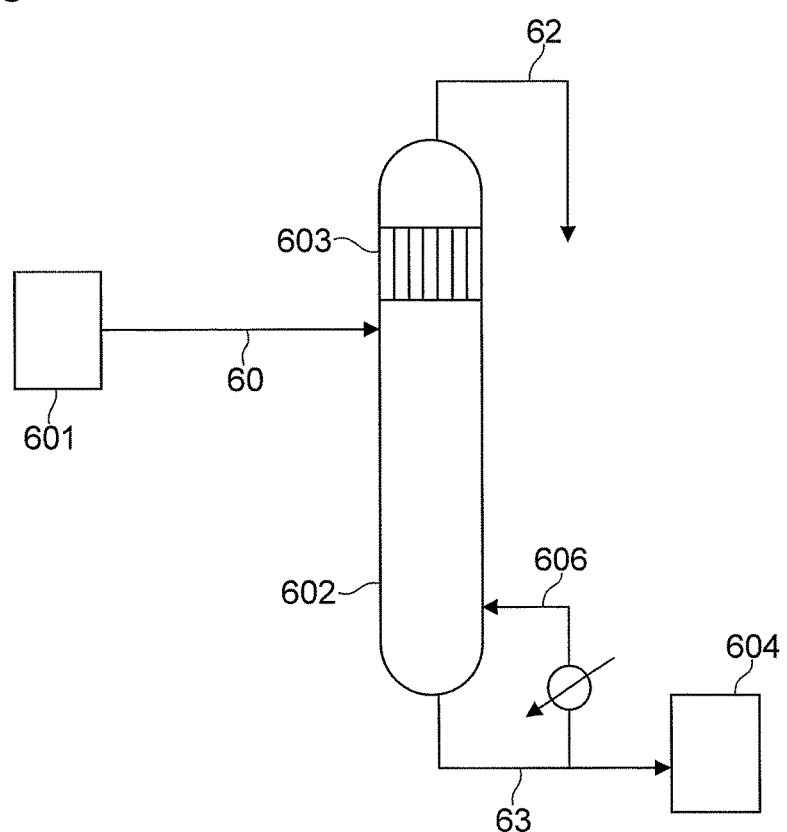
FIG. 6 is an illustrative diagram showing one example of an N-substituted carbamic acid ester producing apparatus.

Step (13-1): Production of 3-(phenoxycarbonylamino-methyl)-3,5,5-trimethylcyclohexylcarbamic acid phenyl ester Step (13-1) was carried out using an apparatus shown in FIG. 6.

8.80 kg of 3-aminomethyl-3,5,5-trimethylcyclohexylamine, 97.1 kg of phenol, and 7.70 kg of urea were mixed to prepare a raw material solution. A packed column 602 was heated to 220° C., and a mixed solution of the same composition as in the raw material solution was introduced to the inside of the packed column 602 through a line 60 connected with the side of the upper part of the packed column 602. After the operation conditions stabilized, the raw material solution was introduced at approximately 1.0 g/min to the inside of the packed column 602 through the line 60 and reacted. The reaction solution was collected into a reservoir 604 by way of a line 63 connected with the bottommost part of the packed column 602. The internal pressure was approximately 0.2 MPa. Ammonia that formed was extracted through a line 62 connected with the topmost part of the packed column 602. The reaction solution collected into the reservoir 604 was 11.2 kg. As a result of analyzing this reaction solution by liquid chromatography and $^1$H-NMR, 3-(phenoxycarbonylamino-methyl)-3,5,5-trimethylcyclohexylcarbamic acid phenyl ester formed at a yield of approximately 94% with respect to 3-aminomethyl-3,5,5-trimethylcyclohexylamine in this reaction solution.

Step (13-2): Thermal decomposition of 3-(phenoxycarbonylamino-methyl)-3,5,5-trimethylcyclohexylcarbamic acid phenyl ester and separation and collection of isocyanate Step (13-2) was carried out using the apparatus shown in FIG. 2.

The thin-film distillation apparatus 201 was heated to 280° C., and the internal pressure was set to approximately 10 kPa. The reaction solution collected into the reservoir 604 in Step (13-1) was heated to 100° C. and supplied at approximately 1.0 kg/hr to the thin-film distillation apparatus 201 through the line 21 connected with the side of the upper part of the thin-film distillation apparatus 201 to perform the thermal decomposition of 3-(phenoxycarbonylamino-methyl)-3,5,5-trimethylcyclohexylcarbamic acid phenyl ester. By this thermal decomposition, a mixture (13) containing an isocyanate and a hydroxy compound was obtained. Incidentally, liquid-phase components were extracted through the line 23 connected with the bottom of the thin-film distillation apparatus 201, introduced to the upper part of the thin-film distillation apparatus 201 through the line 24 and the line 21, and circulated. The mixture (13) was extracted as gas-phase components through the line 22.

The gas-phase components extracted through the line 22 from the thin-film distillation apparatus 201 were continuously fed to the intermediate stage of the continuous multi-stage distillation column 202, and at the same time, 4-methylbenzyl chloride (manufactured by TOKYO CHEMICAL INDUSTRY CO., LTD., Japan) was supplied through the line 29 from the reservoir 210 to perform the distillation separation of the mixture (13) which was gas-phase components. The quantity of heat necessary for the distillation separation was supplied by circulating the solution of the lower part of the column through the lines 26 and 28 and the reboiler 204. A pressure at the top of the column was approximately 5 kPa. Liquid-phase components distilled from the bottom of the continuous multi-stage distillation column 202 were continuously extracted through the line 26 and supplied to the continuous multi-stage distillation column 205. Gas components and liquid components at both the upper and lower second theoretical plates relative to the position of line 22 of the continuous multi-stage distillation column 202 were analyzed at steady state, and operation was performed such that all contained 30 wt % or more of 4-methylbenzyl chloride.

The liquid-phase components extracted through the line 26 were continuously fed to the intermediate stage of the continuous multi-stage distillation column 205 of approximately 5 cm in inside diameter filled with Dixon packing (6 mmφ) to perform the distillation separation of the liquid-phase components. The quantity of heat necessary for the distillation separation was supplied by circulating the solution of the lower part of the column through the lines 31 and 33 and the reboiler 207. A solution temperature at the bottom of the continuous multi-stage distillation column 205 was 160° C., and a pressure at the top of the column was approximately 1.5 kPa. A gas discharged from the top of the continuous multi-stage distillation column 205 was condensed in the condenser 206 through the line 30 and continuously extracted to the reservoir 209 through the line 32.

The solution extracted through the line 32 was a solution containing approximately 99 wt % of isophorone diisocyanate. The yield with respect to 3-aminomethyl-3,5,5-trimethylcyclohexylamine was approximately 87.4%. Moreover, the obtained isophorone diisocyanate contained 10 ppm chlorine components.

Incidentally, in the case where the normal boiling point of isophorone diisocyanate is defined as Tb and the normal boiling point of the hydroxy compound is defined as Ta, a normal boiling point Tc of 4-methylbenzyl chloride satisfied Ta<Tc<Tb.

Example 14

Step (14-1): Production of Compound Having Ureido Group

Step (14-1) was performed in the same way as in Step (10-1) of Example 10 to obtain a reaction solution containing 4,4'-methylenebis(cyclohexylurea) except that 3.40 kg (16.2 mol) of 4,4'-methylenebis(cyclohexylamine) (manufactured by Sigma-Aldrich Corp., USA) was used instead of hexamethylenediamine, 73.0 kg (486 mol) of 4-tert-butylphenol was used instead of 4-(α,α-dimethylbenzyl)phenol, and 3.89 kg (64.8 mol) of urea was used.

Step (14-2): Production of N,N'-(4,4'-methanediyl-dicyclohexyl)-dicarbamic acid di(4-tert-butylphenyl) ester Step (14-2) was performed in the same way as in Step (9-1) of Example 9 to collect a reaction solution into the reservoir 305 except that: the reaction solution obtained in Step (14-1) was used instead of the raw material solution containing hexamethylenediamine, 4-(1,1,3,3-tetramethylbutyl)phenol, and urea; and the packed column 302 was heated to 220° C., and the internal pressure of the packed column 302 was set to approximately 3 kPa. As a result of analyzing this reaction solution by liquid chromatography and $^1$H-NMR, N,N'-(4,4'-methanediyl-dicyclohexyl)-dicarbamic acid di(4-tert-butylphenyl) ester formed at a yield of approximately 90% with respect to 4,4'-methylenebis(cyclohexylamine) in this reaction solution.

Step (14-3): Thermal decomposition of N,N'-(4,4'-methanediyl-dicyclohexyl)-dicarbamic acid di(4-tert-butylphenyl) ester and separation and collection of isocyanate The thermal decomposition of N,N'-(4,4'-methanediyl-dicyclohexyl)-dicarbamic acid di(4-tert-butylphenyl) ester was performed by performing the same method as in Step (13-2) of Example 13 except that: the thin-film distillation apparatus 201 was heated to 280° C., and the internal pressure was set to approximately 0.5 kPa; and the reaction solution obtained in Step (14-2) was used instead of the reaction solution collected into the reservoir 604 in Step (13-1) and supplied at approximately 1.2 kg/hr to the thin-film distillation apparatus 201 through the line 21 connected with the side of the upper part of the thin-film distillation apparatus 201.

By this thermal decomposition, a mixture (14) containing an isocyanate and a hydroxy compound was obtained. Incidentally, liquid-phase components were extracted through the line 23 connected with the bottom of the thin-film distillation apparatus 201, introduced to the upper part of the thin-film distillation apparatus 201 through the line 24 and the line 21, and circulated. The mixture (14) was extracted as gas-phase components through the line 22.

The gas-phase components extracted through the line 22 from the thin-film distillation apparatus 201 were continuously fed to the intermediate stage of the continuous multi-stage distillation column 202, and at the same time, fluorene (manufactured by TOKYO CHEMICAL INDUSTRY CO., LTD., Japan) was supplied through the line 29 from the reservoir 210 to perform the distillation separation of the mixture (14) which was gas-phase components. The quantity of heat necessary for the distillation separation was supplied by circulating the solution of the lower part of the column through the lines 26 and 28 and the reboiler 204. A pressure at the top of the column was approximately 5 kPa. Liquid-phase components distilled from the bottom of the continuous multi-stage distillation column 202 were continuously extracted through the line 26 and supplied to the continuous multi-stage distillation column 205. Gas components and liquid components at both the upper and lower third theoretical plates relative to the position of line 22 of the continuous multi-stage distillation column 202 were analyzed at steady state, and operation was performed such that all contained 30 wt % or more of fluorene.

The liquid-phase components extracted through the line 26 were continuously fed to the intermediate stage of the continuous multi-stage distillation column 205 to perform the distillation separation of the liquid-phase components. The quantity of heat necessary for the distillation separation was supplied by circulating the solution of the lower part of the column through the lines 31 and 33 and the reboiler 207. A solution temperature at the bottom of the continuous multi-stage distillation column 205 was 160° C., and a pressure at the top of the column was approximately 1.5 kPa. A gas discharged from the top of the continuous multi-stage distillation column 205 was condensed in the condenser 206 through the line 30 and continuously extracted to the reservoir 209 through the line 32.

The solution extracted through the line 32 was a solution containing approximately 99 wt % of dicyclohexylmethane diisocyanate. The yield with respect to 4,4'-methylenebis(cyclohexylamine) was approximately 81.5%.

Incidentally, in the case where the normal boiling point of dicyclohexylmethane diisocyanate is defined as Tb and the normal boiling point of the hydroxy compound is defined as Ta, a normal boiling point Tc of fluorene satisfied Ta<Tc<

Example 15

Step (15-1): Production of N,N'-(4,4'-methanediyl-dicyclohexyl)-dicarbamic acid di(4-ethylphenyl) ester A reaction solution was collected into the reservoir 604 by performing the same method as in Step (13-1) of Example 13 except that 4.50 kg (21.4 mol) of 4,4'-methylenebis(cyclohexylamine) was used instead of 3-aminomethyl-3,5,5-trimethylcyclohexylamine, 104.6 kg (856 mol) of 4-ethylphenol was used instead of phenol, and 2.70 kg (44.9 mol) of urea was used. As a result of analyzing this reaction solution by liquid chromatography and $^1$H-NMR, N,N'-(4,4'-methanediyl-dicyclohexyl)-dicarbamic acid di(4-ethylphenyl) ester formed at a yield of approximately 93% with respect to 4,4'-methylenebis(cyclohexylamine) in this reaction solution.

Step (15-2): Thermal decomposition of N,N'-(4,4'-methanediyl-dicyclohexyl)-dicarbamic acid di(4-ethylphenyl) ester and separation and collection of isocyanate The thermal decomposition of N,N'-(4,4'-methanediyl-dicyclohexyl)-dicarbamic acid di(4-ethylphenyl) ester was performed by performing the same method as in Step (13-2) of Example 13 except that: the thin-film distillation apparatus 201 was heated to 260° C., and the internal pressure was set to approximately 0.5 kPa; and the reaction solution obtained in Step (15-1) was used instead of the reaction solution collected into the reservoir 604 in Step (13-1) and supplied at approximately 2.0 kg/hr to the thin-film distillation apparatus 201 through the line 21 connected with the side of the upper part of the thin-film distillation apparatus 201. By this thermal decomposition, a mixture (15) containing an isocyanate and a hydroxy compound was obtained. Incidentally, liquid-phase components were extracted through the line 23 connected with the bottom of the thin-film distillation apparatus 201, introduced to the upper part of the thin-film distillation apparatus 201 through the line 24 and the line 21, and circulated. The mixture (15) was extracted as gas-phase components through the line 22.

Subsequently, 1-chlorododecane (manufactured by TOKYO CHEMICAL INDUSTRY CO., LTD., Japan) was used instead of 4-methylbenzyl chloride to perform the distillation separation of the mixture (15) which was gas-phase components. A pressure at the top of the column was approximately 0.1 kPa. Liquid-phase components distilled from the bottom of the continuous multi-stage distillation column 202 were continuously extracted through the line 26 and supplied to the continuous multi-stage distillation column 205. Gas components and liquid components at both the upper and lower third theoretical plates relative to the position of line 22 of the continuous multi-stage distillation column 202 were analyzed at steady state, and operation was performed such that all contained 30 wt % or more of 1-chlorododecane.

The liquid-phase components extracted through the line 26 were continuously fed to the intermediate stage of the continuous multi-stage distillation column 205 to perform the distillation separation of the liquid-phase components. The quantity of heat necessary for the distillation separation was supplied by circulating the solution of the lower part of the column through the lines 31 and 33 and the reboiler 207. A solution temperature at the bottom of the continuous multi-stage distillation column 205 was 160° C., and a pressure at the top of the column was approximately 1.5 kPa. A gas discharged from the top of the continuous multi-stage distillation column 205 was condensed in the condenser 206 through the line 30 and continuously extracted to the reservoir 209 through the line 32.

The solution extracted through the line 32 was a solution containing approximately 99 wt % of dicyclohexylmethane diisocyanate. The yield with respect to 4,4'-methylenebis (cyclohexylamine) was approximately 85.0%. Moreover, the obtained dicyclohexylmethane diisocyanate contained approximately 5 ppm chlorine components.

Incidentally, in the case where the normal boiling point of dicyclohexylmethane diisocyanate is defined as Tb and the normal boiling point of the hydroxy compound is defined as Ta, a normal boiling point Tc of 1-chlorododecane satisfied Ta<Tc<Tb.

Example 16

Step (16-1): Production of toluene-2,4-dicarbamic acid di(4-dodecylphenyl) ester A reaction solution was collected into the reservoir 305 by performing the same method as in Step (9-1) of Example 9 except that 5.53 kg (45.3 mol) of 2,4-toluenediamine was used instead of hexamethylenediamine, 237.7 kg (906 mol) of 4-dodecylphenol was used instead of 4-(1,1,3,3-tetramethylbutyl)phenol, and 8.15 kg (136 mol) of urea was used. As a result of analyzing this reaction solution by liquid chromatography and $^1$H-NMR, toluene-2,4-dicarbamic acid di(4-dodecylphenyl) ester formed at a yield of approximately 90% with respect to 2,4-toluenediamine in this reaction solution.

Step (16-2): Thermal decomposition of toluene-2,4-dicarbamic acid di(4-dodecylphenyl) ester and separation and collection of isocyanate Step (16-2) was performed in the same way as in Step (9-2) of Example 9 except that the thin-film distillation apparatus 401 was heated to 220° C., and the internal pressure was set to approximately 0.3 kPa; the reaction solution collected into the reservoir 305 in Step (16-1) was heated to 150° C. and supplied at approximately 2.0 kg/hr to the thin-film distillation apparatus 401 through the line 41; and n-pentadecane was supplied at approximately 0.5 kg/hr through the line 49. A gas discharged from the top of the continuous multi-stage distillation column 405 was condensed in the condenser 406 through the line A0 and continuously extracted to the reservoir 409 through the line A2.

The solution extracted through the line A2 was a solution containing approximately 99 wt % of 2,4-tolylene diisocyanate. The yield with respect to 2,4-toluenediamine was 88.3%.

Incidentally, in the case where the normal boiling point of 2,4-tolylene diisocyanate is defined as Tb and the normal boiling point of the hydroxy compound is defined as Ta, a normal boiling point Tc of n-pentadecane satisfied Tb<Tc<Ta.

Example 17

Step (17-1): Production of N,N'-(4,4'-methanediyl-diphenyl)-dicarbamic acid di(4-tert-amylphenyl) ester A reaction solution was collected into the reservoir 604 by performing the same method as in Step (13-1) of Example 13 except that 1.64 kg (8.27 mol) of 4,4'-methylenedianiline was used instead of 3-aminomethyl-3,5,5-trimethylcyclohexylamine, 34.0 kg (207 mol) of 4-tert-amylphenol was used instead of phenol, and 1.99 kg (33.1 mol) of urea was used. As a result of analyzing this reaction solution by liquid chromatography and $^1$H-NMR, N,N'-(4,4'-methanediyl-diphenyl)-dicarbamic acid di(4-tert-amylphenyl) ester formed at a yield of approximately 92% with respect to 4,4'-methylenedianiline in this reaction solution.

Step (17-2): Thermal decomposition of N,N'-(4,4'-methanediyl-diphenyl)-dicarbamic acid di(4-tert-amylphenyl) ester and separation and collection of isocyanate The thermal decomposition of N,N'-(4,4'-methanediyl-diphenyl)-dicarbamic acid di(4-tert-amylphenyl) ester was performed by performing the same method as in Step (13-2) of Example 13 except that: the thin-film distillation apparatus 201 was heated to 260° C., and the internal pressure was set to approximately 0.5 kPa; and the reaction solution obtained in Step (16-1) was used instead of the reaction solution collected into the reservoir 604 in Step (13-1) and supplied at approximately 1.9 kg/hr to the thin-film distillation apparatus 201 through the line 21 connected with the side of the upper part of the thin-film distillation apparatus 201. By this thermal decomposition, a mixture (17) containing an isocyanate and a hydroxy compound was obtained. Incidentally, liquid-phase components were extracted through the line 23 connected with the bottom of the thin-film distillation apparatus 201, introduced to the upper part of the thin-film distillation apparatus 201 through the line 24 and the line 21, and circulated. The mixture (17) was extracted as gas-phase components through the line 22.

Subsequently, benzyltoluene was used instead of 4-methylbenzyl chloride to perform the distillation separation of the mixture (17) which was gas-phase components. A pressure at the top of the column was approximately 0.1 kPa. Liquid-phase components distilled from the bottom of the continuous multi-stage distillation column 202 were continuously extracted through the line 26 and supplied to the continuous multi-stage distillation column 205. Gas components and liquid components at both the upper and lower second theoretical plates relative to the position of line 22 of the continuous multi-stage distillation column 202 were analyzed at steady state, and operation was performed such that all contained 30 wt % or more of benzyltoluene.

The liquid-phase components extracted through the line 26 were continuously fed to the intermediate stage of the continuous multi-stage distillation column 205 of approximately 5 cm in inside diameter filled with Dixon packing (6 mmφ) to perform the distillation separation of the liquid-phase components. The quantity of heat necessary for the distillation separation was supplied by circulating the solution of the lower part of the column through the lines 31 and 33 and the reboiler 207. A solution temperature at the bottom of the continuous multi-stage distillation column 205 was 160° C., and a pressure at the top of the column was approximately 1.5 kPa. A gas discharged from the top of the continuous multi-stage distillation column 205 was condensed in the condenser 206 through the line 30 and continuously extracted to the reservoir 209 through the line 32.

The solution extracted through the line 32 was a solution containing approximately 99 wt % of diphenylmethane diisocyanate. The yield with respect to 4,4'-methylenedianiline was approximately 81.0%.

Incidentally, in the case where the normal boiling point of diphenylmethane diisocyanate is defined as Tb and the normal boiling point of the hydroxy compound is defined as Ta, a normal boiling point Tc of benzyltoluene satisfied Ta<Tc<Tb.

Example 18

Figure 7:
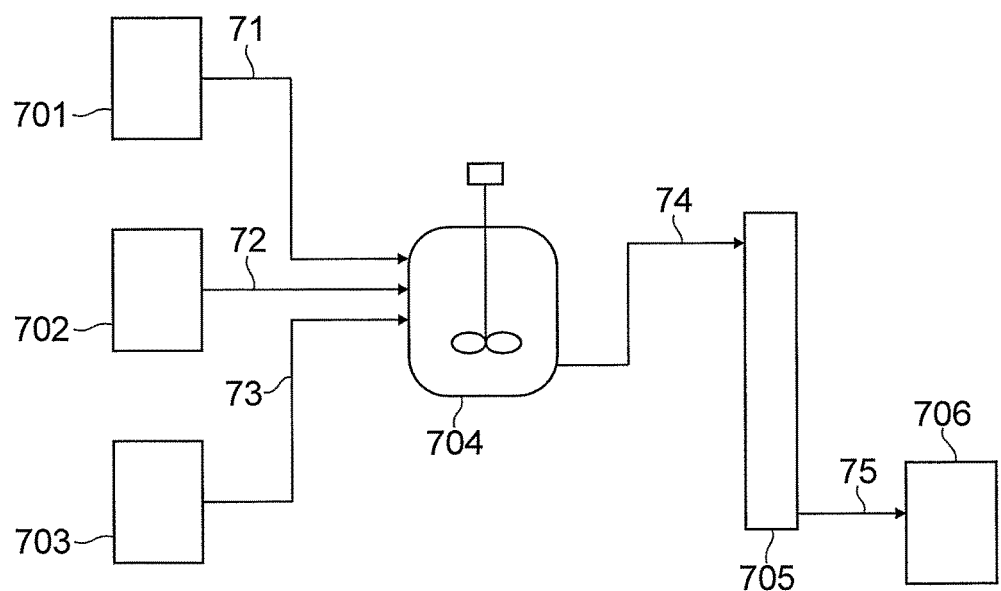
FIG. 7 is an illustrative diagram showing one example of an N-substituted carbamic acid ester producing apparatus.

Step (18-1): Production of N,N-hexanediyl-dicarbamic acid di(3-methylbutyl) ester An apparatus shown, in FIG. 7 was used.

In the state where a line 74 was closed, 9.99 kg (49.5 mol) of bis(3-methylbutyl) carbonate of Reference Example 1 was supplied from a reservoir 701 through a line 71 to a reaction container 704 made of SUS, and 1.15 kg (9.9 mol) of hexamethylenediamine (manufactured by Sigma-Aldrich Corp., USA) was supplied from a reservoir 702 through a line 72 to the reactor 704. A solution temperature within the reactor 704 was adjusted to approximately 80° C., and 19.2 g of sodium methoxide (manufactured by Wako Pure Chemical Industries, Ltd., Japan, a 28% methanol solution) was supplied from a reservoir 703 through a line 73 to the reactor 704 made of SUS and reacted.

As a result of analyzing the solution after reaction by liquid chromatography, N,N'-hexanediyl-dicarbamic acid di(3-methylbutyl) ester formed at a yield of 99.7%.

The line 74 was opened, and the reaction solution was supplied to a column 705 that contained an acidic ion-exchange resin (Amberlyst-15 (spherical): manufactured by ROHM & HAAS Company) adjusted by removing water and was kept warm at 80° C. with an external jacket, to perform the neutralization of sodium methoxide. The solution was transported to a reservoir 706 through a line 75.

Step (18-2): Distilling Off of Low-boiling-point Components

Figure 8:
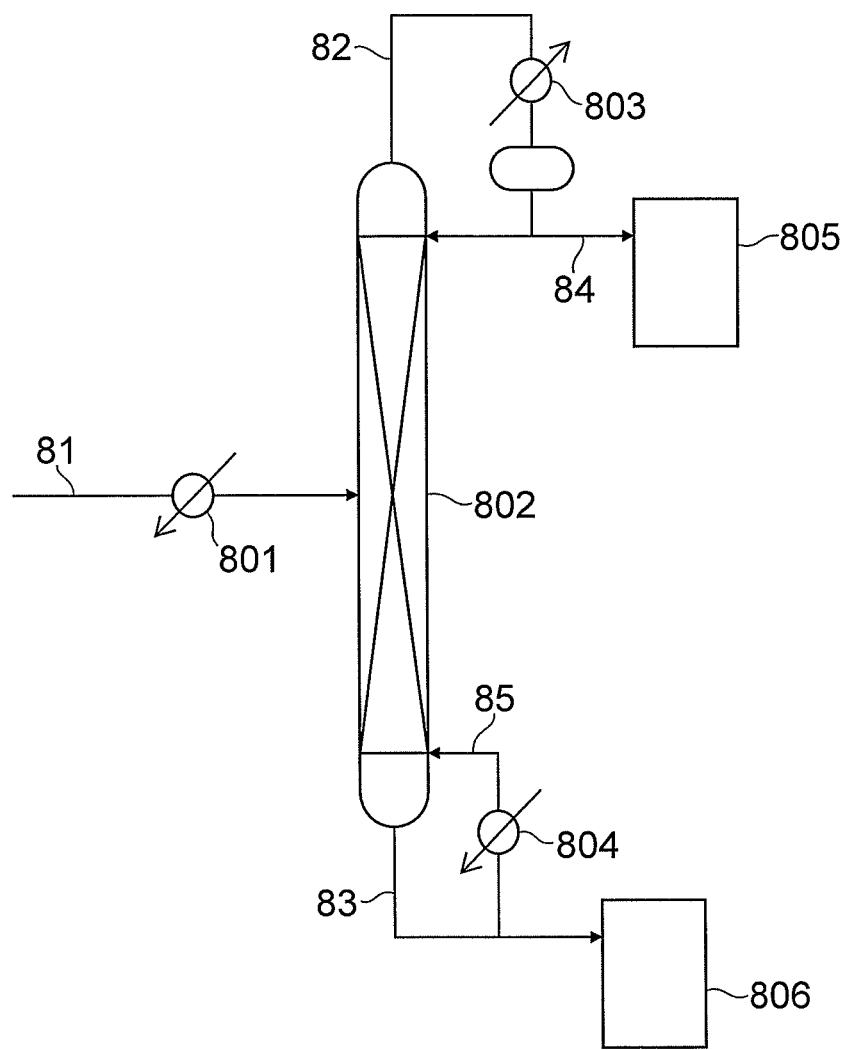
FIG. 8 is an illustrative diagram showing one example of an alcohol distilling off apparatus.

The distilling off of alcohol was performed using an apparatus shown in FIG. 8.

The mixture collected into the reservoir 706 was continuously fed in a liquid state at approximately 0.56 kg/hr from a line 81 through a preheater 801 to the intermediate stage of a continuous multi-stage distillation column 802 of 5 cm in inside diameter filled with Dixon packing (6 mmφ)). The quantity of heat necessary for the distillation was supplied by circulating the solution of the lower part of the column through lines 83 and 85 and a reboiler 804. A solution temperature at the bottom of the continuous multi-stage distillation column 802 was set to 160° C., and a pressure at the top of the column was set to approximately 70 kPa. A gas discharged from the top of the continuous multi-stage distillation column 802 was condensed in a condenser 803 through a line 82 and continuously extracted at approximately 86 g/hr to a reservoir 805 through a line 84. From the bottom of the column, continuous extraction was done at approximately 474 g/hr to a reservoir 806 through the line 83.

Figure 9:
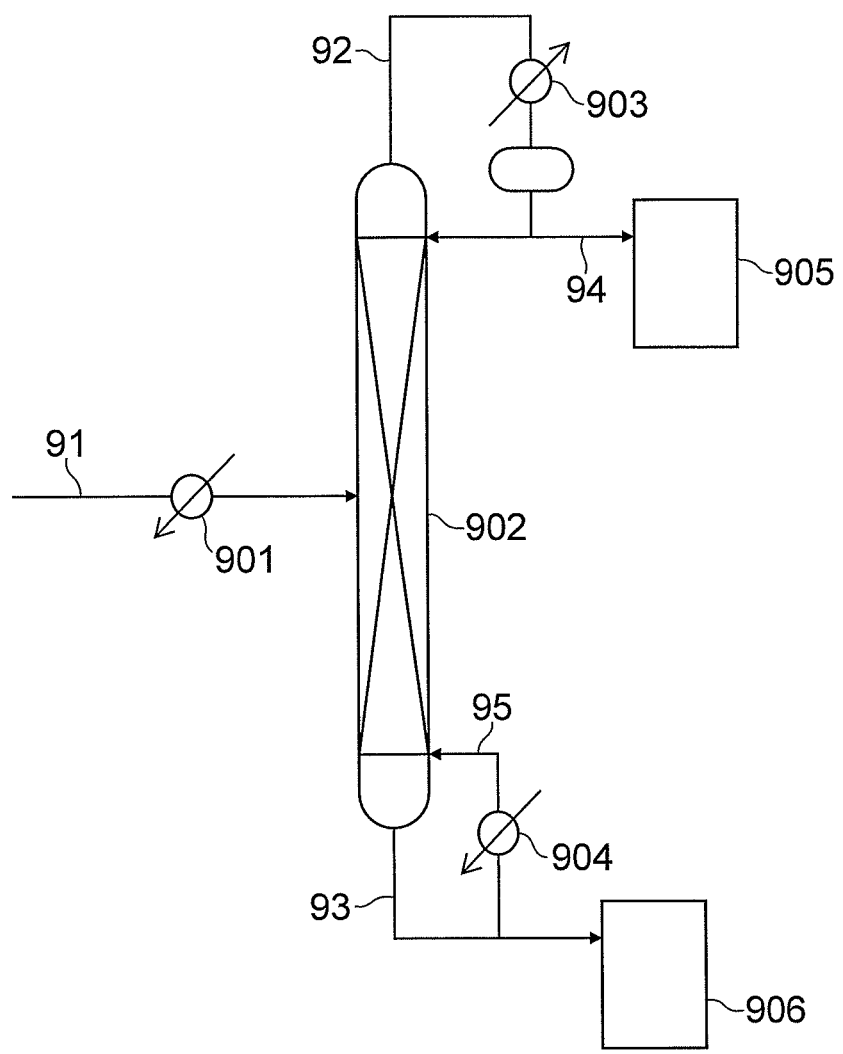
FIG. 9 is an illustrative diagram showing one example of a carbonic acid ester distilling off apparatus.

The distilling off of carbonic acid ester was performed using an apparatus shown in a FIG. 9.

The mixture collected into the reservoir 806 was continuously fed in a liquid state at approximately 474 g/hr from a line 91 through a preheater 901 to the intermediate stage of a continuous multi-stage distillation column 902 of 5 cm in inside diameter filled with Dixon packing (6 mmφ). The quantity of heat necessary for the distillation was supplied by circulating the solution of the lower part of the column through lines 93 and 95 and a reboiler 904. A solution temperature at the bottom of the continuous multi-stage distillation column 902 was set to 160° C., and a pressure at the top of the column was set to approximately 2.6 kPa. A gas discharged from the top of the continuous multi-stage distillation column 902 was condensed in a condenser 903 through a line 92 and continuously extracted at approximately 150 g/hr to a reservoir 905 through a line 94. From the bottom of the column, continuous extraction was done at approximately 87 g/hr to a reservoir 906 through the line 93.

As a result of conducting liquid chromatography analysis on the mixture extracted to the reservoir 906, the mixture contained approximately 98.1 wt % of N,N'-hexanediyl-dicarbamic acid di(3-methylbutyl) ester.

Figure 10:
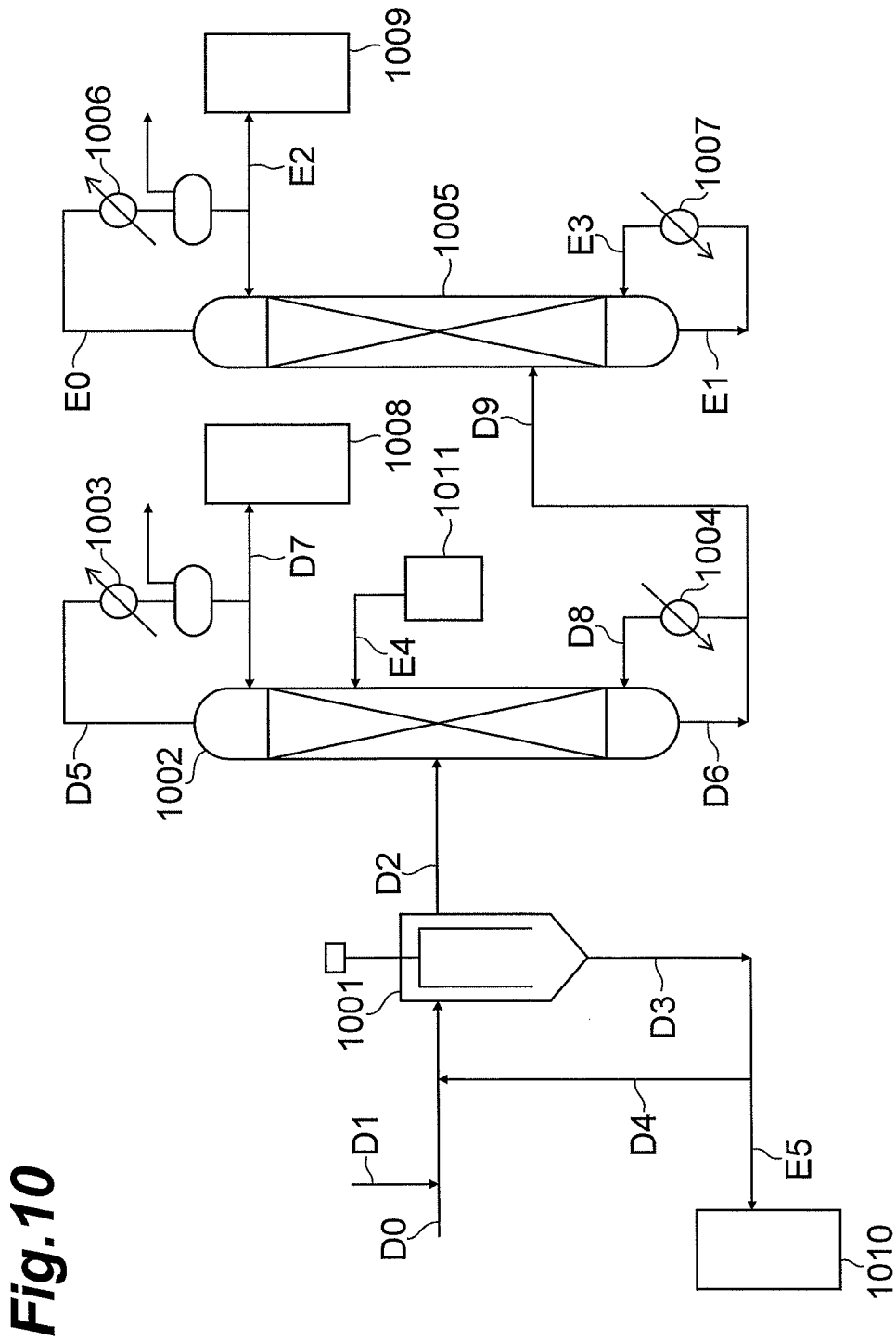
FIG. 10 is an illustrative diagram showing one example of an N-substituted carbamic acid ester thermally decomposing apparatus and an isocyanate separating apparatus.

Step (18-3): Thermal decomposition of N,N'-hexanediyl-dicarbamic acid di(3-methylbutyl) ester and distillation separation of isocyanate An apparatus shown in FIG. 10 was used.

1,2-Dichlorobenzene (manufactured by TOKYO CHEMICAL INDUSTRY CO., LTD., Japan) was supplied to a continuous multi-stage distillation column 1002 of approximately 5 cm in inside diameter filled with Dixon packing (6 mmφ, and the state where 1,2-dichlorobenzene was under total reflux was created with a pressure at the top of the column set to approximately 1 kPa.

A thin-film distillation apparatus 1001 (manufactured by KOBELCO ECO-SOLUTIONS Co., Ltd., Japan) of 0.1 m² in heat transfer area was heated to 270° C., and the internal pressure was set to approximately 13 kPa. The mixture collected into the reservoir 906 in Step (18-2) was heated to 160° C. and supplied at approximately 580 g/hr to the upper part of the thin-film evaporator 1001 through a line D0. Moreover, dibutyltin dilaurate (manufactured by Wako Pure Chemical Industries, Ltd., Japan) was fed at approximately 25.2 g/hr through a line D 1. Liquid-phase components were extracted through a line D3 from the bottom of the thin-film distillation apparatus 1001 and circulated to the upper part of the thin-film distillation apparatus 1001 through a line D4. Gas-phase components were extracted through a line D2.

The gas-phase components extracted through the line D2 from the thin-film distillation apparatus 1001 were continuously fed to the intermediate stage of the continuous multi-stage distillation column 1002, and at the same time, 1,2-dichlorobenzene was supplied at approximately 0.3 kg/hr through a line E4 to perform the distillation separation of the gas-phase components. The quantity of heat necessary for the distillation separation was supplied by circulating the solution of the lower part of the column through lines D6 and D8 and a reboiler 1004. A solution temperature at the bottom of the continuous multi-stage distillation column 1002 was 150° C., and a pressure at the top of the column was approximately 50 kPa. A gas discharged from the top of the continuous multi-stage distillation column 1002 was condensed in a condenser 1003 through a line D5 and continuously extracted through a line D7. Liquid-phase components were extracted through a line D9 from the bottom of the continuous multi-stage distillation column 1002. Gas components and liquid components at both the upper and lower third theoretical plates relative to the position of line D2 of the continuous multi-stage distillation column 1002 were analyzed at steady state, and operation was performed such that all contained 30 wt % or more of 1,2-dichlorobenzene.

The liquid-phase components extracted through the line D9 were continuously fed to the intermediate stage of a continuous multi-stage distillation column 1005 of approximately 5 cm in inside diameter filled with Dixon packing (6 mmφ) to perform the distillation separation of the liquid-phase components. The quantity of heat necessary for the distillation separation was supplied by circulating the solution of the lower part of the column through lines E1 and E3 and a reboiler 1007. A gas discharged from the top of the continuous multi-stage distillation column 1005 was condensed in a condenser 1006 through a line E0 and continuously extracted to a reservoir 1009 through a line E2.

After 40-hour operation, the liquid-phase components were extracted at approximately 11 g/hr to a reservoir 1010 through a line E5.

The solution extracted through the line E2 was a solution containing approximately 99.8 wt % of hexamethylene diisocyanate. The yield with respect to hexamethylenediamine was 82.1%.

Incidentally, in the case where the normal boiling point of hexamethylene diisocyanate is defined as Tb and the normal boiling point of the hydroxy compound is defined as Ta, a normal boiling point Tc of 1,2-dichlorobenzene satisfied Ta<Tc<Tb.

Example 19

Step (19-1): Production of N,N'-hexanediyl-dicarbamic acid dibutyl ester

A reaction solution containing N,N'-hexanediyl-dicarbamic acid dibutyl ester was obtained by performing the same method as in Step (18-1) of Example 18 except that 8.76 kg (50.3 mol) of dibutyl carbonate of Reference Example 2 was used instead of bis(3-methylbutyl) carbonate, 1.30 kg (11.1 mol) of hexamethylenediamine was used, and 20.1 g of sodium methoxide (28% methanol solution) was used. The yield of N,N'-hexanediyl-dicarbamic acid dibutyl ester was 95.3%. Subsequently, the neutralization of sodium methoxide was performed, and the solution was transported the reservoir 706.

Step (19-2): Distilling Off of Low-boiling-point Components

The distilling off of alcohol was performed in the same way as in Step (18-2) of Example 18 except that: the mixture collected into the reservoir 706 was fed at approximately 1 kg/hr from the line 81; and a solution temperature at the bottom of the continuous multi-stage distillation column 802 was set to 140° C., and a pressure at the top of the column was set to 70 kPa.

Subsequently, the same method as in Step (18-2) of Example 18 was performed except that: the mixture collected into the reservoir 806 was supplied at approximately 540 g/hr from the line 91 to the continuous multi-stage distillation column 902; and a solution temperature at the bottom of the continuous multi-stage distillation column 902 was set to 150° C., and a pressure at the top of the column was set to approximately 3.0 kPa. As a result of conducting liquid chromatography analysis on the mixture extracted to the reservoir 906, the mixture contained approximately 97.9 wt % of N,N'-hexanediyl-dicarbamic acid dibutyl ester.

Step (19-3): Thermal decomposition of N,N'-hexanediyl-dicarbamic acid dibutyl ester and distillation separation of isocyanate The same method as in Step (18-3) of Example 18 was performed except that: 1,3,5-triethylbenzene was used instead of 1,2-dichlorobenzene; the thin-film distillation apparatus 1001 was heated to 280° C., and the internal pressure was set to approximately 13 kPa; and the mixture collected into the reservoir 906 in Step (19-2) was used instead of the mixture collected into the reservoir 906 in Step (18-2) and supplied at approximately 630 g/hr to the upper part of the thin-film evaporator 1001.

Subsequently, 1,3,5-triethylbenzene was supplied instead of 1,2-dichlorobenzene at approximately 0.2 kg/hr to the intermediate stage of the continuous multi-stage distillation column 1002 to perform the distillation separation of gas-phase components that formed in the thin-film evaporator 1001. The liquid-phase components extracted through the line D9 were continuously fed to the intermediate stage of the continuous multi-stage distillation column 1005 to perform the distillation separation of the liquid-phase components, and the concentrates were continuously extracted to the reservoir 1009 through the line E2. The solution extracted through the line E2 was a solution containing approximately 99.8 wt % of hexamethylene diisocyanate. The yield with respect to hexamethylenediamine was 80.5%.

Incidentally, in the case where the normal boiling point of hexamethylene diisocyanate is defined as Tb and the normal boiling point of the hydroxy compound is defined as Ta, a normal boiling point Tc of 1,3,5-triethylbenzene satisfied Ta<Tc<

Example 20

Step (20-1): Production of 3-(butoxycarbonylamino-methyl)-3,5,5-trimethylcyclohexylcarbamic acid butyl ester A reaction solution containing 3-(butoxycarbonylamino-methyl)-3,5,5-trimethylcyclohexylcarbamic acid butyl ester was obtained by performing the same method as in Step (18-1) of Example 18 except that 9.75 kg (56.0 mol) of dibutyl carbonate of Reference Example 2 was used instead of bis(3-methylbutyl) carbonate, 1.59 kg (9.33 mol) of 3-aminomethyl-3,5,5-trimethylcyclohexylamine was used instead of hexamethylenediamine, and 18.0 g of sodium methoxide (28% methanol solution) was used. The yield of 3-(butoxycarbonylamino-methyl)-3,5,5-trimethylcyclohexylcarbamic acid butyl ester was 94.8%. Subsequently, the neutralization of sodium methoxide was performed, and the solution was transported to the reservoir 706.

Step (20-2): Distilling Off of Low-boiling-point Components

The distilling off of alcohol was performed in the same way as in Step (18-2) of Example 18 except that: the mixture collected into the reservoir 706 was fed at approximately 0.9 kg/hr from the line 81; and a solution temperature at the bottom of the continuous multi-stage distillation column 802 was set to 140° C., and a pressure at the top of the column was set to 70 kPa.

Subsequently, the same method as in Step (18-2) of Example 18 was performed except that: the mixture collected into the reservoir 806 was supplied at approximately 550 g/hr from the line 91 to the continuous multi-stage distillation column 902; and a solution temperature at the bottom of the continuous multi-stage distillation column 902 was set to 150° C., and a pressure at the top of the column was set to approximately 3.0 kPa. As a result of conducting liquid chromatography analysis on the mixture extracted to the reservoir 906, the mixture contained approximately 98.0 wt % of 3-(butoxycarbonylamino-methyl)-3,5,5-trimethylcyclohexylcarbamic acid butyl ester.

Step (20-3): Thermal decomposition of 3-(butoxy-carbonylamino-methyl)-3,5,5-trimethylcyclohexyl-carbamic acid butyl ester and distillation separation of isocyanate The same method as in Step (18-3) of Example 18 was performed except that: cyclododecane (manufactured by TOKYO CHEMICAL INDUSTRY CO., LTD., Japan) was used instead of 1,2-dichlorobenzene; the thin-film distillation apparatus 1001 was heated to 280° C., and the internal pressure was set to approximately 13 kPa; and the mixture collected into the reservoir 906 in Step (20-2) was used instead of the mixture collected into the reservoir 906 in Step (18-2) and supplied at approximately 630 g/hr to the upper part of the thin-film evaporator 1001.

Subsequently, cyclododecane was supplied instead of 1,2-dichlorobenzene at approximately 0.15 kg/hr to the intermediate stage of the continuous multi-stage distillation column 1002 to perform the distillation separation of gas-phase components that formed in the thin-film evaporator 1001. The liquid-phase components extracted through the line D9 were continuously fed to the intermediate stage of the continuous multi-stage distillation column 1005 to perform the distillation separation of the liquid-phase components, and the concentrates were continuously extracted to the reservoir 1009 through the line E2. The solution extracted through the line E2 was a solution containing approximately 99.8 wt % of isophorone diisocyanate. The yield with respect to 3-aminomethyl-3,5,5-trimethylcyclohexylamine was 80.5%.

Incidentally, in the case where the normal boiling point of isophorone diisocyanate is defined as Tb and the normal boiling point of the hydroxy compound is defined as Ta, a normal boiling point Tc of cyclododecane satisfied Ta<Tc<Tb.

Example 21

Step (21-1): Production of N,N'-(4,4'-methanediyl-dicyclohexyl)-dicarbamic acid dibutyl ester A reaction solution containing N,N'-(4,4'-methanediyl-dicyclohexyl)-dicarbamic acid dibutyl ester was obtained by performing the same method as in Step (18-1) of Example 18 except that 12.8 kg (56.0 mol) of bis(2-ethylbutyl) carbonate of Reference Example 3 was used instead of bis(3-methylbutyl) carbonate, 1.87 kg (8.90 mol) of 4,4'-methylenebis(cyclohexylamine) was used instead of hexamethylenediamine, and 22.0 g of sodium methoxide (28% methanol solution) was used. The yield of N,N'-(4,4'-methanediyl-dicyclohexyl)-dicarbamic acid dibutyl ester was 95.3%. Subsequently, the neutralization of sodium methoxide was performed, and the solution was transported to the reservoir 706.

Step (21-2): Distilling Off of Low-boiling-point Components

The distilling off of alcohol was performed in the same way as in Step (18-2) of Example 18 except that: the mixture collected into the reservoir 706 was fed at approximately 1.3 kg/hr from the line 81; and a solution temperature at the bottom of the continuous multi-stage distillation column 802 was set to 140° C., and a pressure at the top of the column was set to 70 kPa.

Subsequently, the same method as in Step (18-2) of Example 18 was performed except that: the mixture collected into the reservoir 806 was supplied at approximately 550 g/hr from the line 91 to the continuous multi-stage distillation column 902; and a solution temperature at the bottom of the continuous multi-stage distillation column 902 was set to 150° C., and a pressure at the top of the column was set to approximately 3.0 kPa. As a result of conducting liquid chromatography analysis on the mixture extracted to the reservoir 906, the mixture contained approximately 96.9 wt % of N,N'-(4,4'-methanediyl-dicyclohexyl)-dicarbamic acid dibutyl ester.

Step (21-3): Thermal decomposition of N,N'-(4,4'-methanediyl-dicyclohexyl)-dicarbamic acid dibutyl ester and distillation separation of isocyanate The same method as in Step (18-3) of Example 18 was performed except that: dibenzyl ether was used instead of 1,2-dichlorobenzene; the thin-film distillation apparatus 1001 was heated to 280° C., and the internal pressure was set to approximately 13 kPa; and the mixture collected into the reservoir 906 in Step (21-2) was used instead of the mixture collected into the reservoir 906 in Step (18-2) and supplied at approximately 770 g/hr to the upper part of the thin-film evaporator 1001.

Subsequently, dibenzyl ether was supplied instead of 1,2-dichlorobenzene at approximately 0.22 kg/hr to the intermediate stage of the continuous multi-stage distillation column 1002 to perform the distillation separation of gas-phase components that formed in the thin-film evaporator 1001. A solution temperature at the bottom of the continuous multi-stage distillation column 1002 was 150° C., and a pressure at the top of the column was approximately 50 kPa. The liquid-phase components extracted through the line D9 were continuously fed to the intermediate stage of the continuous multi-stage distillation column 1005 to perform the distillation separation of the liquid-phase components, and the concentrates were continuously extracted to the reservoir 1009 through the line E2. The solution extracted through the line E2 was a solution containing approximately 98.5 wt % of dicyclohexylmethane diisocyanate and containing approximately 0.7 wt % of light boiling compounds presumed to be derived from dibenzyl ether. The yield with respect to 4,4'-methylenebis(cyclohexylamine) was 76.5%.

Incidentally, in the case where the normal boiling point of dicyclohexylmethane diisocyanate is defined as Tb and the normal boiling point of the hydroxy compound is defined as Ta, a normal boiling point Tc of dibenzyl ether satisfied Ta<Tc<Tb.

Example 22

Step (22-1): Production of N,N-hexanediyl-dicarbamic acid dibutyl ester

A reaction solution containing N,N'-hexanediyl-dicarbamic acid dibutyl ester was obtained by performing a method equivalent to Step (13-1) of Example 13 except that: 0.74 kg (6.4 mol) of hexamethylenediamine was used instead of 3-aminomethyl-3,5,5-trimethylcyclohexylamine, 28.1 kg (379 mol) of 1-butanol was used instead of phenol, and 0.19 kg (3.2 mol) of urea was used; and the packed column 602 was heated to 220° C. As a result of analyzing it by liquid chromatography and $^1$H-NMR, N,N'-hexanediyl-dicarbamic acid dibutyl ester formed at a yield of approximately 95% with respect to hexamethylenediamine in this reaction solution.

Step (22-2): Distilling Off of Low-boiling-point Components

The distilling off of alcohol was performed using the apparatus shown in FIG. 8.

The reaction solution obtained in Step (22-1) was continuously fed in a liquid state at approximately 1.0 kg/hr from the line 81 through the preheater 801 to the intermediate stage of the continuous multi-stage distillation column 802 of 5 cm in inside diameter filled with Dixon packing (6 mmφ)). The quantity of heat necessary for the distillation was supplied by circulating the solution of the lower part of the column through the lines 83 and 85 and the reboiler 804. A solution temperature at the bottom of the continuous multi-stage distillation column 802 was set to 160° C., and a pressure at the top of the column was set to approximately 70 kPa. A gas discharged from the top of the continuous multi-stage distillation column 802 was condensed in the condenser 803 through the line 82 and continuously extracted at approximately 86 g/hr to the reservoir 805 through the line 84. From the bottom of the column, continuous extraction was done at approximately 474 g/hr to the reservoir 806 through the line 83. Approximately 99.1 wt % of N,N'-hexanediyl-dicarbamic acid dibutyl ester was contained.

Step (22-3): Thermal decomposition of N,N'-hexanediyl-dicarbamic acid dibutyl ester and distillation separation of isocyanate The apparatus shown in FIG. 10 was used.

Butylbenzene (manufactured by TOKYO CHEMICAL INDUSTRY CO., LTD., Japan) was supplied to the continuous multi-stage distillation column 1002, and the state where butylbenzene was under total reflux was created with a pressure at the top of the column set to approximately 0.1 kPa.

The thin-film distillation apparatus 1001 was heated to 270° C., and the internal pressure was set to approximately 1.3 kPa. The solution collected into the reservoir 806 in Step (22-2) was heated to 160° C. and supplied at approximately 580 g/hr to the upper part of the thin-film evaporator 1001 through the line D0. Moreover, dibutyltin dilaurate was fed at approximately 22.1 g/hr through the line D 1. Liquid-phase components were extracted through the line D3 from the bottom of the thin-film distillation apparatus 1001 and circulated to the upper part of the thin-film distillation apparatus 1001 through the line D4. Gas-phase components were extracted through the line D2.

The gas-phase components extracted through the line D2 from the thin-film distillation apparatus 1001 were continuously fed to the intermediate stage of the continuous multi-stage distillation column 1002, and at the same time, butylbenzene was supplied at approximately 0.3 kg/hr to perform the distillation separation of the gas-phase components. The quantity of heat necessary for the distillation separation was supplied by circulating the solution of the lower part of the column through the lines D6 and D8 and the reboiler 1004. A solution temperature at the bottom of the continuous multi-stage distillation column 1002 was 150° C., and a pressure at the top of the column was approximately 50 kPa. A gas discharged from the top of the continuous multi-stage distillation column 1002 was condensed in the condenser 1003 through the line D5 and continuously extracted through the line D7. Liquid-phase components were extracted from the line D9 disposed at the bottom of the continuous multi-stage distillation column 1002. Gas components and liquid components at both the upper and lower third theoretical plates relative to the position of line D2 of the continuous multi-stage distillation column 1002 were analyzed at steady state, and operation was performed such that all contained 30 wt % or more of butylbenzene.

The liquid-phase components extracted through the line D9 were continuously fed to the intermediate stage of the continuous multi-stage distillation column 1005 of approximately 5 cm in inside diameter filled with Dixon packing (6 mmφ) to perform the distillation separation of the liquid-phase components. The quantity of heat necessary for the distillation separation was supplied by circulating the solution of the lower part of the column through the lines E1 and E3 and the reboiler 1007. A gas discharged from the top of the continuous multi-stage distillation column 1005 was condensed in the condenser 1006 through the line BO and continuously extracted to the reservoir 1009 through the line E2. Liquid-phase components were extracted to the reservoir 1010 through the line E4.

The solution extracted through the line E2 was a solution containing approximately 99.8 wt % of hexamethylene diisocyanate. The yield with respect to hexamethylenediamine was 80.5%.

Incidentally, in the case where the normal boiling point of hexamethylene diisocyanate is defined as Tb and the normal boiling point of the hydroxy compound is defined as Ta, a normal boiling point Tc of butylbenzene satisfied Ta<Tc<

Example 23

Step (23-1): Production of 3-((2-ethylbutyloxy)carbonylamino-methyl)-3,5,5-trimethylcyclohexylc arbamic acid (2-ethylbutyl) ester A reaction solution containing 3-((2-ethylbutyloxy)carbonylamino-methyl)-3,5,5-trimethylcyclohexylc arbamic acid (2-ethylbutyl) ester was obtained by performing a method equivalent to Step (13-1) of Example 13 except that: 1.41 kg (8.3 mol) of 3-aminomethyl-3,5,5-trimethylcyclohexylamine was used, 57.8 kg (249 mol) of 2-ethyl-1-butanol was used instead of phenol, and 1.10 kg (18.2 mol) of urea was used; and the packed column 602 was heated to 220° C. As a result of analyzing it by liquid chromatography and $^1$H-NMR, 3-((2-ethylbutyloxy)carbonylamino-methyl)-3,5, 5-trimethylcyclohexylc arbamic acid (2-ethylbutyl) ester formed at a yield of approximately 94% with respect to 3-aminomethyl-3,5,5-trimethylcyclohexylamine in this reaction solution.

Step (23-2): Distilling of Low-boiling-point Components

The same method as in Step (22-2) of Example 22 was performed except that: the reaction solution obtained in Step (23-1) was used instead of the reaction solution obtained in Step (22-1), and the reaction solution was continuously fed at approximately 1.0 kg/hr from the line 81; and a solution temperature at the bottom of the continuous multi-stage distillation column 802 was set to 160° C., and a pressure at the top of the column was set to approximately 70 kPa. From the bottom of the column, a mixture containing approximately 99.1 wt % of 3-((2-ethylbutyloxy)carbonylaminomethyl)-3,5,5-trimethylcyclohexylc arbamic acid (2-ethylbutyl) ester was obtained.

Step (23-3): Thermal decomposition of 3-((2-ethyl-butyloxy)carbonylamino-methyl)-3,5,5-trimethylcyclohexylc arbamic acid (2-ethylbutyl) ester and distillation separation of isocyanate The apparatus shown in FIG. 10 was used.

n-Dodecane was supplied to the continuous multi-stage distillation column 1002, and the state where n-dodecane was under total reflux was created with a pressure at the top of the column set to approximately 0.1 kPa.

The thin-film distillation apparatus 1001 was heated to 270° C., and the internal pressure was set to approximately 1.3 kPa. The solution collected into the reservoir 806 in Step (23-2) was heated to 160° C. and supplied at approximately 580 g/hr to the upper part of the thin-film evaporator 1001 through the line D0. Moreover, dibutyltin dilaurate was fed at approximately 20.1 g/hr through the line D1. Liquid-phase components were extracted through the line D3 from the bottom of the thin-film distillation apparatus 1001 and circulated to the upper part of the thin-film distillation apparatus 1001 through the line D4. Gas-phase components were extracted through the line D2.

The gas-phase components extracted through the line D2 from the thin-film distillation apparatus 1001 were continuously fed to the intermediate stage of the continuous multi-stage distillation column 1002, and at the same time, n-dodecane was supplied at approximately 0.3 kg/hr to perform the distillation separation of the gas-phase components. The quantity of heat necessary for the distillation separation was supplied by circulating the solution of the lower part of the column through the lines D6 and D8 and the reboiler 1004. A gas discharged from the top of the continuous multi-stage distillation column 1002 was condensed in the condenser 1003 through the line D5 and continuously extracted through the line D7. Liquid-phase components were extracted from the line D9 disposed at the bottom of the continuous multi-stage distillation column 1002. Gas components and liquid components at both the upper and lower first theoretical plates relative to the position of line D2 of the continuous multi-stage distillation column 1002 were analyzed at steady state, and operation was performed such that all contained 30 wt % or more of n-dodecane.

The liquid-phase components extracted through the line D9 were continuously fed to the intermediate stage of the continuous multi-stage distillation column 1005 of approximately 5 cm in inside diameter filled with Dixon packing (6 mmφ)) to perform the distillation separation of the liquid-phase components. The quantity of heat necessary for the distillation separation was supplied by circulating the solution of the lower part of the column through the lines E1 and E3 and the reboiler 1007. A gas discharged from the top of the continuous multi-stage distillation column 1005 was condensed in the condenser 1006 through the line E0 and continuously extracted to the reservoir 1009 through the line E2. Liquid-phase components were extracted to the reservoir 1010 through the line E5.

The solution extracted through the line E2 was a solution containing approximately 99.8 wt % of isophorone diisocyanate. The yield with respect to 3-aminomethyl-3,5,5-trimethylcyclohexylamine was 80.6%.

Incidentally, in the case where the normal boiling point of isophorone diisocyanate is defined as Tb and the normal boiling point of the hydroxy compound is defined as Ta, a normal boiling point Tc of n-dodecane satisfied Ta<Tc<Tb.

Example 24

Step (24-1): Production of N,N'-(4,4'-methanediyl-dicyclohexyl)-dicarbamic acid dibutyl ester A reaction solution containing N,N'-(4,4'-methanediyl-dicyclohexyl)-dicarbamic acid dibutyl ester was obtained by performing a method equivalent to Step (13-1) of Example 13 except that: 1.60 kg (7.6 mol) of 4,4'-methylenebis (cyclohexylamine) was used instead of 3-aminomethyl-3,5, 5-trimethylcyclohexylamine, 28.1 kg (380 mol) of 1-butanol was used instead of phenol, and 0.96 kg (16.0 mol) of urea was used; and the packed column 602 was heated to 220° C. As a result of analyzing it by liquid chromatography and $^1$H-NMR, N,N'-(4,4'-methanediyl-dicyclohexyl)-dicarbamic acid dibutyl ester formed at a yield of approximately 93% with respect to 4,4'-methylenebis(cyclohexylamine) in this reaction solution.

Step (24-2): Distilling Off of Low-boiling-point Components

The same method as in Step (22-2) of Example 22 was performed except that: the reaction solution obtained in Step (24-1) was used instead of the reaction solution obtained in Step (22-1), and the reaction solution was continuously fed at approximately 1.2 kg/hr from the line 81; and a solution temperature at the bottom of the continuous multi-stage distillation column 802 was set to 160° C., and a pressure at the top of the column was set to approximately 70 kPa. From the bottom of the column, a mixture containing approximately 99.1 wt % of N,N'-(4,4'-methanediyl-dicyclohexyl)-dicarbamic acid dibutyl ester was obtained.

Step (24-3): Thermal decomposition of N,N'-(4,4'-methanediyl-dicyclohexyl)-dicarbamic acid dibutyl ester and distillation separation of isocyanate The apparatus shown in FIG. 10 was used.

Hexylbenzene was supplied to the continuous multi-stage distillation column 1002, and the state where hexylbenzene was under total reflux was created with a pressure at the top of the column set to approximately 0.1 kPa.

The thin-film distillation apparatus 1001 was heated to 270° C., and the internal pressure was set to approximately 1.3 kPa. The solution collected into the reservoir 806 in Step (24-2) was heated to 160° C. and supplied at approximately 580 g/hr to the upper part of the thin-film evaporator 1001 through the line D0. Moreover, dibutyltin dilaurate was fed at approximately 20.1 g/hr through the line D 1. Liquid-phase components were extracted through the line D3 from the bottom of the thin-film distillation apparatus 1001 and circulated to the upper part of the thin-film distillation apparatus 1001 through the line D4. Gas-phase components were extracted through the line D2.

The gas-phase components extracted through the line D2 from the thin-film distillation apparatus 1001 were continuously fed to the intermediate stage of the continuous multi-stage distillation column 1002, and at the same time, hexylbenzene was supplied at approximately 0.3 kg/hr to perform the distillation separation of the gas-phase components. The quantity of heat necessary for the distillation separation was supplied by circulating the solution of the lower part of the column through the lines D6 and D8 and the reboiler 1004. A gas discharged from the top of the continuous multi-stage distillation column 1002 was condensed in the condenser 1003 through the line D5 and continuously extracted through the line D7. Liquid-phase components were extracted from the line D9 disposed at the bottom of the continuous multi-stage distillation column 1002. Gas components and liquid components at both the upper and lower first theoretical plates relative to the position of line D2 of the continuous multi-stage distillation column 1002 were analyzed at steady state, and operation was performed such that all contained 30 wt % or more of hexylbenzene.

The liquid-phase components extracted through the line D9 were continuously fed to the intermediate stage of the continuous multi-stage distillation column 1005 of approximately 5 cm in inside diameter filled with Dixon packing (6 mmφ)) to perform the distillation separation of the liquid-phase components. The quantity of heat necessary for the distillation separation was supplied by circulating the solution of the lower part of the column through the lines E1 and E3 and the reboiler 1007. A gas discharged from the top of the continuous multi-stage distillation column 1005 was condensed in the condenser 1006 through the line BO and continuously extracted to the reservoir 1009 through the line E2. Liquid-phase components were extracted to the reservoir 1010 through the line E4.

The solution extracted through the line E2 was a solution containing approximately 99.8 wt % of dicyclohexylmethane diisocyanate. The yield with respect to 4,4'-methylenebis(cyclohexylamine) was 75.1%.

Incidentally, in the case where the normal boiling point of dicyclohexylmethane diisocyanate is defined as Tb and the normal boiling point of the hydroxy compound is defined as Ta, a normal boiling point Tc of hexylbenzene satisfied Ta<Tc<Tb.

Example 25

Step (25-1): Production of N,N'-hexanediyl-dicarbamic acid di(4-(1,1,3,3-tetramethylbutyl)phenyl) ester N,N'-hexanediyl-dicarbamic acid di(4-(1,1,3,3-tetramethylbutyl)phenyl) ester was obtained at a yield of approximately 92% with respect to hexamethylenediamine by performing the same method as in Step (9-1) of Example 9 except that 2.4 kg (20.7 mol) of hexamethylenediamine, 127.9 kg (620 mol) of 4-(1,1,3,3-tetramethylbutyl)phenol, and 4.97 kg of urea were used.

Figure 11:
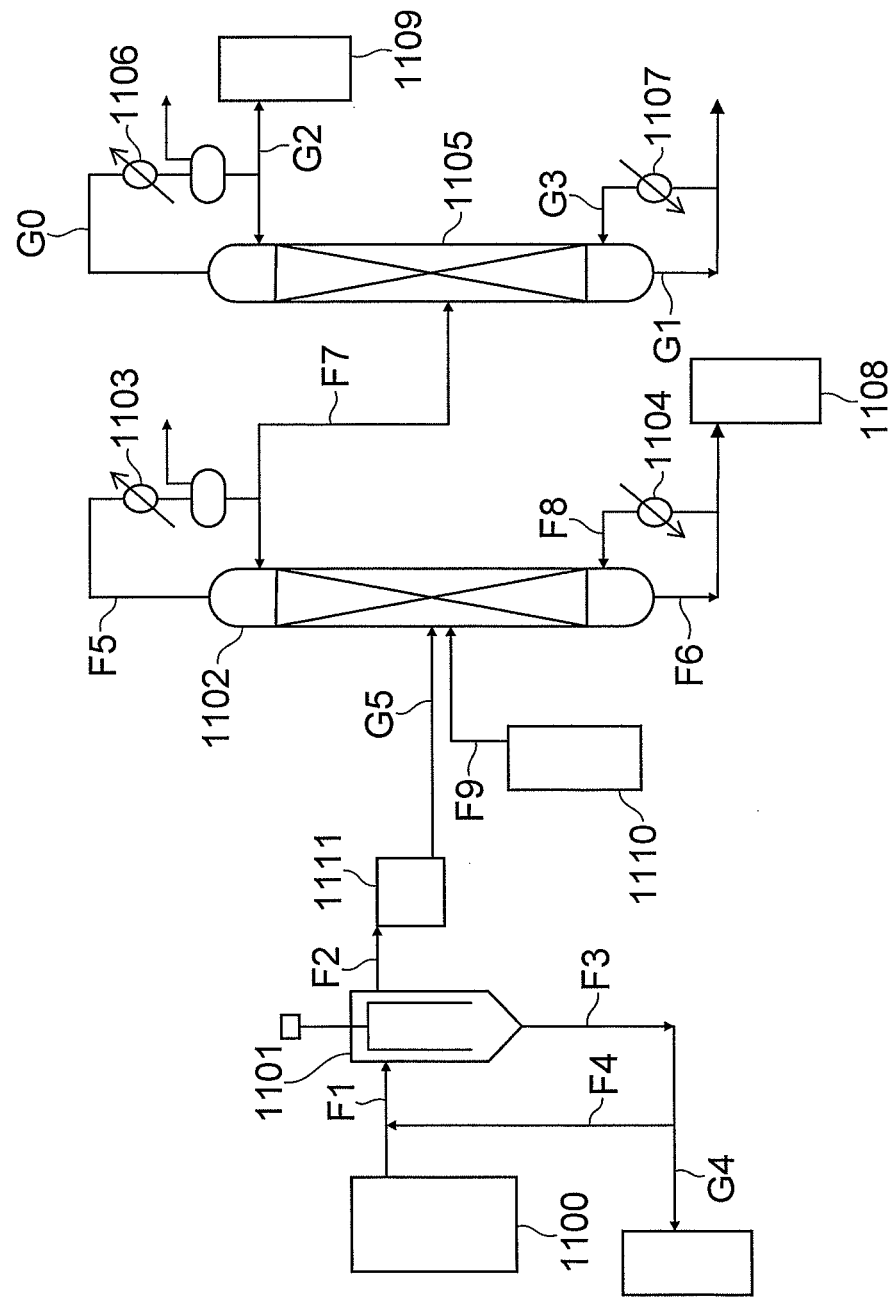
FIG. 11 is an illustrative diagram showing one example of an N-substituted carbamic acid ester thermally decomposing apparatus and an isocyanate separating apparatus.

Step (25-2): Thermal decomposition of N,N'-hexanediyl-dicarbamic acid di(4-(1,1,3,3-tetramethylbutyl)phenyl) ester and separation and collection of isocyanate An apparatus shown in FIG. 11 was used.
A thin-film distillation apparatus 1101 was heated to 280° C., and the internal pressure was set to approximately 1.0 kPa. The reaction solution collected into the reservoir 305 in Step (25-1) was heated to 150° C. and supplied at approximately 1.0 kg/hr to the thin-film distillation apparatus 1101 through a line F 1 connected with the side of the upper part of the thin-film distillation apparatus 1101 to perform the thermal decomposition of N,N'-hexanediyl-dicarbamic acid di(4-(1,1,3,3-tetramethylbutyl)phenyl) ester. By this thermal decomposition, a mixture (25) containing an isocyanate and a hydroxy compound was obtained. Incidentally, liquid-phase components were extracted through a line F3 connected with the bottom of the thin-film distillation apparatus 1101, introduced to the upper part of the thin-film distillation apparatus 1101 through a line F4 and the line F1, and circulated. The mixture (25) was extracted as gas-phase components through a line F2 and then condensed into a liquid in a condenser 1111 operated at approximately 80° C.

The mixture (25) made into a liquid in the condenser 1111 was continuously fed to the intermediate stage of a continuous multi-stage distillation column 1102 through a line G5, and at the same time, n-pentadecane was supplied through a line F9 from a reservoir 1110 to perform the distillation separation of the mixture (25). The quantity of heat necessary for the distillation separation was supplied by circulating the solution of the lower part of the column through lines F6 and F8 and a reboiler 1104. A pressure at the top of the column was approximately 5 kPa. A gas discharged from the top of the continuous multi-stage distillation column 1102 was condensed into liquid-phase components in a condenser 1103 through a line F5, continuously extracted through a line F7, and supplied to a continuous multi-stage distillation column 1105. Gas components and liquid components at both the upper and lower third theoretical plates relative to the position of the line G5 of the continuous multi-stage distillation column 1102 were analyzed at steady state, and operation was performed such that all contained 30 wt % of or more n-pentadecane.

The liquid-phase components extracted through the line F7 were continuously fed to the intermediate stage of the continuous multi-stage distillation column 1105 to perform the distillation separation of the liquid-phase components. The quantity of heat necessary for the distillation separation was supplied by circulating the solution of the lower part of the column through lines G1 and G3 and a reboiler 1107. A solution temperature at the bottom of the continuous multi-stage distillation column 1105 was 150° C., and a pressure at the top of the column was approximately 1.5 kPa. A gas discharged from the top of the continuous multi-stage distillation column 1105 was condensed in a condenser 1106 through a line G0 and continuously extracted to a reservoir 1109 through a line G2.

The solution extracted through the line G2 was a solution containing approximately 99 wt % of hexamethylene diisocyanate. The yield with respect to hexamethylenediamine was 62.8%.

Incidentally, in the case where the normal boiling point of hexamethylene diisocyanate is defined as Tb and the normal boiling point of the hydroxy compound is defined as Ta, a normal boiling point Tc of n-pentadecane satisfied Tb<Tc<Ta.

Example 26

Step (26-1): Production of N,N-hexanediyl-dicarbamic acid dimethyl ester

Reactions were performed using the apparatus shown in FIG. 1.

A reaction solution containing N,N'-hexanediyl-dicarbamic acid dimethyl ester (hereinafter, also referred to as a "reaction solution (26)") was obtained by performing the same method as in Step (1-1) of Example 1 except that 15.8 kg (99.2 mol) of methylphenyl carbonate instead of diphenyl carbonate, 11.7 kg (124 mol) of phenol, and 2.88 kg (24.8 mol) of hexamethylenediamine were used. As a result of analyzing the reaction solution (26) by liquid chromatography, N,N'-hexanediyl-dicarbamic acid dimethyl ester formed at a yield of 94.5%.

Step (26-2): Thermal decomposition of N,N'-hexanediyl-dicarbamic acid dimethyl ester and separation and collection of isocyanate Reactions were performed using the apparatus shown in FIG. 2.

p-Xylene (manufactured by TOKYO CHEMICAL INDUSTRY CO., LTD., Japan) was used instead of n-dodecane, and the total reflux operation of p-xylene was performed with a pressure at the top of the column set to 10 kPa.

The thin-film distillation apparatus 201 of 0.1 m² in heat transfer area was heated to 290° C., and the internal pressure was set to approximately 15 kPa. The reaction solution collected into the reservoir 105 in Step (26-1) was heated to 150° C. and supplied at approximately 1.0 kg/hr to the upper part of the thin-film distillation apparatus 201 through the line 21, and the thermal decomposition of N,N'-hexanediyl-dicarbamic acid dimethyl ester was performed to thereby obtain a mixture containing an isocyanate and a hydroxy compound. Liquid-phase components were extracted through the line 23 from the bottom of the thin-film distillation apparatus 201 and circulated to the upper part of the thin-film distillation apparatus 201 through the line 24 and the line 21. The mixture was extracted as gas-phase components through the line 22.

The mixture, which was gas-phase components, extracted through the line 22 from the thin-film distillation apparatus 201 was continuously fed to the intermediate stage of the continuous multi-stage distillation column 202, and at the same time, p-xylene was supplied at approximately 1.0 kg/hr through the line 29 from the reservoir 210 to perform the distillation separation of the mixture which was gas-phase components. The quantity of heat necessary for the distillation separation was supplied by circulating the solution of the lower part of the column through the lines 26 and 28 and the reboiler 204. A gas discharged from the top of the continuous multi-stage distillation column 202 was condensed in the condenser 203 through the line 25 and continuously extracted through the line 27. On the other hand, liquid-phase components were extracted through the line 26 from the bottom of the column and supplied to the distillation column 205. Gas components and liquid components at both the upper and lower first theoretical plates relative to the position of line 22 of the continuous multi-stage distillation column 202 were analyzed at steady state, and operation was performed such that all contained 30 wt % or more of p-xylene.

The liquid-phase components extracted through the line 26 were continuously fed to the intermediate stage of the continuous multi-stage distillation column 205 of approximately 5 cm in inside diameter filled with Dixon packing (6 mmφ) to perform the distillation separation of the liquid-phase components. The quantity of heat necessary for the distillation separation was supplied by circulating the solution of the lower part of the column through the lines 31 and 33 and the reboiler 207. A solution temperature at the bottom of the continuous multi-stage distillation column 205 was 150° C., and a pressure at the top of the column was approximately 1.5 kPa. A gas discharged from the top of the continuous multi-stage distillation column 205 was condensed in the condenser 206 through the line 30 and continuously extracted to the reservoir 209 through the line 32. The solution extracted through the line 32 was a solution containing approximately 99.8 wt % of hexamethylene diisocyanate. The yield with respect to hexamethylenediamine was 80.0%.

Incidentally, in the case where the normal boiling point of hexamethylene diisocyanate is defined as Tb and the normal boiling point of the hydroxy compound is defined as Ta, a normal boiling point Tc of p-xylene satisfied Ta<Tc<Tb.

Example 27

Step (27-1): Production of N,N'-hexanediyl-dicarbamic acid dichloride

Figure 12:
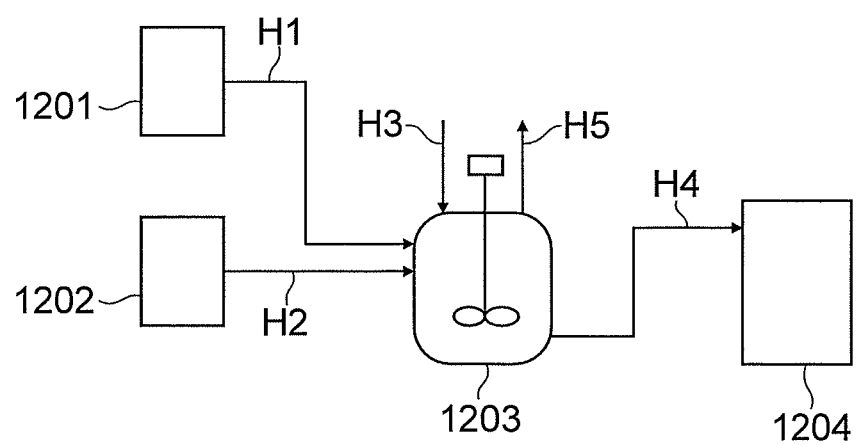
FIG. 12 is an illustrative diagram showing one example of an N-substituted carbamic acid chloride producing apparatus.

An apparatus shown in FIG. 12 was used. 25 kg of chlorobenzene (manufactured by TOKYO CHEMICAL INDUSTRY CO., LTD., Japan) was fed to a stirred tank 1203 through a line H1, and 1.2 kg (10.3 mol) of hexamethylenediamine was fed to the stirred tank 1203 through a line H2 and mixed into a uniform solution, which was then cooled to −10° C. Phosgene in a gas state was blown into the mixed solution from a line H3 to perform reaction. Redundant phosgene and hydrogen chloride that formed as by-products were removed from the system through a line H5. Furthermore, a pressure within the system was reduced to 1 kPa, and redundant phosgene and hydrogen chloride were removed from the system. The obtained reaction solution was a solution containing N,N'-hexanediyl-dicarbamic acid dichloride.

Step (27-2): Thermal decomposition of N,N'-hexanediyl-dicarbamic acid dichloride and separation and collection of isocyanate The thermal decomposition of N,N'-hexanediyl-dicarbamic acid dichloride was performed using the apparatus shown in FIG. 2.

Chlorobenzene was supplied to the bottom of the continuous multi-stage distillation column 202, and the total reflux operation of chlorobenzene was performed with a pressure at the top of the column set to approximately 1 kPa.

The thin-film distillation apparatus 201 was heated to 140° C., and the internal pressure was set to approximately 2 kPa. The reaction solution obtained in Step (27-1) was supplied at approximately 1.0 kg/hr to the upper part of the thin-film distillation apparatus 201 through the line 21, with it cooled, and the thermal decomposition of N,N'-hexanediyl-dicarbamic acid dichloride was performed to thereby obtain a mixed gas containing an isocyanate and a hydrogen chloride. Liquid-phase components were extracted through the line 23 from the bottom of the thin-film distillation apparatus 201. The mixed gas was extracted through the line 22.

The mixed gas extracted through the line 22 from the thin-film distillation apparatus 201 was continuously fed to the intermediate stage of the continuous multi-stage distillation column 202, and at the same time, chlorobenzene was supplied at 0.2 kg/hr through the line 29 from the reservoir 210 to perform the distillation separation of the mixed gas. The quantity of heat necessary for the distillation separation was supplied by circulating the solution of the lower part of the column through the lines 26 and 28 and the reboiler 204. A solution temperature at the bottom of the continuous multi-stage distillation column 202 was 200° C., and a pressure at the top of the column was approximately 5 kPa. A gas discharged from the top of the continuous multi-stage distillation column 202 was condensed in the condenser 203 through the line 25 and continuously extracted through the line 27. On the other hand, liquid-phase components were extracted through the line 26 from the bottom of the column and supplied to the distillation column 205. Gas components and liquid components at both the upper and lower third theoretical plates relative to the position of line 22 of the continuous multi-stage distillation column 202 were analyzed at steady state, and operation was performed such that all contained 30 wt % or more of chlorobenzene.

The liquid-phase components extracted through the line 26 were continuously fed to the intermediate stage of the continuous multi-stage distillation column 205 to perform the distillation separation of the liquid-phase components. The quantity of heat necessary for the distillation separation was supplied by circulating the solution of the lower part of the column through the lines 31 and 33 and the reboiler 207. A solution temperature at the bottom of the continuous multi-stage distillation column 205 was approximately 60° C., and a pressure at the top of the column was approximately 1 kPa. A gas discharged from the top of the continuous multi-stage distillation column 205 was condensed in the condenser 206 through the line 30 and continuously extracted to the reservoir 209 through the line 32. The solution extracted through the line 32 was a solution containing approximately 97.1 wt % of hexamethylene diisocyanate. The yield with respect to hexamethylenediamine was 90.1%.

Incidentally, in the case where the normal boiling point of hexamethylene diisocyanate is defined as Tb and the normal boiling point of hydrogen chloride is defined as Ta, a normal boiling point Tc of chlorobenzene satisfied Ta<Tc<Tb.

Example 28

Step (28-1): Thermal decomposition of N,N'-hexanediyl-bis-thiocarbamic acid di(O-phenyl) and separation and collection of isothiocyanate The thermal decomposition of N,N'-hexanediyl-bis-thiocarbamic acid di(O-phenyl) was performed using the apparatus shown in FIG. 2.

n-Dodecane was supplied to the bottom of the continuous multi-stage distillation column 202, and the total reflux operation of n-dodecane was performed with a pressure at the top of the column set to approximately 1 kPa.

The thin-film distillation apparatus 201 was heated to 290° C., and the internal pressure was set to approximately 2 kPa. A reaction solution obtained in a manner similar to Step (26-1) was supplied at approximately 1.0 kg/hr to the upper part of the thin-film distillation apparatus 201 through the line 21, with it cooled, and the thermal decomposition of N,N'-hexanediyl-bis-thiocarbamic acid di(O-phenyl) was performed to thereby obtain a mixed gas containing an isothiocyanate and phenol. Liquid-phase components were extracted through the line 23 from the bottom of the thin-film distillation apparatus 201. The mixed gas was extracted through the line 22.

The mixed gas extracted through the line 22 from the thin-film distillation apparatus 201 was continuously fed to the intermediate stage of the continuous multi-stage distillation column 202, and at the same time, n-dodecane was supplied at 0.3 kg/hr through the line 29 from the reservoir 210 to perform the distillation separation of the mixed gas. The quantity of heat necessary for the distillation separation was supplied by circulating the solution of the lower part of the column through the lines 26 and 28 and the reboiler 204. A gas discharged from the top of the continuous multi-stage distillation column 202 was condensed in the condenser 203 through the line 25 and continuously extracted through the line 27. On the other hand, liquid-phase components were extracted through the line 26 from the bottom of the column and supplied to the distillation column 205. Gas components and liquid components at both the upper and lower third theoretical plates relative to the position of line 22 of the continuous multi-stage distillation column 202 were analyzed at steady state, and operation was performed such that all contained 30 wt % or more of n-dodecane.

The liquid-phase components extracted through the line 26 were continuously fed to the intermediate stage of the continuous multi-stage distillation column 205 to perform the distillation separation of the liquid-phase components. The quantity of heat necessary for the distillation separation was supplied by circulating the solution of the lower part of the column through the lines 31 and 33 and the reboiler 207. A gas discharged from the top of the continuous multi-stage distillation column 205 was condensed in the condenser 206 through the line 30 and continuously extracted to the reservoir 209 through the line 32. The solution extracted through the line 32 was a solution containing approximately 93.1 wt % of hexamethylene diisothiocyanate.

Incidentally, in the case where the normal boiling point of hexamethylene diisothiocyanate is defined as Tb and the normal boiling point of phenol is defined as Ta, a normal boiling point Tc of n-dodecane satisfied Ta<Tc<Tb.

Example 29

Step (29-1): Thermal decomposition of N,N'-hexanediyl-bis-thiocarbamic acid di(S-phenyl) and separation and collection of isocyanate The thermal decomposition of N,N'-hexanediyl-bis-thiocarbamic acid di(S-phenyl) was performed using the apparatus shown in FIG. 2.

n-Dodecane was supplied to the bottom of the continuous multi-stage distillation column 202, and the total reflux operation of n-dodecane was performed with a pressure at the top of the column set to approximately 1 kPa.

The thin-film distillation apparatus 201 was heated to 290° C., and the internal pressure was set to approximately 2 kPa. A reaction solution obtained in a manner similar to Step (26-1) was supplied at approximately 1.0 kg/hr to the upper part of the thin-film distillation apparatus 201 through the line 21, with it cooled, and the thermal decomposition of N,N'-hexanediyl-bis-thiocarbamic acid di(S-phenyl) was performed to thereby obtain a mixed gas containing an isocyanate and benzenethiol. Liquid-phase components were extracted through the line 23 from the bottom of the thin-film distillation apparatus 201. The mixed gas was extracted through the line 22.

The mixed gas extracted through the line 22 from the thin-film distillation apparatus 201 was continuously fed to the intermediate stage of the continuous multi-stage distillation column 202, and at the same time, n-dodecane was supplied at 0.3 kg/hr through the line 29 from the reservoir 210 to perform the distillation separation of the mixed gas. The quantity of heat necessary for the distillation separation was supplied by circulating the solution of the lower part of the column through the lines 26 and 28 and the reboiler 204. A gas discharged from the top of the continuous multi-stage distillation column 202 was condensed in the condenser 203 through the line 25 and continuously extracted through the line 27. On the other hand, liquid-phase components were extracted through the line 26 from the bottom of the column and supplied to the distillation column 205. Gas components and liquid components at both the upper and lower third theoretical plates relative to the position of line 22 of the continuous multi-stage distillation column 202 were analyzed at steady state, and operation was performed such that all contained 30 wt % or more of n-dodecane.

The liquid-phase components extracted through the line 26 were continuously fed to the intermediate stage of the continuous multi-stage distillation column 205 to perform the distillation separation of the liquid-phase components. The quantity of heat necessary for the distillation separation was supplied by circulating the solution of the lower part of the column through the lines 31 and 33 and the reboiler 207. A gas discharged from the top of the continuous multi-stage distillation column 205 was condensed in the condenser 206 through the line 30 and continuously extracted to the reservoir 209 through the line 32. The solution extracted through the line 32 was a solution containing approximately 95.0 wt % of hexamethylene diisocyanate.

Incidentally, in the case where the normal boiling point of hexamethylene diisocyanate is defined as Tb and the normal boiling point of benzenethiol is defined as Ta, a normal boiling point Tc of n-dodecane satisfied Ta<Tc<Tb.

Example 30

Step (30-1): Thermal decomposition of N,N'-hexanediyl-bis-dithiocarbamic acid diphenyl and separation and collection of isothiocyanate The thermal decomposition of N,N'-hexanediyl-bis-dithiocarbamic acid diphenyl was performed using the apparatus shown in FIG. 2.

n-Dodecane was supplied to the bottom of the continuous multi-stage distillation column 202, and the total reflux operation of n-dodecane was performed with a pressure at the top of the column set to approximately 1 kPa.

The thin-film distillation apparatus 201 was heated to 290° C., and the internal pressure was set to approximately 2 kPa. A reaction solution obtained in a manner similar to Step (26-1) was supplied at approximately 1.0 kg/hr to the upper part of the thin-film distillation apparatus 201 through the line 21, with it cooled, and the thermal decomposition of N,N'-hexanediyl-bis-thiocarbamic acid diphenyl was performed to thereby obtain a mixed gas containing an isothiocyanate and benzenethiol. Liquid-phase components were extracted through the line 23 from the bottom of the thin-film distillation apparatus 201. The mixed gas was extracted through the line 22.

The mixed gas extracted through the line 22 from the thin-film distillation apparatus 201 was continuously fed to the intermediate stage of the continuous multi-stage distillation column 202, and at the same time, n-dodecane was supplied at 0.3 kg/hr through the line 29 from the reservoir 210 to perform the distillation separation of the mixed gas. The quantity of heat necessary for the distillation separation was supplied by circulating the solution of the lower part of the column through the lines 26 and 28 and the reboiler 204. A gas discharged from the top of the continuous multi-stage distillation column 202 was condensed in the condenser 203 through the line 25 and continuously extracted through the line 27. On the other hand, liquid-phase components were extracted through the line 26 from the bottom of the column and supplied to the distillation column 205. Gas components and liquid components at both the upper and lower third theoretical plates relative to the position of line 22 of the continuous multi-stage distillation column 202 were analyzed at steady state, and operation was performed such that all contained 30 wt % or more of n-dodecane.

The liquid-phase components extracted through the line 26 were continuously fed to the intermediate stage of the continuous multi-stage distillation column 205 to perform the distillation separation of the liquid-phase components. The quantity of heat necessary for the distillation separation was supplied by circulating the solution of the lower part of the column through the lines 31 and 33 and the reboiler 207. A gas discharged from the top of the continuous multi-stage distillation column 205 was condensed in the condenser 206 through the line 30 and continuously extracted to the reservoir 209 through the line 32. The solution extracted through the line 32 was a solution containing approximately 90.3 wt % of hexamethylene diisothiocyanate.

Incidentally, in the case where the normal boiling point of hexamethylene diisothiocyanate is defined as Tb and the normal boiling point of benzenethiol is defined as Ta, a normal boiling point Tc of n-dodecane satisfied Ta<Tc<Tb.

Reference Example 1

Production of bis(3-methylbutyl) carbonate

Step (I-1): Production of Dialkyltin Catalyst 625 g (2.7 mol) of di-n-butyltin oxide (manufactured by Sankyo Organic Chemicals Co., Ltd., Japan) and 2020 g (22.7 mol) of 3-methyl-1-butanol (manufactured by Wako Pure Chemical Industries, Ltd., Japan) were placed in a 5000-mL (capacity) eggplant-shaped flask. The flask was attached to an evaporator (manufactured by SIBATA SCIENTIFIC TECHNOLOGY LTD., Japan, R-144) connected with an oil bath (manufactured by MASUDA CORP., Japan, OBH-24) with a thermostat, a vacuum pump (manufactured by ULVAC KIKO, INC., Japan, G-50A), and a vacuum controller (manufactured by OKANO WORKS, LTD., Japan, VC-10S). The purge valve outlet of the evaporator was connected with a line for nitrogen gas that flowed at normal pressure. After a pressure within the system was reduced by closing the purge valve of the evaporator, the purge valve was gradually opened to allow nitrogen to flow into the system, which was returned to normal pressure. The oil bath temperature was set to approximately 145° C., the flask was dipped in the oil bath, and the rotation of the evaporator was initiated. The distillation of 3-methyl-1-butanol containing water started when heating was done for approximately 40 minutes under nitrogen at atmospheric pressure with the purge valve of the evaporator opened. After this state was maintained for 7 hours, the purge valve was closed to gradually reduce a pressure within the system, and excessive 3-methyl-1-butanol was distilled in the state where the pressure within the system was 74 to 35 kPa. After no more fraction came out, the flask was taken out of the oil bath. After the flask was cooled to around room temperature (25° C.), the purge valve was gradually opened to return the pressure within the system to atmospheric pressure. 886 g of the reaction solution was obtained in the flask. From analysis results of $^{119}Sn,^{1}H,^{13}C$-NMR, 1,1,3,3-tetra-n-butyl-1,3-bis(3-methylbutyloxy)-distannoxane was confirmed to be obtained at a yield of 99% with respect to di-n-butyltin oxide. Similar procedures were repeated 12 times to obtain 10635 g in total of 1,1,3,3-tetra-n-butyl-1,3-bis(3-methylbutyloxy)-distannoxane.

Step (1-2): Production of bis(3-methylbutyl) carbonate

Figure 13:
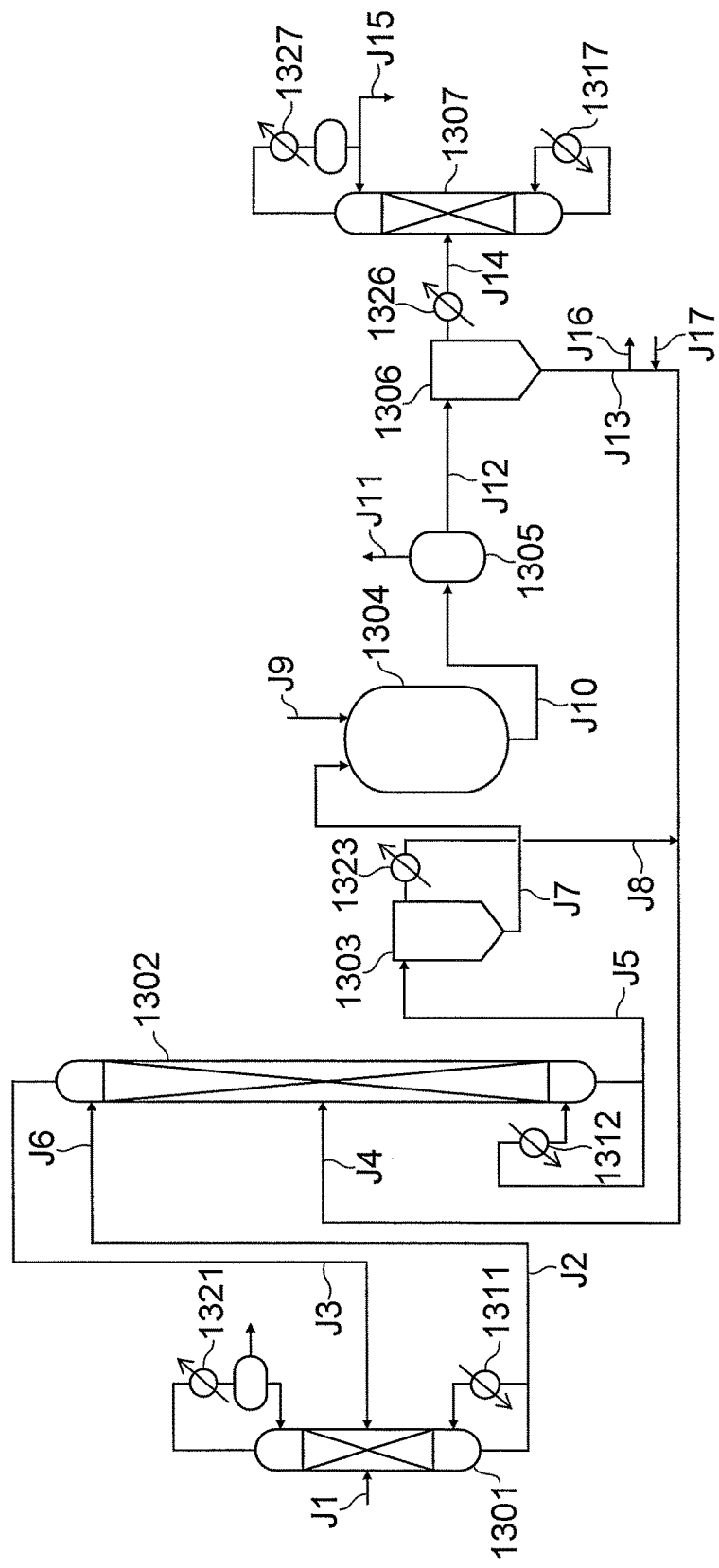
FIG. 13 is an illustrative diagram showing one example of a carbonic acid ester producing apparatus.

Bis(3-methylbutyl) carbonate was produced in a continuous production apparatus as shown in FIG. 13. To a tower reactor 1302 of 151 mm in inside diameter and 5040 mm in effective length filled with a packing material Metal Gauze CY (manufactured by Sulzer Chemtech Ltd., Switzerland), the 1,1,3,3-tetra-n-butyl-1,3-bis(3-methylbutyloxy)distannoxane produced above was supplied at 4388 g/hr from a line J4, and 3-methyl-1-butanol purified in a continuous multi-stage distillation column 1301 was supplied at 14953 g/hr from a line J2. The reactor 1302 was adjusted with a heater and a reboiler 1312 such that the solution temperature became 160° C., and adjusted with a pressure regulating valve such that the pressure became approximately 120 kPa-G A residence time within the reactor was approximately 17 minutes. 15037 g/hr of 3-methyl-1-butanol containing water through a line J3 from the upper part of the reactor and 825 g/hr of 3-methyl-1-butanol through a line J1 were transported to the continuous multi-stage distillation column 1301 that was filled with a packing material Metal Gauze CY and equipped with a reboiler 1311 and a condenser 1321, and distillation purification was performed. Above the distillation column 1301, a fraction containing a high concentration of water was condensed in the condenser 1321 and collected. The purified 3-methyl-1-butanol was transported to the tower reactor 1302 through the line J2 located below the continuous multi-stage distillation column 1301. An alkyltin alkoxide catalyst composition containing di-n-butyl-bis(3-methylbutyloxy)tin and 1,1,3,3-tetra-n-butyl-1,3-bis(3-methylbutyloxy)distannoxane was obtained from the lower part of the tower reactor 1302 and supplied to a thin-film distillation apparatus 1303 (manufactured by KOBELCO ECO-SOLUTIONS Co., Ltd., Japan) through a line J5. 3-Methyl-1-butanol was distilled off in the thin-film distillation apparatus 1303 and returned to the tower reactor 1302 through a condenser 1323, a line J8, and the line J4. The alkyltin alkoxide catalyst composition was transported through a line J7 from the lower part of the thin-film distillation apparatus 1303 and supplied to an autoclave 1304 with the flow rate of di-n-butyl-bis(3-methylbutyloxy) tin and 1,1,3,3-tetra-n-butyl-1,3-bis(3-methylbutyloxy)-distannoxane adjusted to approximately 5130 g/hr. Carbon dioxide was supplied at 973 g/hr from a line J9 to the autoclave 1304, and the internal pressure of the autoclave 1304 was kept at 4 MPa-G A temperature in the autoclave 1304 was set to 120° C., a residence time was adjusted to approximately 4 hours, and the reaction between carbon dioxide and the alkyltin alkoxide catalyst composition was performed to obtain a reaction solution containing bis(3-methylbutyl) carbonate. The reaction solution was transported via a line J10 and a regulating valve to a decarbonator 1305 by which residual carbon dioxide was removed and carbon dioxide was collected from a line J11. Then, the reaction solution was transported through a line 12 to a thin-film distillation apparatus 1306 (manufactured by KOBELCO ECO-SOLUTIONS Co., Ltd., Japan) adjusted to approximately 142° C. and approximately 0.5 kPa, and supplied with the flow rate of 1,1,3,3-tetra-n-butyl-1,3-bis (3-methylbutyloxy)-di stannoxane adjusted to approximately 4388 g/hr, to obtain a fraction containing bis(3-methylbutyl) carbonate, whereas evaporation residues were circulated to the tower reactor 1302 through a line J13 and the line J4, with the flow rate of 1,1,3,3-tetrabutyl-1,3-bis (3-methylbutyloxy)-distannoxane adjusted to approximately 4388 g/hr. The fraction containing bis(3-methylbutyl) carbonate was supplied at 959 g/hr through a condenser 1326 and a transport line J14 to a continuous multi-stage distillation column 1307 that was filled with a packing material Metal Gauze CY and equipped with a reboiler 1317 and a condenser 1327, and after distillation purification was performed, 99 wt % of bis(3-methylbutyl) carbonate was obtained at 944 g/hr from a collection line J15. As a result of analyzing the alkyltin alkoxide catalyst composition from the transport line J13 by $^{119}Sn,^{1}H,^{13}C$-NMR, 1,1,3,3-tetra-n-butyl-1,3-bis(3-methylbutyloxy)distannoxane was contained, and di-n-butyl-bis(3-methylbutyloxy)tin was not contained. After the continuous operation was performed for approximately 240 hours, the alkyltin alkoxide catalyst composition was extracted at 18 g/hr from an extraction line J16, whereas the 1,1,3,3-tetra-n-butyl-1,3-bis(3-methylbutyloxy)distannoxane produced by the method described above was supplied at 18 g/hr from a line J17.

Reference Example 2

Production of dibutyl carbonate

Step (II-1): Production of Dialkyltin Catalyst 692 g (2.78 mol) of di-n-butyltin oxide and 2001 g (27 mol) of 1-butanol (manufactured by Wako Pure Chemical Industries, Ltd., Japan) were placed in a 3000-mL (capacity) eggplant-shaped flask. The flask containing the mixture in a white slurry form was attached to an evaporator connected with an oil bath with a thermostat, a vacuum pump, and a vacuum controller. The purge valve outlet of the evaporator was connected with a line for nitrogen gas that flowed at normal pressure. After a pressure within the system was reduced by closing the purge valve of the evaporator, the purge valve was gradually opened to allow nitrogen to flow into the system, which was returned to normal pressure. The oil bath temperature was set to 126° C., the flask was dipped in the oil bath, and the rotation of the evaporator was initiated. After rotational stirring and heating were done for approximately 30 minutes at normal pressure with the purge valve of the evaporator opened, the mixed solution boiled, and the distillation of low-boiling-point components started. After this state was maintained for 8 hours, the purge valve was closed to gradually reduce a pressure within the system, and residual low-boiling-point components were distilled in the state where the pressure within the system was 76 to 54 kPa. After no more low-boiling-point components came out, the flask was taken out of the oil bath. The reaction solution became a clear solution. Then, the flask was taken out of the oil bath and the purge valve was gradually opened to return the pressure within the system to atmospheric pressure. 847 g of the reaction solution was obtained in the flask. From analysis results of $^{119}Sn,^{1}H,^{13}C$-NMR, a product 1,1,3,3-tetra-n-butyl-1,3-di(n-butyloxy)-distannoxane was obtained at a yield of 99% with respect to di-n-butyltin oxide. Similar procedures were repeated 12 times to obtain 10180 g in total of 1,1,3,3-tetra-n-butyl-1,3-di(n-butyloxy)-distannoxane Step (II-2): Production of Dibutyl Carbonate Carbonic acid ester was produced in the continuous production apparatus as shown in FIG. 13. To the tower reactor 1302 of 151 mm in inside diameter and 5040 mm in effective length filled with a packing material Mellapak 750Y (manufactured by Sulzer Chemtech Ltd., Switzerland), the 1,1,3,3-tetra-n-butyl-1,3-di(n-butyloxy)-distannoxane produced in Step (II-1) was supplied at 4201 g/hr from the supply line J4, and 1-butanol purified in the continuous multi-stage distillation column 1301 was supplied at 24717 g/hr from the line J2. The inside of the reactor was adjusted with a heater and the reboiler 1312 such that the solution temperature became 160° C., and adjusted with a pressure regulating valve such that the pressure became approximately 120 kPa-G. A residence time within the reactor was approximately 10 minutes. 24715 g/hr of 1-butanol containing water through the line J3 from the upper part of the reactor and 824 g/hr of 1-butanol through the supply line J1 were transported to the continuous multi-stage distillation column 1301 that was filled with a packing material Metal Gauze CY (manufactured by Sulzer Chemtech Ltd., Switzerland) and equipped with the reboiler 1311 and the condenser 1321, and distillation purification was performed. Above the continuous multi-stage distillation column 1301, a fraction containing a high concentration of water was condensed in the condenser 1321 and collected. The purified 1-butanol was transported through the line J2 located below the continuous multi-stage distillation column 1301. An alkyltin alkoxide catalyst composition containing di-n-butyltin-di-n-butyl oxide and 1,1,3,3-tetra-n-butyl-1,3-di(n-butyloxy)-distannoxane was obtained from the lower part of the tower reactor 1302 and supplied to the thin-film distillation apparatus 1303 (manufactured by KOBELCO ECO-SOLUTIONS Co., Ltd., Japan) through the line J5. 1-Butanol was distilled off in the thin-film distillation apparatus 1303 and returned to the tower reactor 1302 through the condenser 1323, the transport line J8, and the transport line J4. The alkyltin alkoxide catalyst composition was transported through the line J7 from the lower part of the thin-film distillation apparatus 1303 and supplied to the autoclave 1304 with the flow rate of the active components of di-n-butyltin-di-n-butyl oxide and 1,1,3,3-tetra-n-butyl-1,3-di(n-butyloxy)-distannoxane adjusted to approximately 4812 g/hr. Carbon dioxide was supplied at 973 g/hr via the supply line J9 to the autoclave, and the internal pressure of the autoclave was kept at 4 MPa-G A temperature in the autoclave was set to 120° C., a residence time was adjusted to approximately 4 hours, and the reaction between carbon dioxide and the alkyltin alkoxide catalyst composition was performed to obtain a reaction solution containing dibutyl carbonate. The reaction solution was transported via the line J10 and a regulating valve to the decarbonator 1305 by which residual carbon dioxide was removed and carbon dioxide was collected from the line J11. Then, the reaction solution was transported through the line 12 to the thin-film distillation apparatus 1306 (manufactured by KOBELCO ECO-SOLUTIONS Co., Ltd., Japan) adjusted to 140° C. and approximately 1.4 kPa, and supplied with the flow rate of 1,1,3,3-tetra-n-butyl-1,3-di(n-butyloxy)-distannoxane adjusted to approximately 4201 g/hr, to obtain a fraction containing dibutyl carbonate, whereas evaporation residues were circulated to the tower reactor 1302 through the line J13 and the line J4, with the flow rate of 1,1,3,3-tetra-n-butyl-1,3-di(n-butyloxy)-distannoxane adjusted to approximately 4201 g/hr. The fraction containing dibutyl carbonate was supplied at 830 g/hr through the condenser 1326 and the line J14 to the distillation column 1307 that was filled with a packing material Metal Gauze CY (manufactured by Sulzer Chemtech Ltd., Switzerland) and equipped with the reboiler 1317 and the condenser 1327, and after distillation purification was performed, 99 wt % of dibutyl carbonate was obtained at 814 g/hr from the transport line J 15. As a result of conducting analysis on the alkyltin alkoxide catalyst composition from the transport line J13 by $^{119}$Sn,$^{1}$H,$^{13}$C-NMR, 1,1,3,3-tetra-n-butyl-1,3-di(n-butyloxy)-distannoxane was contained, and di-n-butyltin-di-n-butyl oxide was not contained. After the continuous operation was performed for approximately 600 hours, the alkyltin alkoxide catalyst composition was extracted at 16 g/hr from the extraction line J16, whereas the 1,1,3,3-tetra-n-butyl-1,3-di(n-butyloxy)-distannoxane produced in Step (II-1) was supplied at 16 g/hr from the line J17.

Reference Example 3

Production of bis(2-ethylbutyl) carbonate

Step (III-1): Production of Dialkyltin Catalyst 893 g (2.48 mol) of di-n-octyltin oxide (manufactured by Sankyo Organic Chemicals Co., Ltd., Japan) and 2403 g (23.6 mol) of 2-ethyl-1-butanol were placed in a 5000-mL (capacity) eggplant-shaped flask. The flask was attached to an evaporator connected with an oil bath with a thermostat, a vacuum pump, and a vacuum controller. The purge valve outlet of the evaporator was connected with a line for nitrogen gas that flowed at normal pressure. After a pressure within the system was reduced by closing the purge valve of the evaporator, the purge valve was gradually opened to allow nitrogen to flow into the system, which was returned to normal pressure. The oil bath temperature was set to approximately 165° C., the flask was dipped in the oil bath, and the rotation of the evaporator was initiated. The distillation of 2-ethyl-1-butanol containing water started when heating was done for approximately 40 minutes under nitrogen at atmospheric pressure with the purge valve of the evaporator opened. After this state was maintained for 7 hours, the purge valve was closed to gradually reduce a pressure within the system, and excessive 2-ethyl-1-butanol was distilled in the state where the pressure within the system was 74 to 25 kPa. After no more fraction came out, the flask was taken out of the oil bath. After the flask was cooled to around room temperature (25° C.), the flask was taken out of the oil bath and the purge valve was gradually opened to return the pressure within the system to atmospheric pressure. 1125 g of the reaction solution was obtained in the flask. From analysis results of $^{119}$Sn,$^{1}$H,$^{13}$C-NMR, 1,1,3,3-tetra-n-octyl-1,3-bis(2-ethylbutyloxy)-distannoxane was confirmed to be obtained at a yield of 99% with respect to di-n-octyltin oxide. Similar procedures were repeated 12 times to obtain 13510 g in total of 1,1,3,3-tetra-n-octyl-1,3-bis(2-ethylbutyloxy)-distannoxane.

Step (III-2): Production of Carbonic Acid Ester and Collection of Inactivated Form Composition of Dialkyltin Catalyst Carbonic acid ester was produced in the continuous production apparatus as shown in FIG. 13. To the tower reactor 1302 of 151 mm in inside diameter and 5040 mm in effective length filled with a packing material Metal Gauze CY, the 1,1,3,3-tetra-n-octyl-1,3-bis(2-ethylbutyloxy)distannoxane produced above was supplied at 6074 g/hr from the line J4, and 2-ethyl-1-butanol purified in the continuous multi-stage distillation column 1301 was supplied at 12260 g/hr from the line J2. The reactor 1302 was adjusted with a heater and the reboiler 1312 such that the solution temperature became 160° C., and adjusted with a pressure regulating valve such that the pressure became approximately 120 kPa-G A residence time within the reactor was approximately 17 minutes. 12344 g/hr of 2-ethyl-1-butanol containing water through the line J3 from the upper part of the reactor and 958 g/hr of 2-ethyl-1-butanol through the line J1 were transported to the continuous multi-stage distillation column 1301 that was filled with a packing material Metal Gauze CY and equipped with the reboiler 1311 and the condenser 1321, and distillation purification was performed.

Above the continuous multi-stage distillation column 1301, a fraction containing a high concentration of water was condensed in the condenser 1321 and collected. The purified 2-ethyl-1-butanol was transported to the tower reactor 1302 through the line J2 located below the continuous multi-stage distillation column 1301. An alkyltin alkoxide catalyst composition containing di-n-octyl-bis(2-ethylbutyloxy)tin and 1,1,3,3-tetra-n-octyl-1,3-bis(2-ethylbutyloxy)distannoxane was obtained from the lower part of the tower reactor 1302 and supplied to the thin-film distillation apparatus 1303 through the line J5. 2-Ethyl-1-butanol was distilled off in the thin-film distillation apparatus 1303 and returned to the tower reactor 1302 through the condenser 1323, the line J8, and the line J4. The alkyltin alkoxide catalyst composition was transported through the line J7 from the lower part of the thin-film distillation apparatus 1303 and supplied to the autoclave 1304 with the flow rate of di-n-octyl-bis(2-ethylbutyloxy)tin and 1,1,3,3-tetra-n-octyl-1,3-bis(2-ethylbutyloxy)distannoxane adjusted to approximately 6945 g/hr, and. Carbon dioxide was supplied at 973 g/hr from the line J9 to the autoclave, and the internal pressure of the autoclave was kept at 4 MPa-G A temperature in the autoclave was set to 120° C., a residence time was adjusted to approximately 4 hours, and the reaction between carbon dioxide and the alkyltin alkoxide catalyst composition was performed to obtain a reaction solution containing bis(2-ethylbutyl) carbonate. The reaction solution was transported via the line J10 and a regulating valve to the decarbonator 1305 by which residual carbon dioxide was removed and carbon dioxide was collected from the line J11. Then, the reaction solution was transported through the line 12 to the thin-film distillation apparatus 1306 adjusted to approximately 142° C. and approximately 0.5 kPa, and supplied with the flow rate of 1,1,3,3-tetra-n-octyl-1,3-bis(2-ethylbutyloxy)distannoxane adjusted to approximately 6074 g/hr, to obtain a fraction containing bis(2-ethylbutyl) carbonate, whereas evaporation residues were circulated to the tower reactor 1302 through the line J13 and the line J4, with the flow rate of 1,1,3,3-tetra-n-octyl-1,3-bis(2-ethylbutyloxy)distannoxane adjusted to approximately 6074 g/hr. The fraction containing bis(2-ethylbutyl) carbonate was supplied at 959 g/hr through the condenser 1326 and the line J14 to the distillation column 1307 that was filled with a packing material Metal Gauze CY and equipped with the reboiler 1317 and the condenser 1327, and after distillation purification was performed, 99 wt % of bis(2-ethylbutyl) carbonate was obtained at 1075 g/hr from the collection line J15. As a result of conducting analysis on the alkyltin alkoxide catalyst composition from the line J13 by $^{119}Sn,^{1}H,^{13}C$-NMR, 1,1,3,3-tetra-n-octyl-1,3-bis(2-ethylbutyloxy)distannoxane was contained, and di-n-octyl-bis(2-ethylbutyloxy)tin was not contained. After the continuous operation was performed for approximately 220 hours, the alkyltin alkoxide catalyst composition was extracted at 18 g/hr from the extraction line J16, whereas the 1,1,3,3-tetra-n-octyl-1,3-bis(2-ethylbutyloxy) distannoxane produced by the method described above was supplied at 18 g/hr from the supply line J17.

Comparative Example 1

Step (a-1): Production of N,N'-hexanediyl-bis-carbamic acid diphenyl ester

Reactions were performed in the same way as in Step (1-1) of Example 1 to obtain a reaction solution (a) containing N,N'-hexanediyl-bis-carbamic acid diphenyl ester except that 13.40 kg (63 mol) of diphenyl carbonate (manufactured by Sigma-Aldrich Corp., USA), 9.96 kg (106 mol) of phenol (manufactured by Sigma-Aldrich Corp., USA), and 2.44 kg (21 mol) of hexamethylenediamine (manufactured by Sigma-Aldrich Corp., USA) were used as raw materials.

As a result of analyzing the reaction solution (a) by liquid chromatography, N,N'-hexanediyl-bis-carbamic acid diphenyl ester formed at a yield of 99.2%.

Figure 2:
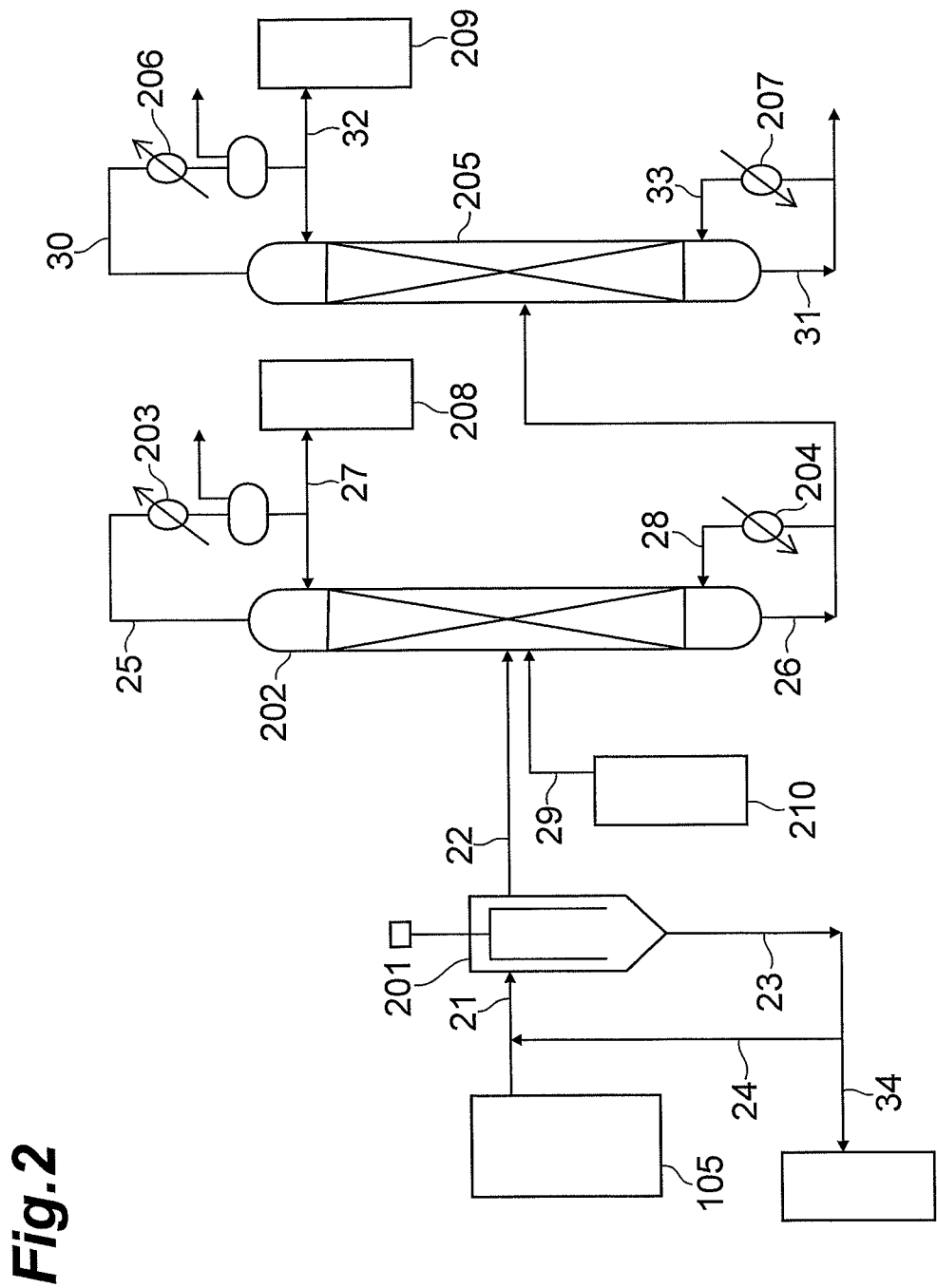
FIG. 2 is a conceptual diagram showing one example of an N-substituted carbamic acid ester thermally decomposing apparatus and an isocyanate separating apparatus.

Step (a-2): Thermal decomposition of N,N'-hexanediyl-bis-carbamic acid diphenyl ester and separation and collection of isocyanate Reactions were performed using the apparatus as shown in FIG. 2.

The thin-film distillation apparatus 201 was heated to 220° C., and the internal pressure was set to approximately 13 kPa. The reaction solution (a) collected into the reservoir 105 in Step (a-1) was heated to 150° C. and supplied at approximately 1.0 kg/hr to the upper part of the thin-film distillation apparatus 201 through the line 21, and the thermal decomposition of N,N'-hexanediyl-bis-carbamic acid diphenyl ester was performed to thereby obtain a mixture (a) containing an isocyanate and a hydroxy compound. Liquid-phase components were extracted through the line 23 from the bottom of the thin-film distillation apparatus 201 and circulated to the upper part of the thin-film distillation apparatus 201 through the line 24 and the line 21. The mixture (a) was extracted as gas-phase components through the line 22.

The mixture (a), which was gas-phase components, extracted through the line 22 from the thin-film distillation apparatus 201 was continuously fed to the intermediate stage of the continuous multi-stage distillation column 202 to perform the distillation separation of the mixture (a) which was gas-phase components. The quantity of heat necessary for the distillation separation was supplied by circulating the solution of the lower part of the column through the lines 26 and 28 and the reboiler 204. A gas discharged from the top of the continuous multi-stage distillation column 202 was condensed in the condenser 203 through the line 25 and continuously extracted through the line 27. On the other hand, liquid-phase components were extracted through the line 26 from the bottom of the column and supplied to the distillation column 205.

The liquid-phase components extracted through the line 26 were continuously fed to the intermediate stage of the continuous multi-stage distillation column 205 to perform the distillation separation of the liquid-phase components. The quantity of heat necessary for the distillation separation was supplied by circulating the solution of the lower part of the column through the lines 31 and 33 and the reboiler 207. A gas discharged from the top of the continuous multi-stage distillation column 205 was condensed in the condenser 206 through the line 30 and continuously extracted to the reservoir 209 through the line 32. The extracted amount at steady state was approximately 63 g/hr.

The solution extracted through the line 32 was a solution containing approximately 99.8 wt % of hexamethylene diisocyanate. The yield with respect to hexamethylenediamine was 46%.

Comparative Example 2

Step (b-1): Production of N,N'-hexanediyl-bis-carbamic acid diphenyl ester

Reactions were performed in the same way as in Step (1-1) of Example 1 to obtain a reaction solution (b) containing N,N'-hexanediyl-bis-carbamic acid diphenyl ester except that 12.2 kg (57 mol) of diphenyl carbonate, 11.3 kg (120 mol) of phenol, and 2.55 kg (22 mol) of hexamethylenediamine were used as raw materials.

As a result of analyzing the reaction solution (b) by liquid chromatography, N,N'-hexanediyl-bis-carbamic acid diphenyl ester formed at a yield of 98.1%.

Step (b-2): Thermal decomposition of N,N'-hexanediyl-bis-carbamic acid diphenyl ester and separation and collection of isocyanate Reactions were performed using the apparatus as shown in FIG. 2.

Thermal decomposition was performed in the same way as in Step (1-2) of Example 1 to obtain a mixture (b) containing an isocyanate and a hydroxy compound except that the reaction solution (b) obtained in Step (b-1) was used instead of the reaction solution (1).

Moreover, the separation and collection of the isocyanate were performed in the same way as in Step (1-2) of Example (1) except that p-xylene (manufactured by TOKYO CHEMICAL INDUSTRY CO., LTD., Japan) was fed at 0.3 kg/hr instead of n-dodecane. A gas discharged from the top of the continuous multi-stage distillation column 205 was condensed in the condenser 206 through the line 30 and continuously extracted to the reservoir 209 through the line 32.

The solution extracted through the line 32 was a solution containing approximately 99.3 wt % of hexamethylene diisocyanate. The yield with respect to hexamethylenediamine was 42%.

Incidentally, in the case where the normal boiling point of hexamethylene diisocyanate is defined as Tb and the normal boiling point of the hydroxy compound is defined as Ta, a normal boiling point Tc of p-xylene was in Tc<Ta<Tb.

Comparative Example 3

Step (c-1): Production of N,N'-hexanediyl-bis-carbamic acid diphenyl ester

Reactions were performed in the same way as in Step (1-1) of Example 1 to obtain a reaction solution (c) containing N,N'-hexanediyl-bis-carbamic acid diphenyl ester except that 10.3 kg (48 mol) of diphenyl carbonate, 12.2 kg (130 mol) of phenol, and 1.98 kg (17 mol) of hexamethylenediamine were used as raw materials.

As a result of analyzing the reaction solution (c) by liquid chromatography, N,N'-hexanediyl-bis-carbamic acid diphenyl ester formed at a yield of 98.6%.

Step (c-2): Thermal decomposition of N,N'-hexanediyl-bis-carbamic acid diphenyl ester and separation and collection of isocyanate Reactions were performed using the apparatus as shown in FIG. 2.

Thermal decomposition was performed in the same way as in Step (1-2) of Example 1 to obtain a mixture (c) containing an isocyanate and a hydroxy compound except that the reaction solution (c) obtained in Step (c-1) was used instead of the reaction solution (1).

Moreover, the separation and collection of the isocyanate were performed in the same way as in Step (1-2) of Example (1) except that 1,2-diphenylethane (manufactured by TOKYO CHEMICAL INDUSTRY CO., LTD., Japan) was fed at 0.2 kg/hr instead of n-dodecane. A gas discharged from the top of the continuous multi-stage distillation column 205 was condensed in the condenser 206 through the line 30 and continuously extracted to the reservoir 209 through the line 32.

The solution extracted through the line 32 was a solution containing approximately 98.1 wt % of hexamethylene diisocyanate. The yield with respect to hexamethylenediamine was 38%.

Incidentally, in the case where the normal boiling point of hexamethylene diisocyanate is defined as Tb and the normal boiling point of the hydroxy compound is defined as Ta, a normal boiling point Tc of 1,2-diphenylethane was in Ta<Tb<Tc.

INDUSTRIAL APPLICABILITY

The separation method of the present invention allows efficient separation in the separation of a mixture containing plural types of reversibly reacting compounds, especially, the separation of an isocyanate and a hydroxy compound that form by the thermal decomposition of an N-substituted carbamic acid ester. Thus, the separation method of the present invention is very industrially useful, and the commercial value is high.

REFERENCE SIGNS LIST 101, 102, 103, 105: Reservoir
104: Stirred tank
11, 12, 13, 14: Line
105, 208, 209, 210: Reservoir
201: Thin-film distillation apparatus
203, 206: Condenser
204, 207: Reboiler
202, 205: Continuous multi-stage distillation column
21, 22, 23, 24, 25, 26, 27, 28, 29, 30, 31, 32, 33, 34: Line
300, 301, 304, 305: Reservoir
302: Packed column
303: Condenser
306: Reboiler
31, 32, 33, 34: Line
400, 408, 409, 410: Reservoir
401: Thin-film distillation apparatus
403, 406: Condenser
404, 407: Reboiler
402, 405: Continuous multi-stage distillation column
41, 42, 43, 44, 45, 46, 47, 48, 49, A0, A1, A2, A3, A4: Line
500, 501, 502, 505: Reservoir
503: Stirred tank
504: Condenser
51, 52, 53, 54, 55: Line
601, 604: Reservoir
602: Packed column
603: Condenser
60, 62, 63: Line
701, 702, 703, 706: Reservoir
704: Stirred tank
705: Column
71, 72, 73, 74, 75: Line
801: Preheater
802: Continuous multi-stage distillation column
803: Condenser
804: Reboiler
805, 806: Reservoir
81, 82, 83, 84, 85: Line
901: Preheater 902: Continuous multi-stage distillation column
903: Condenser
904: Reboiler
905, 906: Reservoir
91, 92, 93, 94, 95: Line
1001: Thin-film distillation apparatus
1002, 1005: Continuous multi-stage distillation column
1003, 1006: Condenser
1004, 1007: Reboiler
1008, 1009, 1010, 1011: Reservoir
D0, D1, D2, D3, D4, D5, D6, D7, D8, D9, E0, E1, E2, E3, E4, E5: Line
1100, 1108, 1109, 1110: Reservoir
1101: Thin-film distillation apparatus
1102, 1105: Continuous multi-stage distillation column
1103, 1106, 1111: Condenser
1104, 1107: Reboiler
F1, F2, F3, F4, F5, F6, F7, F8, F9, G0, G1, G2, G3, G4, G5: Line
1201, 1204: Reservoir
1203: Stirred tank
H1 H2, H3, H4, H5: Line
1301, 1307: Distillation column
1302: Tower reactor
1303, 1306: Thin-film distillation apparatus
1304: Autoclave
1305: Decarbonator
1311, 1312, 1317: Reboiler
1321, 1323, 1326, 1327: Condenser
J1, J2, J3, J4, J5, J6, J7, J8, J9, J10, J11, J12, J13, J14, J15, J16, J17: Line

The invention claimed is:

1. A method for separating, with a multi-stage distillation column, a mixture containing an active hydrogen-containing compound (A) and a compound (B) that reversibly reacts with the active hydrogen-containing compound (A), the method comprising:
    distillation-separating the active hydrogen-containing compound (A) and the compound (B) with the multi-stage distillation column in the presence of an intermediate-boiling-point inactive compound (C) that has a normal boiling point between a normal boiling point of the active hydrogen-containing compound (A) and a normal boiling point of the compound (B) and is chemically inactive for the active hydrogen-containing compound (A) and the compound (B),
    wherein the compound (B) is extracted from the top of the multi-stage distillation column and the active hydrogen-containing compound (A) is extracted from the bottom of the multi-stage distillation column,
    the normal boiling point of the active hydrogen-containing compound (A) is higher than the normal boiling point of the compound (B),
    the mixture is a mixture obtained by the thermal decomposition reaction of a compound represented by formula (5):

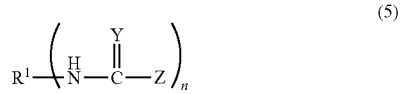

(5)

wherein $R^1$ represents one group selected from the group consisting of an aliphatic group having 1 to 22 carbon atoms and an aromatic group having 6 to 22 carbon atoms, and the group may contain an oxygen atom and/or a nitrogen atom; Y represents an oxygen atom or a sulfur atom; Z represents one group selected from the group consisting of a residue in which a hydrogen atom has been removed from an —OH group of a hydroxy compound, a residue in which a hydrogen atom has been removed from an —SH group of a thiol or the aromatic thiol, and a halogen atom; and n represents an integer of 1 to 10;
    the active hydrogen-containing compound (A) is at least one compound selected from the group consisting of a hydroxy compound, a thiol, an aromatic thiol, and a hydrogen halide; and
    the compound (B) is an isocyanate and/or an isothiocyanate.

2. The method according to claim 1, comprising supplying the mixture to an inactive layer comprising the intermediate-boiling-point inactive compound (C), formed within the multi-stage distillation column.

3. The method according to claim 1, comprising supplying the mixture in a gas state to the multi-stage distillation column.

4. The method according to claim 1, wherein the compound represented by formula (5) is an N-substituted thiocarbamic acid ester wherein Y is a sulfur atom and Z is a residue in which a hydrogen atom has been removed from the —OH group of the hydroxy compound.

5. The method according to claim 1, wherein the compound represented by formula (5) is an N-substituted carbamic acid ester wherein Y is an oxygen atom and Z is a residue in which a hydrogen atom has been removed from the —OH group of the hydroxy compound.

6. The method according to claim 5, wherein the N-substituted carbamic acid ester is an N-substituted carbamic acid ester obtained by reacting a carbonic acid ester and an organic primary amine.

7. The method according to claim 6, wherein the N-substituted carbamic acid ester is an N-substituted carbamic acid ester obtained by reacting urea, an organic primary amine, and a hydroxy compound.

8. The method according to claim 7, wherein the N-substituted carbamic acid ester is N-substituted aryl carbamate.

9. A method for producing an isocyanate, comprising: a step of obtaining a mixture containing an isocyanate and a hydroxy compound by the thermal decomposition reaction of an N-substituted carbamic acid ester; and a step of separating the isocyanate from the mixture by the method according to claim 1.

10. The method according to claim 1, wherein the normal boiling point of the intermediate-boiling-point inactive compound (C) differs by 5° C. or more from the normal boiling point of the active hydrogen-containing compound (A) and the normal boiling point of the compound (B).

11. The method according to claim 1, wherein the normal boiling point of the intermediate-boiling-point inactive compound (C) differs by 10° C. or more from the normal boiling point of the active hydrogen-containing compound (A) and the normal boiling point of the compound (B).

12. The method according to claim 1, wherein the mixture is a mixture obtained by a thermal decomposition reaction.

* * * * *